(12) United States Patent
Chalberg, Jr. et al.

(10) Patent No.: US 11,021,519 B2
(45) Date of Patent: *Jun. 1, 2021

(54) COMPOSITIONS AND METHODS FOR INTRAVITREAL DELIVERY OF POLYNUCLEOTIDES TO RETINAL CONES

(71) Applicants: Adverum Biotechnologies, Inc., Redwood City, CA (US); University of Washington, Seattle, WA (US)

(72) Inventors: Thomas W. Chalberg, Jr., Redwood City, CA (US); Jay Neitz, Seattle, WA (US); Maureen Neitz, Seattle, WA (US)

(73) Assignees: Adverum Biotechnologies, Inc., Redwood City, CA (US); University of Washington, Seattle, WA (US)

( * ) Notice: Subject to any disclaimer, the term of this patent is extended or adjusted under 35 U.S.C. 154(b) by 123 days.

This patent is subject to a terminal disclaimer.

(21) Appl. No.: 15/554,664

(22) PCT Filed: Mar. 2, 2016

(86) PCT No.: PCT/US2016/020482
§ 371 (c)(1),
(2) Date: Aug. 30, 2017

(87) PCT Pub. No.: WO2016/141078
PCT Pub. Date: Sep. 9, 2016

(65) Prior Publication Data
US 2018/0066022 A1 Mar. 8, 2018

Related U.S. Application Data

(60) Provisional application No. 62/134,466, filed on Mar. 17, 2015, provisional application No. 62/127,194, filed on Mar. 2, 2015.

(51) Int. Cl.
| | |
|---|---|
| *A61K 48/00* | (2006.01) |
| *A61P 27/02* | (2006.01) |
| *C07K 14/00* | (2006.01) |
| *C07K 14/015* | (2006.01) |
| *C12N 15/00* | (2006.01) |
| *C12N 15/86* | (2006.01) |
| *C07K 14/005* | (2006.01) |
| *C12N 15/861* | (2006.01) |
| *C12N 7/00* | (2006.01) |

(52) U.S. Cl.
CPC ........ *C07K 14/005* (2013.01); *A61K 48/0066* (2013.01); *A61K 48/0075* (2013.01); *C12N 15/86* (2013.01); *C12N 15/861* (2013.01); *C12N 7/00* (2013.01); *C12N 2750/14122* (2013.01); *C12N 2750/14143* (2013.01)

(58) Field of Classification Search
CPC .............. A61K 48/00; A61K 48/0058; A61K 48/0066; A61K 48/0075; A61P 27/02; C07K 14/00; C07K 14/01; C07K 14/015; C12N 15/00; C12N 15/86; C12N 15/8645; C12N 2750/14122; C12N 2750/14143
See application file for complete search history.

(56) References Cited

U.S. PATENT DOCUMENTS

| | | | |
|---|---|---|---|
| 4,522,811 | A | 6/1985 | Eppstein et al. |
| 4,874,237 | A | 10/1989 | Cringle |
| 5,219,401 | A | 6/1993 | Cathignol et al. |
| 5,383,917 | A | 1/1995 | Desai et al. |
| 5,436,146 | A | 7/1995 | Shenk et al. |
| 5,527,533 | A | 6/1996 | Tso et al. |
| 5,641,749 | A | 6/1997 | Yan et al. |
| 5,712,380 | A | 1/1998 | Kendall et al. |
| 5,753,500 | A | 5/1998 | Shenk et al. |
| 5,773,700 | A | 6/1998 | Van Grinsven et al. |
| 5,792,845 | A | 8/1998 | O'Reilly et al. |
| 5,814,618 | A | 9/1998 | Bujard et al. |
| 5,861,484 | A | 1/1999 | Kendall et al. |
| 5,994,136 | A | 11/1999 | Naldini et al. |
| 6,013,516 | A | 1/2000 | Verma et al. |
| 6,040,183 | A | 3/2000 | Ferrari et al. |
| 6,054,485 | A | 4/2000 | Schwartz et al. |
| 6,093,570 | A | 7/2000 | Ferrari et al. |
| 6,096,548 | A | 8/2000 | Stemmer |
| 6,132,732 | A | 10/2000 | Young et al. |
| 6,153,436 | A | 11/2000 | Hermonat et al. |

(Continued)

FOREIGN PATENT DOCUMENTS

| | | |
|---|---|---|
| CA | 2379220 A1 | 1/2001 |
| CN | 1325451 A | 12/2001 |

(Continued)

OTHER PUBLICATIONS

Dalkara et al, Science Translational Medicine 5(189): e189ra76, 11 pages, 2013.*
Nietz et al, Mol. Therapy 23 (Suppl 1): S80, Abstract 202, May 2015.*
Editorial, Ophthalmology 90(2): 126-31, 1983; abstract only.*
Schiefer et al, Ger. J. Ophthalmol. 4(1): 52-56, 1995; abstract only.*
U.S. Appl. No. 14/444,347, filed Jul. 28, 2014, Schaffer et al.
U.S. Appl. No. 14/444,375, filed Jul. 28, 2014, Schaffer et al.
U.S. Appl. No. 14/606,543, filed Jan. 27, 2015, Schaffer et al.
U.S. Appl. No. 14/938,154, filed Nov. 11, 2015, Schaffer et al.
U.S. Appl. No. 15/229,699, filed Aug. 5, 2016, Schaffer et al.

(Continued)

*Primary Examiner* — Kevin K Hill
(74) *Attorney, Agent, or Firm* — Cooley LLP

(57) ABSTRACT

Methods and compositions are provided for intravitreally delivering a polynucleotide to cone photoreceptors. Aspects of the methods include injecting a recombinant adeno-associated virus comprising a polynucleotide of interest into the vitreous of the eye. These methods and compositions find particular use in treating ocular disorders associated with cone dysfunction and/or death.

24 Claims, 14 Drawing Sheets
(10 of 14 Drawing Sheet(s) Filed in Color)
Specification includes a Sequence Listing.

(56) References Cited

U.S. PATENT DOCUMENTS

| | | |
|---|---|---|
| 6,287,815 B1 | 9/2001 | Brown |
| 6,329,181 B1 | 12/2001 | Xiao et al. |
| 6,387,670 B1 | 5/2002 | Leblois-Prehaud et al. |
| 6,458,157 B1 | 10/2002 | Suaning |
| 6,482,634 B1 | 11/2002 | Wilson et al. |
| 6,491,907 B1 | 12/2002 | Rabinowitz et al. |
| 6,548,286 B1 | 4/2003 | Samulski et al. |
| 6,596,539 B1 | 7/2003 | Stemmer et al. |
| 6,703,237 B2 | 3/2004 | Samulski et al. |
| 6,710,036 B2 | 3/2004 | Kurtzman et al. |
| 6,723,551 B2 | 4/2004 | Kotin et al. |
| 6,733,757 B2 | 5/2004 | Patel et al. |
| 6,855,314 B1 | 2/2005 | Chiorini et al. |
| 6,943,153 B1 | 9/2005 | Manning, Jr. et al. |
| 6,962,815 B2 | 11/2005 | Bartlett |
| 7,070,959 B1 | 7/2006 | Papadopoulos et al. |
| 7,071,159 B2 | 7/2006 | Kendall et al. |
| 7,172,893 B2 | 2/2007 | Rabinowitz et al. |
| 7,220,577 B2 | 5/2007 | Zolotukhin |
| 7,252,997 B1 | 8/2007 | Hallek et al. |
| 7,254,489 B2 | 8/2007 | Mossel |
| 7,285,381 B1 | 10/2007 | Hallek et al. |
| 7,314,912 B1 | 1/2008 | Hallek et al. |
| 7,368,428 B2 | 5/2008 | Serrero |
| 7,427,396 B2 | 9/2008 | Arbetman et al. |
| 7,556,965 B2 | 7/2009 | Hallek et al. |
| 7,585,676 B2 | 9/2009 | Mitrophanous et al. |
| 7,629,322 B2 | 12/2009 | Kleinschmidt et al. |
| 7,635,474 B2 | 12/2009 | Daly et al. |
| 7,666,405 B2 | 2/2010 | Amalfitano et al. |
| 7,749,492 B2 | 7/2010 | Bartlett et al. |
| 7,858,367 B2 | 12/2010 | Amalfitano et al. |
| 7,968,340 B2 | 6/2011 | Hallek et al. |
| 7,972,278 B2 | 7/2011 | Graham et al. |
| 8,075,137 B2 | 12/2011 | Klistorner et al. |
| 8,118,752 B2 | 2/2012 | Helling et al. |
| 8,137,274 B2 | 3/2012 | Weng et al. |
| 8,163,543 B2 | 4/2012 | Urabe et al. |
| 8,343,067 B2 | 1/2013 | Jones et al. |
| 8,524,446 B2 | 9/2013 | Gao et al. |
| 8,574,583 B2 | 11/2013 | Kay et al. |
| 8,632,764 B2 | 1/2014 | Xiao et al. |
| 8,663,624 B2 | 3/2014 | Schaffer et al. |
| 8,900,858 B2 | 12/2014 | Trono et al. |
| 9,193,956 B2 | 11/2015 | Schaffer et al. |
| 9,198,595 B2 | 12/2015 | Neitz et al. |
| 9,233,131 B2 | 1/2016 | Schaffer et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,587,282 B2 | 3/2017 | Schaffer et al. |
| 9,856,539 B2 | 1/2018 | Schaffer et al. |
| 9,943,573 B2 | 4/2018 | Constable et al. |
| 10,000,741 B2 | 6/2018 | Chalberg et al. |
| 10,004,788 B2 | 6/2018 | Constable et al. |
| 10,046,016 B2 | 8/2018 | Schaffer et al. |
| 10,202,657 B2 | 2/2019 | Schaffer et al. |
| 10,214,785 B2 | 2/2019 | Schaffer et al. |
| 2002/0136710 A1 | 9/2002 | Samulski et al. |
| 2002/0155610 A1 | 10/2002 | Colosi |
| 2002/0168342 A1 | 11/2002 | Wang et al. |
| 2002/0192823 A1 | 12/2002 | Bartlett |
| 2002/0194630 A1 | 12/2002 | Manning, Jr. et al. |
| 2003/0087889 A1 | 5/2003 | Strong et al. |
| 2003/0143732 A1 | 7/2003 | Fosnaugh et al. |
| 2003/0171254 A1 | 9/2003 | Sasaki et al. |
| 2004/0102765 A1 | 5/2004 | Koenig |
| 2004/0180440 A1 | 9/2004 | Zolotukhin |
| 2004/0234505 A1 | 11/2004 | Naylor et al. |
| 2005/0053922 A1 | 3/2005 | Schaffer et al. |
| 2005/0089973 A1 | 4/2005 | Yocum et al. |
| 2005/0106558 A1 | 5/2005 | Perabo et al. |
| 2005/0148069 A1 | 7/2005 | Gage et al. |
| 2005/0260203 A1 | 11/2005 | Wiegand et al. |
| 2005/0220766 A1 | 12/2005 | Bartlett et al. |
| 2005/0287122 A1 | 12/2005 | Bartlett et al. |
| 2006/0051333 A1 | 3/2006 | Arbetman et al. |
| 2006/0128020 A1 | 6/2006 | Calos |
| 2006/0166363 A1 | 7/2006 | Zolotukhin et al. |
| 2006/0193830 A1 | 8/2006 | Hauswirth et al. |
| 2006/0234347 A1 | 10/2006 | Harding et al. |
| 2006/0292117 A1 | 12/2006 | Loiler et al. |
| 2007/0020624 A1 | 1/2007 | Ruibenfield et al. |
| 2007/0036760 A1 | 2/2007 | Wilson et al. |
| 2007/0172460 A1 | 7/2007 | Kleinschmidt et al. |
| 2007/0188710 A1 | 8/2007 | Helling et al. |
| 2007/0190028 A1 | 8/2007 | Qu et al. |
| 2007/0190058 A1 | 8/2007 | Shams |
| 2007/0196338 A1 | 8/2007 | Samulski et al. |
| 2008/0152654 A1 | 6/2008 | Reich |
| 2008/0269149 A1 | 10/2008 | Bowles et al. |
| 2009/0112201 A1 | 4/2009 | Young |
| 2009/0128776 A1 | 5/2009 | Keating et al. |
| 2009/0191588 A1 | 7/2009 | Hermens et al. |
| 2009/0191597 A1 | 7/2009 | Samulski et al. |
| 2009/0202490 A1 | 8/2009 | Schaffer et al. |
| 2009/0203071 A1 | 8/2009 | Chen |
| 2009/0285826 A1 | 11/2009 | Bonnel et al. |
| 2010/0008170 A1 | 1/2010 | Sato et al. |
| 2010/0081707 A1 | 4/2010 | Ali et al. |
| 2010/0091242 A1 | 4/2010 | Baglini et al. |
| 2010/0166729 A9 | 7/2010 | Madison et al. |
| 2010/0172871 A1 | 7/2010 | Flannery et al. |
| 2010/0272719 A1 | 10/2010 | Yu |
| 2010/0297084 A1 | 11/2010 | Bennett et al. |
| 2011/0001465 A1 | 1/2011 | Sung et al. |
| 2011/0014655 A1 | 1/2011 | Otte et al. |
| 2011/0052678 A1 | 3/2011 | Shantha et al. |
| 2011/0104120 A1 | 5/2011 | Xiao et al. |
| 2011/0116046 A1 | 5/2011 | Haeri et al. |
| 2011/0136227 A1 | 6/2011 | Bakker et al. |
| 2011/0171262 A1 | 7/2011 | Bakker et al. |
| 2011/0200530 A1 | 8/2011 | Allemann et al. |
| 2011/0236353 A1 | 9/2011 | Wilson et al. |
| 2011/0270256 A1 | 11/2011 | Nelson et al. |
| 2012/0093772 A1 | 4/2012 | Horsager et al. |
| 2012/0100606 A1 | 4/2012 | Zolotukhin et al. |
| 2012/0141422 A1 | 6/2012 | Barkats |
| 2012/0164106 A1 | 6/2012 | Schaffer et al. |
| 2012/0172419 A1 | 7/2012 | Neitz et al. |
| 2012/0225930 A1 | 9/2012 | Acland et al. |
| 2013/0023034 A1 | 1/2013 | Noordman et al. |
| 2013/0031709 A1 | 2/2013 | Chen et al. |
| 2013/0317091 A1 | 11/2013 | Ye et al. |
| 2013/0323302 A1 | 12/2013 | Constable et al. |
| 2014/0242031 A1 | 8/2014 | Schaffer et al. |
| 2014/0275231 A1 | 9/2014 | Boye et al. |
| 2014/0294771 A1* | 10/2014 | Schaffer ............... C07K 14/005 424/93.2 |
| 2014/0341977 A1 | 11/2014 | Constable et al. |
| 2014/0364338 A1 | 12/2014 | Schaffer et al. |
| 2014/0371438 A1 | 12/2014 | Constable et al. |
| 2015/0004101 A1 | 1/2015 | Constable et al. |
| 2015/0079038 A1 | 3/2015 | Deverman et al. |
| 2015/0111275 A1 | 4/2015 | Palanker et al. |
| 2015/0118201 A1 | 4/2015 | Xiao et al. |
| 2015/0132262 A1 | 5/2015 | Schaffer et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2015/0025939 A1 | 9/2015 | Chalberg et al. |
| 2015/0259395 A1 | 9/2015 | Chalberg et al. |
| 2015/0315610 A1 | 11/2015 | Nishie et al. |
| 2016/0015288 A1 | 1/2016 | Neitz et al. |
| 2016/0017295 A1 | 1/2016 | Schaffer et al. |
| 2016/0102324 A1 | 4/2016 | Duchateau et al. |
| 2016/0184394 A1 | 6/2016 | Schaffer et al. |
| 2016/0340393 A1 | 11/2016 | Schaffer et al. |
| 2016/0375151 A1 | 12/2016 | Schaffer et al. |
| 2016/0376323 A1 | 12/2016 | Schaffer et al. |
| 2017/0096683 A1 | 4/2017 | Scaria et al. |
| 2017/0183647 A1 | 6/2017 | Chavez et al. |
| 2018/0125948 A1 | 5/2018 | Constable et al. |
| 2018/0127471 A1 | 5/2018 | Keravala et al. |

(56) References Cited

U.S. PATENT DOCUMENTS

| | | |
|---|---|---|
| 2018/0311319 A1 | 11/2018 | Constable et al. |
| 2018/0320145 A1 | 11/2018 | Chalberg et al. |
| 2018/0344197 A1 | 12/2018 | Neitz et al. |
| 2019/0218627 A1 | 7/2019 | Schaffer et al. |
| 2019/0255192 A1 | 8/2019 | Kirn et al. |

FOREIGN PATENT DOCUMENTS

| | | |
|---|---|---|
| CN | 1826414 A | 8/2006 |
| CN | 1966082 A | 5/2007 |
| CN | 101484005 A | 7/2009 |
| CN | 101532024 A | 9/2009 |
| EP | 0407122 A1 | 1/1991 |
| EP | 2292781 A1 | 3/2011 |
| EP | 2298925 A2 | 3/2011 |
| GB | 2545763 A | 6/2017 |
| JP | H11100327 A | 4/1999 |
| JP | 2002-539176 A | 11/2002 |
| JP | 2002363107 A | 12/2002 |
| JP | 2008-523813 A | 7/2008 |
| JP | 2014-518614 | 8/2014 |
| WO | WO 1992/008796 A1 | 5/1992 |
| WO | WO 1994/028143 A1 | 12/1994 |
| WO | WO 1995/022618 A1 | 8/1995 |
| WO | WO 1995/026409 A1 | 10/1995 |
| WO | WO 1997/038723 A1 | 10/1997 |
| WO | WO 1998/013071 A1 | 4/1998 |
| WO | WO 1998/051323 A1 | 11/1998 |
| WO | WO 1999/014354 A1 | 3/1999 |
| WO | WO 1999/016889 A1 | 4/1999 |
| WO | WO 1999/036511 A2 | 7/1999 |
| WO | WO 1999/045952 A2 | 9/1999 |
| WO | WO 1999/066959 A2 | 12/1999 |
| WO | WO 1999/067393 A2 | 12/1999 |
| WO | WO 2000/001815 A2 | 1/2000 |
| WO | WO 2000/015822 A1 | 3/2000 |
| WO | WO 2000/028004 A1 | 5/2000 |
| WO | WO 2001/070276 A2 | 9/2001 |
| WO | WO 2002/012525 A2 | 2/2002 |
| WO | WO 2002/053703 A2 | 7/2002 |
| WO | WO 2002/082904 A2 | 10/2002 |
| WO | WO 2003/018820 A2 | 3/2003 |
| WO | WO 2003/023032 A2 | 3/2003 |
| WO | WO 2003/054197 A2 | 7/2003 |
| WO | WO 2003/080648 A2 | 10/2003 |
| WO | WO 2003/093436 A2 | 11/2003 |
| WO | WO 2004/079332 A2 | 9/2004 |
| WO | WO 2004/108922 A2 | 12/2004 |
| WO | WO 2004/112727 A2 | 12/2004 |
| WO | WO 2005/005610 A2 | 1/2005 |
| WO | WO 2005/033321 A1 | 4/2005 |
| WO | WO 2006/066066 A2 | 6/2006 |
| WO | WO 2006/110689 A2 | 10/2006 |
| WO | WO 2007/084773 A2 | 7/2007 |
| WO | WO 2007/120542 A2 | 10/2007 |
| WO | WO 2007/148971 A2 | 12/2007 |
| WO | WO 2008/131951 A1 | 11/2008 |
| WO | WO 2008/142124 A1 | 11/2008 |
| WO | WO 2008/150459 A1 | 12/2008 |
| WO | WO 2009/073551 A2 | 6/2009 |
| WO | WO 2009/104964 A1 | 8/2009 |
| WO | WO 2009/105669 A2 | 8/2009 |
| WO | WO 2009/137006 A2 | 11/2009 |
| WO | WO 2009/154452 A2 | 12/2009 |
| WO | WO 2010/093784 A2 | 8/2010 |
| WO | WO 2010/099960 A2 | 9/2010 |
| WO | WO 2010/138263 A2 | 12/2010 |
| WO | WO 2011/020710 A2 | 2/2011 |
| WO | WO 11/034947 * | 3/2011 |
| WO | WO 2011/034947 A2 | 3/2011 |
| WO | WO 2011/088081 A1 | 7/2011 |
| WO | WO 2011/112089 A2 | 9/2011 |
| WO | WO 2011/117258 A2 | 9/2011 |
| WO | WO 2011/122950 A1 | 10/2011 |
| WO | WO 2011/126808 A2 | 10/2011 |
| WO | WO 2011/137344 A2 | 11/2011 |
| WO | WO 2012/068317 A2 | 5/2012 |
| WO | WO 2012/145601 A2 | 10/2012 |
| WO | WO 2013/029030 A1 | 2/2013 |
| WO | WO 2013/170078 A1 | 11/2013 |
| WO | WO 2013/173129 A2 | 11/2013 |
| WO | WO 2013/173512 A2 | 11/2013 |
| WO | WO 2013/188316 A1 | 12/2013 |
| WO | WO 2014/186160 A1 | 11/2014 |
| WO | WO 2014/194132 A1 | 12/2014 |
| WO | WO 2014/207190 A1 | 12/2014 |
| WO | WO 2015/048534 A1 | 4/2015 |
| WO | WO 2015/054653 A2 | 4/2015 |
| WO | WO 2015/058048 A1 | 4/2015 |
| WO | WO 2015/134643 A1 | 9/2015 |
| WO | WO 2015/142941 A1 | 9/2015 |
| WO | WO 2015/168666 A2 | 11/2015 |
| WO | WO 2015/191693 A2 | 12/2015 |
| WO | WO 2016/141078 A1 | 9/2016 |
| WO | WO 2016/144892 A1 | 9/2016 |
| WO | WO 2017/023724 A1 | 2/2017 |
| WO | WO 2017/112868 A1 | 6/2017 |
| WO | WO 2017/190125 A1 | 11/2017 |
| WO | WO 2017/197355 A2 | 11/2017 |
| WO | WO 2017/218974 A2 | 12/2017 |
| WO | WO 2017/218981 A2 | 12/2017 |
| WO | WO 2018/075798 A1 | 4/2018 |
| WO | WO 2018/160686 A1 | 9/2018 |
| WO | WO 2018/170473 A1 | 9/2018 |

OTHER PUBLICATIONS

U.S. Appl. No. 15/244,884, filed Aug. 23, 2016, Schaffer et al.
U.S. Appl. No. 15/244,892, filed Aug. 23, 2016, Schaffer et al.
U.S. Appl. No. 15/939,674, filed Mar. 29, 2018, Neitz, et al.
U.S. Appl. No. 15/961,654, filed Apr. 24, 2018, Constable et al.
Acland, et al., "Long-term restoration of rod and cone vision by single dose rAAV mediated gene transfer to the retina in a canine model of childhood blindness." Mol Ther. 2005; 12(6): 1072-1082.
Adachi, et al., "A New Recombinant Adena-Associated Virus (AAV)-Based Random Peptide Display Library System: Infection-Defective AVV 1 .9-3 as a Novel Targeted Platform for Vector Evolution"; Gene Therapy and Requlation; vol. 5, No. 1, pp. 31-55 (Oct. 2010).
Adamis, et al., "Inhibition of vascular endothelial growth factor prevents retinal ischemia-associated iris neovascularization in a nonhuman primate." Arch Ophthalmol. 1996; 114(1): 66-71.
Adhi, et al., "Optical coherence tomography—current and future applications." Curr Opin Ophthalmol. 2013; 24(3): 213-221.
Aflibercept FDA Entry and Label, 2015. 28 pages. downloaded from http://www.accessdata.fda.gov/scripts/cder/drugsatfda/index.cfm?fuseaction=Search.Labei_ApprovaiHistory#apphist.
Aiello, et al., "Suppression of retinal neovascularization in vivo by inhibition of vascular endothelial growth factor (VEGF) using soluble VEGF-receptor chimeric proteins." Proc Natl Acad Sci USA. 1995; 92(23):10457-10461.
Akimoto, et al., "Adenovirally expressed basic fibroblast growth factor rescues photoreceptor cells in RCS rats." Invest Ophthalmol Vis Sci. 1999; 40(2): 273-279.
Akiyama, et al., "Intraocular Injection of an Aptamer that Binds PDGF-B: A Potential Treatment for Proliferative Retinopathies," Journal of Cellular Physiology, vol. 207, pp. 407-412 (2006).
Albert, Henrik, et al. "Site-specific integration of DNA into wild-type and mutant lox sites placed in the plant genome." The Plant Journal (1995); 7.4: 649-659.
Alexander, John J., et al. "Restoration of cone vision in a mouse model of achromatopsia." Nature Medicine (2007); 13.6: 685-687.
Ali, et al., "Gene therapy for inherited retinal degeneration." Br J Ophthalmol. 1997; 81(9): 795-801.
Ali, et al., "Restoration of photoreceptor ultrastructure and function in retinal degeneration slow mice by gene therapy." Nature Genetics; vol. 25, pp. 306-310 (Jul. 2000).
Allocca, et al., "Novel adeno-associated virus serotypes efficiently transduce murine photoreceptors", Journal of Virology (Oct. 2007), 81(20): 11372-11380.

(56) References Cited

OTHER PUBLICATIONS

Amado, et al., "Safety and efficacy of subretinal readministration of a viral vector in large animals to treat congenital blindness." Sci Transl Med. 2010; 2(21): 21ra16. doi: 10.1126/scitranslmed. 3000659.
Anand, et al., "A deviant immune response to viral proteins and transgene product is generated on subretinal administration of adenovirus and adena-associated virus." Mol Ther. 2002; 5(2):125-132.
Arnold, et al., "Extracts from "clinical evidence": age related macular degeneration." BMJ. 2000; 321(7263):741-744.
Asokan, et al., "Reengineering a receptor footprint of adeno-associated virus enables selective and systemic gene transfer to muscle", Nat Biotechnol, (Jan. 2010); 28(1): 79-82.
Asuri, et al., "Directed evolution of adeno-associated virus for enhanced gene delivery and gene targeting in human pluripotent stem cells." Mol Ther. (Feb. 2012); 20(2): 329-338. Epub Nov. 22, 2011.
Score Search Results / Report for Per SEQ ID No. 17 per US2002/0192823 (U.S. Appl. No. 10/038,972) to Bartlett Published Dec. 19, 2002, 2 pages.
Auricchio, et al., "Exchange of surface proteins impacts on viral vector cellular specificity and transduction characteristics: the retina as a model." Hum Mol Genet. 2001; 10(26): 3075-3081.
Auricchio, et al., "Inhibition of retinal neovascularization by intraocular viral-mediated delivery of anti-angiogenic agents." Mol Ther. 2002; 6(4): 490-494.
Bailey, et al., "Exercise increases soluble vascular endothelial growth factor receptor-1 (sFlt-1) in circulation of healthy volunteers." Med Sci Monit. 2006; 12(2): CR45-50.
Bainbridge, et al., "Effect of gene therapy on visual function in Leber's congenital amaurosis." N Engl J Med. 2008; 358(21): 2231-2239.
Bainbridge, et al., "Inhibition of retinal neovascularisation by gene transfer of soluble VEGF receptor sFlt-1." Gene Ther. 2002; 9(5): 320-326.
Bainbridge, J. W., and Ali, R. R. "The eyes have it! Ocular gene therapy trials for LCA look promising." Gene Ther (2008); 15: 1191-1192.
Barleon, et al., "Mapping of the sites for ligand binding and receptor dimerization at the extracellular domain of the vascular endothelial growth factor receptor FLT-1." J Biol Chem. 1997; 272(16):10382-10388.
Barleon, et al., "Soluble VEGFR-1 secreted by endothelial cells and monocytes is present in human serum and plasma from healthy donors." Angiogenesis. 2001; 4(2):143-154.
Belgore, et al., "Plasma levels of vascular endothelial growth factor (VEGF) and its receptor, Flt-1, in haematological cancers: a comparison with breast cancer." Am J Hematol. 2001; 66(1): 59-61.
Belteki, Gusztav, et al. "Site-specific cassette exchange and germline transmission with mouse ES cells expressing φC31 integrase." Nature Biotechnology (2003); 21.3: 321-324.
Bennett, "Immune response following intraocular delivery of recombinant viral vectors." Gene Ther. 2003; 10(11): 977-982.
Bennett, et al., "AAV2 gene therapy readministration in three adults with congenital blindness." Sci Transl Med. 2012; 4(120): 120ra15.
Bennett, et al., "Gene therapy for retinitis pigmentosa." Curr Opin Mol Ther. 2000; 2(4): 420-425.
Bennicelli, et al., "Reversal of blindness in animal models of leber congenital amaurosis using optimized AAV2-mediated gene transfer." Mol Ther. 2008; 16(3): 458-465.
Berge, et al., "Pharmaceutical salts." J Pharm Sci. 1977; 66(1): 1-19.
Bethke, Bruce, and Sauer, Brian. "Segmental genomic replacement by Cre-mediated recombination: genotoxic stress activation of the p53 promoter in single-copy transformants." Nucleic Acids Research (1997); 25.14: 2828-2834.
Bhisitkul, "Vascular endothelial growth factor biology: clinical implications for ocular treatments." Br J Ophthalmol. 2006; 90(12): 1542-1547.
Bi, Yanzhen, et al. "Pseudo attP sites in favor of transgene integration and expression in cultured porcine cells identified by streptomyces phage phiC31 integrase." BMC Molecular Biology (2013); 14: 20, 12 pages.
Bichsel, et al., "Bacterial delivery of nuclear proteins into pluripotent and differentiated cells", PLoS One (Jan. 2011); 6(1): e16465, pp. 1-9.
Blacklow, et al., "A Seroepidemiologic Study of Adenovirus-Associated Virus Infection in Infants and Children." Am J Epidemiol.; vol. 94, No. 4, pp. 359-366 (Oct. 1971).
Boucas,et al., "Engineering adeno-associated virus serotype 2-based targeting vectors using a new insertion site-position 453-and single point mutations." J Gene Med., Dec. 2009, 11(12):1103-1113.
Brinkmann, et al., "Origin of retinal pigment epithelium cell damage by pulsed laser irradiance in the nanosecond to microsecond time regimen." Laser Surg Med. 2000; 27: 451-464.
Brinkmann, et al., "Selective retina therapy (SRT): a review on methods, techniques, preclinical and first clinical results." Bull Soc Beige Ophtalmol. 2006; 302: 51-69.
Brown, et al., "Ranibizumab versus verteporfin photodynamic therapy for neovascular age-related macular degeneration: Two-year results of the Anchor study." Ophthalmology. 2009; 116(1): 57-65.
Buch, et al., "In Contrast to AAC-Mediated Cntf Expression. AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors", Gene Therapy, 2003, vol. 10, pp. 1142-1511.
Büning, Hildegard, et al. "Recent developments in adeno-associated virus vector technology." The Journal of Gene Medicine (2008); 10.7: 717-733.
Cai, Xue, et al. "Gene delivery to mitotic and postmitotic photoreceptors via compacted DNA nanoparticles results in improved phenotype in a mouse model of retinitis pigmentosa." The FASEB Journal (2010); 24.4: 1178-1191.
Calcedo, Roberto, et al. "Worldwide epidemiology of neutralizing antibodies to adeno-associated viruses." Journal of Infectious Diseases (2009); 199.3: 381-390.
Calos, Michele P. "The φC31 Integrase System for Gene Therapy." Current Gene Therapy (2006); 6.6: 633-645.
Calvo, et al., "Upstream open reading frames cause widespread reduction of protein expression and are polymorphic among humans." PNAS (May 2009); 106 (18): 7507-7512. Epub Apr. 16, 2009.
Campochiaro, "Molecular targets for retinal vascular diseases." J Cell Physiol. 2007; 210(3): 575-581.
Campochiaro, "Gene Transfer for Neovascular Age-Related Macular Degeneration." Human Gene Therapy (2011); 22(5): 523-529.
Campochiaro, et al., "Adenoviral vector-delivered pigment epithelium-derived factor for neovascular age-related macular degeneration: results of a phase I clinical trial." Hum Gene Ther. 2006; 17(2): 167-176.
Campochiaro, et al., "Monitoring ocular drug therapy by analysis of aqueous samples." Ophthalmology. 2009; 116(11): 2158-2164.
Cao, et al., "A subretinal matrigel rat choroidal neovascularization (CNV) model and inhibition of CNV and associated inflammation and fibrosis by VEGF trap." Invest Ophthalmol Vis Sci. 2010; 51(11): 6009-6017.
Cayouette, et al., "Adenovirus-mediated gene transfer of ciliary neurotrophic factor can prevent photoreceptor degeneration in the retinal degeneration (rd) mouse." Hum Gene Ther. 1997; 8(4): 423-430.
Chadderton, et al.; "Improved Retinal Function in a Mouse Model of Dominant Retinitis Pigmentosa Following AVV-delivered Gene Therapy"; Molecular Therapy; vol. 17, No. 4, pp. 593-599 (Apr. 2009).
Chakrabarti, et al., "Normal T-cell turnover in sooty mangabeys harboring active simian immunodeficiency virus infection." J Virol. 2000; 74(3): 1209-1223.
Chalberg, et al., "Integration Specificity of Phage φC31 Integrase in the Human Genome", J Mol Biol. (Mar. 17, 2006); 357(1): 28-48. Epub Dec. 22, 2005.

(56) References Cited

OTHER PUBLICATIONS

Chalberg, et al. "φC31 integrase confers genomic integration and long-term transgene expression in rat retina." Investigative Ophthalmology & Visual Science (2005); 46.6: 2140-2146.
Chen, et al., "Use of nepafenac (Nevanac) in combination with intravitreal anti-VEGF agents in the treatment of recalcitrant exudative macular degeneration requiring monthly injections." Clin Ophthalmol. 2010; 4:1249-1252.
Chiu, M. I., and Nathans, J. "Blue cones and cone bipolar cells share transcriptional specificity as determined by expression of human blue visual pigment-derived transgenes." The Journal of Neuroscience (1994); 14.6: 3426-3436.
Choi, et al., "Production of recombinant adena-associated viral vectors." Curr Protoc Hum Genet. 2007; Chapter 12: Unit 12.9.doi: 10.1002/0471142905.hg1209s53.
Choi, et al.; "AAV Hybrid Serotypes: Improved Vectors for Gene Delivery."; Current Gene Therapy; vol. 5, No. 3, pp. 299-310 (Jun. 2005).
Chung, et al., "Angiogenesis in myocardial infarction. An acute or chronic process?" Eur Heart J. 2002; 23(20): 1604-1608.
Cideciyan, Artur V., et al. "Human gene therapy for RPE65 isomerase deficiency activates the retinoid cycle of vision but with slow rod kinetics." Proceedings of the National Academy of Sciences (2008); 105.39: 15112-15117.
Cideciyan, et al., "Human RPE65 gene therapy for Leber congenital amaurosis: persistence of early visual improvements and safety at 1 year." Hum Gene Ther. 2009; 20(9): 999-1004.
Clark, et al., "Expression of clusterin/sulfated glycoprotein-2 under conditions of heat stress in rat Sertoli cells and a mouse Sertoli cell line." J Androl. 1997; 18(3): 257-63.
Clinical trial, A Phase I/II Controlled Dose-escalating Trial to Establish the Baseline Safety and Efficacy of a Single Subretinal Injection of rAAV.sFit-1 Into Eyes of Patients With Exudative Age-related Macular Degeneration (AMD). NCT01494805. Updated—Dec. 16, 2011, 4 pages.
Clinical trial. Safety and Tolerability Study of AAV2-sFLT-1 in Patients With Neovascular Age-Related Macular Degeneration (AMD). NCT01024998. Last updated: Jan. 28, 2014.
Comparison of L-opsin promoter to SEQ ID No. 80. Printed Feb. 2, 2017, in U.S. Appl. No. 14/660,657, 4 pages.
Costa, et al., "Intravitreal Bevacizumab for Choroidal Neovascularization Caused by AMD (IBeNA Study): Results of a Phase 1 Dose-Escalation Study." Investigative Ophthalmology & Visual Science (2006); 47 (10): 4569-4578.
Csermely, et al., "The 90-kDa molecular chaperone family: structure, function, and clinical applications. A comprehensive review." Pharmacol Ther. 1998; 79(2):129-168.
Curtis, et al., "Risks of mortality, myocardial infarction, bleeding, and stroke associated with therapies for age-related macular degeneration." Arch Ophthalmol. 2010; 128(10): 1273-1279.
Dalkara, Deniz, et al. "In vivo—directed evolution of a new adeno-associated virus for therapeutic outer retinal gene delivery from the vitreous." Science Translational Medicine (2013); 5 (189): 189ra76-189ra76.
Dalkara, et al.,"Developing Photoreceptor Targeted AAV Variant by Directed Evolution." ARVO Annual Meeting Abstract Search and Program Planner; vol. 2011, pp. 4381 (May 2011 ).
Database Geneseq [Online] Oct. 16, 2008 (Oct. 16, 2008), "Modified Adena-associated virus (hu.44) capsid protein, VP1, hu.44R2.", retrieved from EBI accession No. GSP:AEL63853, Database accession No. AEL63853, 1 page.
Database Geneseq [Online] Oct. 16, 2008 (Oct. 16, 2008), "Modified Adena-associated virus (hu.44) capsid protein, VP1, hu.44R3.", retrieved from EBI accession No. GSP:AEL63854, Database accession No. AEL63854.
Davidson, et al., "A model system for in vivo gene transfer into the central nervous system using an adenoviral vector." Nat Genet. 1993; 3(3): 219-223.

Davis, et al., "Direct gene transfer into skeletal muscle in vivo: factors affecting efficiency of transfer and stability of expression." Hum Gene Ther. 1993; 4(2): 151-159.
Dawson, et al., "Pigment epithelium-derived factor: a potent inhibitor of angiogenesis." Science. 1999; 285(5425): 245-248.
Day, et al., "Advances in AAV vector development for gene therapy in the retina." Adv Exp Med Biol. (2014); 801: 687-693.
De Vries, et al., "The fms-like tyrosine kinase, a receptor for vascular endothelial growth factor." Science. 1992; 255(5047): 989-991.
Definition of "plasmid", Biology Dictionary, 2018, 1 page.
Dejneka, et al., "Gene therapy and animal models for retinal disease." Dev Ophthalmol. 2003; 37: 188-198.
Dejneka, et al., "Gene therapy and retinitis pigmentosa: advances and future challenges." Bioessays 2001; 23(7): 662-8.
Den Dunnen, et al., "Mutation nomenclature extensions and suggestions to describe complex mutations: a discussion."; Human Mutation; vol. 15, pp. 7-12 (2000).
Deonarain, M.P., "Ligand-targeted receptor-mediated vectors for gene delivery", Expert Opinion on Therapeutic Patents. 1998; 8: 53-69.
DeValois, R.L. and DeValois, K.K. "A multi-stage color model." Vision Research (1993); 33.8: 1053-1065.
Deyle and Russell, "Adeno-associated virus vector integration." Curr. Opin. Mol. Therapy (2009); 11 (4): 442-447.
Diab, et al., "Angiogenic factors for the prediction of pre-eclampsia in women with abnormal midtrimester uterine artery Doppler velocimetry." Int J Gynaecol Obstet. 2008; 102(2):146-151.
Diprimo, et al., "Surface loop dynamics in adeno-associated virus capsid assembly", Journal of Virology (2008); vol. 82, No. 11, pp. 5178-5189.
Dudus, et al., "Persistent trans gene product in retina, optic nerve and brain after intraocular injection of rAAV." Vision Res. 1999; 39(15): 2545-2553.
Dull, et al., "A third-generation lentivirus vector with a conditional packaging system." Journal of Virology (1998), 72(11):8463-8671.
Easton, et al., "The Hsp110 and Grp170 stress proteins: newly recognized relatives of the Hsp70s." Cell Stress Chaperones. 2000; 5(4): 276-290.
Edelstein et al., "Gene therapy clinical trials worldwide 1989-2004—an overview", Journal Gene Med. (2004); 6: 597-602.
Erles et al.; "Update on the prevalence of serum antibodies (IgG and IgM) to adeno-associated virus (AAV)." J Med Virol.; vol. 59, No. 3, pp. 406-411 (Nov. 1999).
European Patent Application No. 13791695.3, Extended European Search Report dated Dec. 21, 2015, 10 pages.
European Patent Application No. 15765668.7, Extended European Search Report dated Mar. 7, 2018, 18 pages.
European Patent Application No. 15765668.7, Partial Supplemental European Search Report dated Nov. 10, 2017, 8 pages.
European Patent Application No. 16759427, Extended European Search Report dated Aug. 8, 2018, 9 pages.
Excoffon, et al., "Directed evolution of adeno-associated virus to an infectious respiratory virus." Proc Natl Acad Sci U S A. (Mar. 2009); 106(10): 3865-3870.
Ferrara, "Vascular endothelial growth factor: basic science and clinical progress." Endocr Rev. 2004; 25(4): 581-611.
Flotte, et al.; "Gene expression from adeno-associated virus vectors in airway epithelial cells." Am J Respir Cell Mol Biol.; vol. 7, No. 3, pp. 349-356 (Sep. 1992).
Fong, et al., "The use and development of retroviral vectors to deliver cytokine genes for cancer therapy." Crit Rev Ther Drug Carrier Syst. 2000; 17(1): 1-60.
Fotsis, et al., "The endogenous oestrogen metabolite 2-methoxyoestradiol inhibits angiogenesis and suppresses tumour growth." Nature. 1994; 368(6468): 237-239.
Framme, et al., "Selective targeting of the retinal pigment epithelium in rabbit eyes with a scanning laser beam." Investigative Ophthalmology & Visual Science. 2007; 48(4): 1782-1792.
Funk, et al., "Neovascular age-related macular degeneration: intraocular cytokines and growth factors and the influence of therapy with ranibizumab." Ophthalmology. 2009; 116(12): 2393-2399.

(56) References Cited

OTHER PUBLICATIONS

Galan, et al., "Association of age-related macular degeneration with polymorphisms in vascular endothelial growth factor and its receptor." Ophthalmology. 2010; 117(9): 1769-1774.
Geller, et al., "An HSV-1 vector expressing tyrosine hydroxylase causes production and release of L-dopa from cultured rat striatal cells." J Neurochem. 1995; 64(2):487-496.
Geller, et al., "Infection of cultured central nervous system neurons with a defective herpes simplex virus 1 vector results in stable expression of *Escherichia coli* beta-galactosidase." Proc Natl Acad Sci USA. 1990; 87(3): 1149-1153.
Geller, et al., "Long-term increases in neurotransmitter release from neuronal cells expressing a constitutively active adenylate cyclase from a herpes simplex virus type 1 vector." Proc Natl Acad Sci USA. 1993; 90(16): 7603-7607.
GenBank accession No. AAZ79678; rat AAV1 VP3 capsid protein sequence downloaded from NCBI; downloaded on Nov. 3, 2008.
GenBank [online], Accession No. U47119.2, "Cloning vector pCI, mammalian expression vector." May 10, 2004—uploaded, [retrieved on Apr. 12, 2017], https://www.ncbi.nlm.nih.gov/nuccore/U47119, 2 pages.
GenBank accession No. ABZ10812; AAV13 capsid protein sequence downloaded from NBCI; downloaded on Nov. 3, 2008.
Gerdes, et al., "Cell cycle analysis of a cell proliferation-associated human nuclear antigen defined by the monoclonal antibody Ki-67." J Immunol. 1984; 133(4):1710-1715.
Girod, et al., "Genetic capsid modifications allow efficient re-targeting of adeno-associated virus type 2." Nat. Med. (1999); vol. 5, No. 9, pp. 1052-1056.
Glushakova, Lyudmyla G., et al. "Human blue-opsin promoter preferentially targets reporter gene expression to rat s-cone photoreceptors." Investigative Ophthalmology & Visual Science (2006); 47.8: 3505-3513.
Goldman, et al., "Paracrine expression of a native soluble vascular endothelial growth factor receptor inhibits tumor growth, metastasis, and mortality rate." Proc Natl Acad Sci USA. 1998; 95(15): 8795-8800.
Goverdhana, et al., Regulatable gene expression systems for gene therapy applications: progress and future challenges. Molecular Therapy : The Journal of the American Society of Gene Therapy. 2005; 12(2): 189-211.
Gragoudas, et al., "Pegaptanib for neovascular age-related macular degeneration." N Engl J Med. 2004; 351(27): 2805-2816.
Graubert, et al., "Vascular repair after menstruation involves regulation of vascular endothelial growth factor-receptor phosphorylation by sFLT-1." Am J Pathol. 2001; 158(4): 1399-1410.
Gray and Zolotukhin, "Design and Construction of Functional AVV Vectors." Methods in Molecular Biology. 2011; 807: 25-46.
Gray, et al., "Directed Evolution of a Novel Adeno-associated Virus (AVV) Vector That Crosses the Seizure-compromised Blood-Brain Barrier (BBB)." Molecular Therapy; vol. 18, No. 3, pp. 570-578 (2010).
Gregory-Evans, et al., "Ex vivo Gene Therapy Using Intravitreal Injection of GDNF-secreting Mouse Embryonic Stem Cells in a Rat Model of Retinal Degeneration." Molecular Vision; vol. 15, pp. 962-973 (May 13, 2009).
Grieger, et al., "Separate Basic Region Motifs within the Adena-Associated Virus Capsid Proteins Are Essential for Infectivity and Assembly." J. Viral. (2006); 80(11): 5199-5210.
Grifman, et al., "Incorporation of tumor-targeting peptides into recombinant adeno-associated virus capsids". Molecular Therapy (2001); vol. 3, No. 6, pp. 964-975.
Grimm, et al., "In Vitro and in Vivo Gene Therapy Vector Evolution via Multispecies Interbreeding and Retargeting of Adeno-Associated Viruses." Journal of Virology; vol. 82, No. 12, pp. 5887-5911 (Jun. 2008).
Groth, Amy C., et al. "A phage integrase directs efficient site-specific integration in human cells." Proc Natl Acad Sci U S A. (2000); 97.11: 5995-6000.

Gunther, Karen L., et al. "A novel mutation in the short-wavelength-sensitive cone pigment gene associated with a tritan color vision defect." Visual Neuroscience (2006); 23.3-4: 403-409.
Halbert, et al., "Repeat transduction in the mouse lung by using adeno-associated virus vectors with different serotypes." J. Virol.; vol. 74, No. 3, pp. 1524-1532 (Feb. 2000).
Hasumi, et al., "Soluble FLT-1 expression suppresses carcinomatous ascites in nude mice bearing ovarian cancer." Cancer Res. 2002; 62(7): 2019-2023.
Hauswirth, et al., "Treatment of leber congenital amaurosis due to RPE65 mutations by ocular subretinal injection of adena-associated virus gene vector: short-term results of a phase I trial." Hum Gene Ther. 2008; 19(10): 979-990.
He, et al., "Alternative splicing of vascular endothelial growth factor (VEGF)-R1 (FLT-1) pre-mRNA is important for the regulation of VEGF activity." Mol Endocrinol. 1999; 13(4): 537-545.
Heinis, Christian, and Johnsson, Kai. "Using peptide loop insertion mutagenesis for the evolution of proteins." Methods Mol Biol. (2010); 634: 217-232.
Hellström, et al., "Cellular tropism and transduction properties of seven adeno-associated viral vector serotypes in adult retina after intravitreal injection." Gene Therapy (2009); 16: 521-532.
Hirsch, et al., "Directed Evolution of the AVV Capsid for Human Embryonic Stem Cell Transduction." Molecular Therapy; vol. 17, Supp. 1, S177-S178 (May 2009), 2 pages.
Hoess, R.H. et al. "The role of the loxP spacer region in P1 site-specific recombination." Nucleic Acids Research (1986); 14.5: 2287-2300.
Hoffman, et al., "Cell-mediated immune response and stability of intraocular transgene expression after adenovirus-mediated delivery." Invest Ophthalmol Vis Sci. 1997; 38(11): 2224-2233.
Honda, et al., "Experimental subretinal neovascularization is inhibited by adenovirus-mediated soluble VEGF/flt-1 receptor gene transfection: a role of VEGF and possible treatment for SRN in age-related macular degeneration." Gene Ther. 2000; 7(11): 978-985.
Hu, et al., "Design of retroviral vectors and helper cells for gene therapy." Pharmacol Rev. 2000; 52(4): 493-511.
Huang, et al., "Innate immune recognition of viruses and viral vectors." Hum Gene Ther. 2009; 20(4): 293-301.
Huttner, et al., "Genetic Modifications of the Adena-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002), 2 pgs.
Huttner, et al., "Genetic modifications of the adeno-associated virus type 2 capsid reduce the affinity and the neutralizing effects of human serum antibodies." Gene Ther; vol. 10, No. 26, pp. 2139-2147 (Dec. 2003).
Ibrahim, et al., "Heat shock and arsenite induce expression of the nonclassical class I histocompatibility HLA-G gene in tumor cell lines." Cell Stress Chaperones. 2000; 5(3): 207-218.
International Preliminary Report on Patentability for International Application No. PCT/US2010/048964, dated Mar. 20, 2012, 14 pages.
International Preliminary Report on Patentability for International Application No. PCT/US2013/040011, dated Nov. 18, 2014, 48 pages.
International Preliminary Report on Patentability for International Application No. PCT/US2013/045043, dated Dec. 16, 2014, 9 pages.
International Preliminary Report on Patentability for International Application No. PCT/US2015/021087, dated Sep. 20, 2016, 8 pages.
International Preliminary Report on Patentability for International Application No. PCT/US2016/068312, dated Jun. 26, 2018, 12 pages.
International Search Report and Written Opinion for International Application No. PCT/US2010/048964, dated Jun. 17, 2011, 23 pages.
International Search Report and Written Opinion for International Application No. PCT/US2013/040011, dated Dec. 17, 2013, 57 pages.

(56) References Cited

OTHER PUBLICATIONS

International Search Report and Written Opinion for International Application No. PCT/US2013/045043, dated Nov. 12, 2013, 11 pages.
International Search Report and Written Opinion for International Application No. PCT/US2015/021087, dated Aug. 12, 2015, 12 pages.
International Search Report and Written Opinion for International Application No. PCT/US2016/020482, dated Aug. 8, 2016, 12 pages.
International Search Report and Written Opinion for International Application No. PCT/US2016/068312, dated May 3, 2017, 22 pages.
Invitation to Pay Additional Fees for International Application No. PCT/US2015/021087, dated Jun. 18, 2015, 3 pages.
Invitation to Pay Additional Fees for International Application No. PCT/US2016/020482, dated May 6, 2016, 3 pages.
Jacobs, Gerald H. "A perspective on color vision in platyrrhine monkeys." Vision Research (1998); 38.21: 3307-3313.
Jacobs, Gerald H., et al. "Emergence of novel color vision in mice engineered to express a human cone photopigment." Science (2007); 315.5819: 1723-1725.
Jacobson, et al., "Gene therapy for leber congenital amaurosis caused by RPE65 mutations: safety and efficacy in 15 children and adults followed up to 3 years." Arch Ophthalmol. (2012); 130(1): 9-24.
Jacobson, et al., "Safety in nonhuman primates of ocular AAV2-RPE65, a candidate treatment for blindness in Leber congenital amaurosis." Hum Gene Ther. 2006; 17(8): 845-858.
Jacobson, et al., "Safety of recombinant adeno-associated virus type 2-RPE65 vector delivered by ocular subretinal injection", Mol Ther. (2006); 13(6):1074-1084.
Jang, et al., "An evolved adeno-associated viral variant enhances gene delivery and gene targeting in neural stem cells." Mol Ther. (Apr. 2011); 19(4): 667-675.
Johnson-Saliba and Jans, "Gene Therapy: Optimising DNA Delivery to the Nucleus", Curr. Drug. Targets 2001; 2(4): 371-399.
Kaplitt, et al., "Long-term gene expression and phenotypic correction using adeno associated virus vectors in the mammalian brain." Nat Genet. 1994; 8(2):148-154.
Karp, et al., "An in vitro model of differentiated human airway epithelia. Methods for establishing primary cultures." Methods Mol Biol.; vol. 188, pp. 115-137 (2002).
Kendall, et al., "Identification of a natural soluble form of the vascular endothelial growth factor receptor, FLT-1, and its heterodimerization with KDR." Biochem Biophys Res Commun. 1996; 226(2): 324-328.
Kendall, et al., "Inhibition of vascular endothelial cell growth factor activity by an endogenously encoded soluble receptor." Proc Natl Acad Sci USA. 1993; 90(22):10705-10709.
Kern, et al., "Identification of a heparin-binding motif on adeno-associated virus type 2 capsids." Journal of Virology; vol. 77, No. 20, pp. 11072-11081 (Oct. 2003).
Khaliq, et al., "Increased expression of placenta growth factor in proliferative diabetic retinopathy." Lab Invest. 1998; 78(1): 109-116.
Khani, et al., "AAV-mediated expression targeting of rod and cone photoreceptors with a human rhodopsin kinase promoter." Investigative Ophthalmology & Visual Science. 2007; 48(9): 3954-3961.
Kiang, et al., "Cytoprotection and regulation of heat shock proteins induced by heat shock in human breast cancer T47-D cells: role of [Ca2+]i and protein kinases." FASEB J. 1998; 12(14): 1571-1579.
Klein, et al., "Fifteen-year cumulative incidence of age-related macular degeneration: the Beaver Dam Eye Study." Ophthalmology. 2007; 114(2): 253-262.
Klein, et al., "The relation of cardiovascular disease and its risk factors to the 5-year incidence of age-related maculopathy: the Beaver Dam Eye Study." Ophthalmology. 1997; 104(11): 1804-1812.
Kliffen, et al., "Increased expression of angiogenic growth factors in age-related maculopathy." Br J Ophthalmol. 1997; 81(2): 154-162.
Klimczak, et al., "A novel adeno-associated viral variant for efficient and selective intravitreal transduction of rat muller cells." PLoS One (Oct. 2009); 4(10): e7467.
Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 117 pages (2010).
Koerber, et al., "DNA Shuffling of Adeno-associated Virus Yields Functionally Diverse Viral Progeny." Mol Ther. (Oct. 2008); 16(10): 1703-1709. Epub Aug. 6, 2008.
Koerber, et al., "Engineering of a Novel AVV Vector in a Human Airway Model System for Cystic Fibrosis Gene Therapy"; AIChE Annual Meeting Abstract, 3 pages (Nov. 29, 2008).
Koerber, et al., "Molecular evolution of adeno-associated virus for enhanced glial gene delivery." Molecular Therapy (2009); vol. 17, No. 12, pp. 2088-2095.
Komáromy, András M., et al. "Gene therapy rescues cone function in congenital achromatopsia." Human Molecular Genetics (Jul. 2010); 19(13): 2581-2593. Epub Apr. 8, 2010.
Komaromy, et al., "Targeting gene expression to cones with human cone opsin promoters in recombinant AAV." Gene Ther. 2008; 15(14): 1049-1055.
Kong, et al., "Regional suppression of tumor growth by in vivo transfer of a cDNA encoding a secreted form of the extracellular domain of the flt-1 vascular endothelial growth factor receptor." Hum Gene Ther. 1998; 9(6): 823-833.
Kotterman and Schaffer, "Engineering adeno-associated viruses for clinical gene therapy." Nat Rev Genet. (Jul. 2014); 15(7): 445-451. Epub May 20, 2014.
Kozak, "Point mutations define a sequence flanking the AUG initiator codon that modulates translation by eukaryotic ribosomes", Cell (1986); 44(2): 283-292 (Abstract Only).
Krysiak, et al., "Soluble vascular endothelial growth factor receptor-1 (sFLT-1) mediates downregulation of FLT-1 and prevents activated neutrophils from women with preeclampsia from additional migration by VEGF." Circ Res. 2005; 97(12): 1253-1261.
Krzystolik, et al., "Prevention of experimental choroidal neovascularization with intravitreal anti-vascular endothelial growth factor antibody fragment." Arch Ophthalmol. 2002; 120(3):338-346.
Kuchenbecker, James A., et al. "Topography of the long-to middle-wavelength sensitive cone ratio in the human retina assessed with a wide-field color multifocal electroretinogram." Visual Neuroscience (2008); 25.03: 301-306.
Kvanta, et al., "Subfoveal fibrovascular membranes in age-related macular degeneration express vascular endothelial growth factor." Invest Ophthalmol Vis Sci. 1996; 37(9): 1929-1934.
Kvaratskhelia, Mamuka, et al. "Molecular mechanisms of retroviral integration site selection." Nucleic Acids Research (2014); 42.16: 10209-10225.
Kwak, et al., "VEGF is major stimulator in model of choroidal neovascularization." Invest Ophthalmol Vis Sci. 2000; 41(10): 3158-3164.
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lai, et al., "Generation of transgenic mice with mild and severe retinal neovascularisation." Br J Ophthalmol. 2005; 89(7): 911-916.
Lai, et al., "Inhibition of angiogenesis by adenovirus-mediated sFlt-1 expression in a rat model of corneal neovascularization." Hum Gene Ther. 2001; 12(10): 1299-1310.
Lai, et al., "Potential long-term inhibition of ocular neovascularisation by recombinant adeno-associated virus-mediated secretion gene therapy." Gene Ther. 2002; 9(12): 804-813.
Lai, et al., "Preclinical safety evaluation of subretinal AAV2.sFlt-1 in non-human primates." Gene Ther. 2012; 19(10): 999-1009. Epub Nov. 10, 2011.

(56) References Cited

OTHER PUBLICATIONS

Lai, et al., "rAAV.sFlt-1 Gene Therapy Achieves Lasting Reversal of Retinal Neovascularization in the Absence of a Strong Immune Response to the Viral Vector." Invest Ophthalmol Vis Sci. 2009; 50(9): 4279-4287.
Lai, et al., "Recombinant adena-associated virus type 2-mediated gene delivery into the Rpe65-/- knockout mouse eye results in limited rescue." Genet Vaccines Ther. 2004; 2:3, 15 pages.
Lai, et al., "Long-term evaluation of AAV-mediated sFlt-1 gene therapy for ocular neovascularization in mice and monkeys." Mol Ther. (Oct. 2005); 12(4): 659-668.
Lai, Timothy YY, et al. "The clinical applications of multifocal electroretinography: a systematic review." Survey of Ophthalmology (2007); 52.1: 61-96.
Lalwani, et al., "A variable-dosing regimen with intravitreal ranibizumab for neovascular age-related macular degeneration: year 2 of the PrONTO Study." Am J Ophthalmol. 2009; 148(1): 43-58.
Langer, Stephen J., et al. "A genetic screen identifies novel non-compatible loxP sites." Nucleic Acids Research (2002); 30.14: 3067-3077.
Lavinksy, D. et al., "Modulation of transgene expression in retinal gene therapy by selective laser treatment." Investigative Ophthalmology & Visual Science. 2013; 54(3): 1873-1880.
Le Gal La Salle, et al., "An adenovirus vector for gene transfer into neurons and glia in the brain." Science. 1993; 259(5097): 988-990.
Le Meur, et al., "Postsurgical assessment and long-term safety of recombinant adeno-associated virus-mediated gene transfer into the retinas of dogs and primates." Arch Ophthalmol. 2005; 123(4): 500-506.
Le Meur, et al., "Restoration of vision in RPE65-deficient Briard dogs using an AAV serotype 4 vector that specifically targets the retinal pigmented epithelium." Gene Ther. 2007; 14(4): 292-303.
Lebherz, et al., "Novel AAV serotypes for improved ocular gene transfer." J Gene Med. 2008; 10(4): 375-382.
Lee, Gwang, and Saito, Izumu. "Role of nucleotide sequences of loxP spacer region in Cre-mediated recombination." Gene (1998); 216.1: 55-65.
Levine, et al., "Circulating angiogenic factors and the risk of preeclampsia." N Engl J Med. 2004; 350(7): 672-683.
Li, et al., "Gene therapy following subretinal AAV5 vector delivery is not affected by a previous intravitreal AAV5 vector administration in the partner eye." Mol Vis. 2009; 15: 267-275.
Li, et al., "Intraocular route of AAV2 vector administration defines humoral immune response and therapeutic potential." Mol Vis. 2008; 14: 1760-1769.
Li, et al., "Cone-specific expression using a human red opsin promoter in recombinant AAV." Vision Res. 2008; 48(3): 332-338.
Li, et al., "Engineering and Selection of Shuffled AAV Genomes: A New Strategy for Producing Targeted Biological Nanoparticles." Molecular Therapy; vol. 15, No. 7, pp. 1252-1260 (Jul. 2008).
Lieber, et al., "Integrating adenovirus-adena-associated virus hybrid vectors devoid of all viral genes." J Virol. 1999; 73(11): 9314-9324.
Limberis, et al., "Adeno-associated virus serotype 9 vectors transduce murine alveolar and nasal epithelia and can be readministered." (and Correction) Proc Natl Acad Sci USA; vol. 103, No. 35, pp. 12993-12998 (Aug. 29, 2006).
Lindenberg, Thomas, et al. "Cyclic summation versus m-sequence technique in the multifocal ERG." Graefe's Archive for Clinical and Experimental Ophthalmology (2003); 241.6: 505-510.
Liu, et al., "Soluble Fms-like tyrosine kinase-1 expression inhibits the growth of multiple myeloma in nude mice." Acta Biochim Biophys Sin (Shanghai). 2007; 39(7): 499-506.
Liu, et al., "Gene therapy for ocular diseases." Br J Ophthalmol. 2011; 95(5): 604-612.
Liu, Xiaomei, Han Ping, and Chun Zhang. "Rapid establishment of a HEK 293 cell line expressing FVIII-BDD using AVV site-specific integration plasmids." BMC Research Notes (2014); 7: 626, 6 pages.
Loiler, et al., "Targeting recombinant adeno-associated virus vectors to enhance gene transfer to pancreatic islets and liver." Gene Ther.; vol. 10, pp. 1551-1558 (2003).
Lopez, et al., "Transdifferentiated retinal pigment epithelial cells are immunoreactive for vascular endothelial growth factor in surgically excised age-related macular degeneration-related choroidal neovascular membranes." Invest Ophthalmol Vis Sci. 1996; 37(5): 855-868.
Lu, et al., "Complete correction of hemophilia A with adeno-associated viral vectors containing a full-size expression cassette." Hum Gene Ther. (2008); 19(6):648-654. doi: 10.1089/hum.2007.0182.
Lukason, et al., "Inhibition of choroidal neovascularization in a nonhuman primate model by intravitreal administration of an AAV2 vector expressing a novel anti-VEGF molecule." Mol Ther. (Feb. 2011); 19(2): 260-265. Epub Oct. 26, 2010.
Lundstrom, "Alphavirus vectors: applications for DNA vaccine production and gene expression." Intervirology. 2000; 43(4-6): 247-257.
Luo and Saltzman, "Synthetic DNA delivery systems", Nature Biotechnol. 2000; 18(1): 33-37.
Luthert, et al., "Photoreceptor rescue." Eye (Lond). 1998; 12(Pt 3b): 591-596.
MacLachlan, et al., "Preclinical safety evaluation of AAV2-sFLT01—a gene therapy for age-related macular degeneration." Mol Ther. 2011; 19(2): 326-334. Epub Nov. 30, 2010.
Mae, et al., "Gene transfer of the vascular endothelial growth factor receptor flt-1 suppresses pulmonary metastasis associated with lung growth." Am J Respir Cell Mol Biol. 2005; 33(6): 629-635.
Maguire, et al., "Age-dependent effects of RPE65 gene therapy for Leber's congenital amaurosis: a phase 1 dose-escalation trial." Lancet. 2009; 374(9701): 1597-1605.
Maguire, et al., "Directed evolution of adeno-associated virus for glioma cell transduction." J. Neurooncol.; vol. 96, pp. 337-347 (2010).
Maguire, et al., "Safety and efficacy of gene transfer for Leber's congenital amaurosis." N Engl J Med. 2008; 358(21): 2240-2248.
Mahasreshti, et al., "Adenovirus-mediated soluble FLT-1 gene therapy for ovarian carcinoma." Clin Cancer Res. 2001; 7(7): 2057-2066.
Mahasreshti, et al., "Intravenous delivery of adenovirus-mediated soluble FLT-1 results in liver toxicity." Clin Cancer Res. 2003; 9(7): 2701-2710.
Maheshri, Narendra, et al. "Directed evolution of adeno-associated virus yields enhanced gene delivery vectors." Nature Biotechnology (2006); 24.2: 198-204.
Makous, Walter. "Comment on "emergence of novel color vision in mice engineered to express a human cone photopigment"." Science (2007); 318.5848: 196b-196b.
Malamos, et al., "Correlation of high-definition optical coherence tomography and fluorescein angiography imaging in neovascular macular degeneration." Invest. Ophthalmol Vis Sci. 2009; 50(10): 4926-4933.
Mancuso et al., "Gene therapy treatment of color blindness in adult primates." Journal of Vision (2007); 7(15): 15a. (Abstract).
Mancuso, et al., "Colorblindness Cure: Gene Therapy Confers a New Sensation", Investigative Opthamology & Visual Science (2008), 49: E-Abstract 3252 (Meeting Abstract).
Mancuso, et al., "Recombinant adena-associated virus targets passenger gene expression to cones in primate retina", Journal of the Optical Society of America A (2007); 24(5): 1411-1416.
Mancuso, K., et al. "Progress in Developing a Gene Therapy Approach for Treating Color Blindness." Investigative Ophthalmology & Visual Science 46.13 (2005): 4565-4565 & 2005 Annual Meeting of the Association for Research in Vision and Ophthalmology, FL. Lauderdale, FL, 46(Supp S): 4565 (2005).
Mancuso, Katherine, et al. "An adaptation of the Cambridge Colour Test for use with animals." Visual Neuroscience (2006); 23.3-4: 695-701.
Mancuso, Katherine, et al. "Gene therapy for red-green colour blindness in adult primates." Nature (2009); 461.7265: 784-787.
Manno, et al., "Successful transduction of liver in hemophilia by AVV-Factor IX and limitations imposed by the host immune response." Nat Med. 2006; 12(3): 342-347.

(56) References Cited

OTHER PUBLICATIONS

Mao, Yanxiong, et al. "Persistent Suppression of Ocular Neovascularization with Intravitreal Administration of AAVrh.10 Coding for Bevacizumab." Human Gene Therapy (2011); 22(12): 1525-1535.
Martin et al., "Gene delivery to the eye using adeno-associated viral vectors", Methods (2002); 28: 267-275.
Mauck, et al., "Longitudinal in vivo Characterization of Expression of Viral Delivered Genes for L-opsin and Green Fluorescent Protein in Cone Photoreceptors of Gerbils." Investigative Ophthalmology & Visual Science (2006); 47.13: 4071-4071.
Mauck, Matthew C., et al. "Longitudinal evaluation of expression of virally delivered transgenes in gerbil cone photoreceptors." Visual Neuroscience (2008); 25(3): 273-282.
Maynard, et al., "Excess placental soluble fms-like tyrosine kinase 1 (sFlt1) may contribute to endothelial dysfunction, hypertension, and proteinuria in preeclampsia." J Clin Invest. 2003; 111(5): 649-658.
McCullum, et al., "Random Mutagenesis by Error-Prone PCR." Jeff Braman (ed.), In Vitro Mutagenesis Protocols: Third Edition, Methods in Molecular Biology (2010); vol. 634, pp. 103-109.
McGee Sanftner, et al., "Glial Cell Line Derived Neurotrophic Factor Delays Photoreceptor in a Transgenic Rat Model of Retinitis Pigmentosa." Molecular Therapy; vol. 4, No. 6, pp. 622-629 (Dec. 2001).
McLeod, Maureen, et al. "Identification of the crossover site during FLP-mediated recombination in the *Saccharomyces cerevisiae* plasmid 2 microns circle." Molecular and Cellular Biology (1986); 6.10: 3357-3367.
Merigan, et al., "Tracking Transfection of Macaque Retinal Ganglion Cells With AAV2 Viral Vectors; In vivo Imaging Reveals Differences Between Two Promoters." ARVO Annual Meeting Abstract (May 2008); Investigative Ophthalmology & Visual Science. 2008; vol. 49: 4514.
Michel, et al., "Stress-induced transcription of the clusterin/apoJ gene." Biochem J. 1997; 328 ( Pt 1): 45-50.
Michelfelder, et al., "Successful Expansion but Not Complete Restriction of Tropism of Adeno-Associated Virus by In Vivo Biopanning of Random Virus Display Peptide Libraries." PLoS One; vol. 4, No. 4, pp. 1-13 (Apr. 2009).
Michelfelder, et al., "Vectors selected from adeno-associated viral display peptide libraries for leukemia cell-targeted cytotoxic gene therapy." Experimental Hematology; vol. 35, pp. 1766-1776 (2007).
Miller, et al., "Human effector and memory CD8+ T cell responses to smallpox and yellow fever vaccines." Immunity. 2008; 28(5): 710-722.
Mitchell, et al., "Cost effectiveness of treatments for wet age-related macular degeneration." PharmacoEconomics 2011; 29(2): 107-131.
Mitchell, et al., "Ranibizumab (Lucentis) in neovascular age-related macular degeneration: evidence from clinical trials." Br J Ophthalmol. 2010; 94(1): 2-13.
Mitchell, et al., "AAV's anatomy: Roadmap for optimizing vectors for translational success." Curr Gene Ther. (2010); vol. 10, No. 5, pp. 319-340.
Miyamoto, et al., "Prevention of leukostasis and vascular leakage in streptozotocininduced diabetic retinopathy via intercellular adhesion molecule-1 inhibition." Proc Natl Acad Sci USA. 1999; 96(19): 10836-10841.
Miyoshi, et al., "Development of a self-inactivating lentivirus vector." J Virol. 1998; 72(10): 8150-8157.
Moskalenko, et al., "Epitope mapping of human anti-adeno-associated virus type 2 neutralizing antibodies: Implications for gene therapy and virus structure." J. Virol.; vol. 74, No. 4, pp. 1761-1766 (Feb. 2000).
Müller, et al., "Random peptide libraries displayed on adeno-associated virus to select for targeted gene therapy vectors." Nature Biotechnology (2003); 21.9: 1040-1046.
Nakai, et al., "AAV serotype 2 vectors preferentially integrate into active genes in mice." Nature Genetics (2003); 34 (3): 297-302.
Naldini, L., et al., "Efficient transfer, integration, and sustained long-term expression of the transgene in adult rat brains injected with a lentiviral vector." Proc. Natl. Acad. Sci. USA (1996), 93(21): 11382-11388.
Naldini, L., et al., "In vivo gene delivery and stable transduction of nondividing cells by a lentiviral vector." Science (1996), 272(5259): 263-267.
Naldini, L., et al., "Lentiviruses as gene transfer agents for delivery to non-dividing cells." Curr Opin Biotechnol. (1998), 5: 457-463.
Narfstrom, et al., "Assessment of structure and function over a 3-year period after gene transfer in RPE65-/-dogs." Doc Ophthalmol. 2005; 111(1): 39-48.
Narfstrom, et al., "Functional and structural recovery of the retina after gene therapy in the RPE65 null mutation dog." Invest Ophthalmol Vis Sci. 2003; 44(4):1663-1672.
Narfstrom, et al., "In vivo gene therapy in young and adult RPE65-/-dogs produces long-term visual improvement." J Hered. 2003; 94(1): 31-37.
Nathans, et al., "Molecular genetics of human blue cone monochromacy." Science. 1989; 245(4920): 831-838.
Nathans, J., et al. "Molecular genetics of human color vision: the genes encoding blue, green, and red pigments." Science (1986); 232(4747): 193-202.
Nathans, Jeremy, et al. "Molecular genetics of inherited variation in human color vision." Science (1986); 232.4747: 203-210.
Neitz, Maureen, et al. "Spectral tuning of pigments underlying red-green color vision." Science (1991); 252.5008: 971-974.
Nemerow, "A new link between virus cell entry and inflammation: adenovirus interaction with integrins induces specific pro inflammatory responses." Mol Ther. 2009; 17(9): 1490-1491.
Neufeld, et al., "Vascular endothelial growth factor (VEGF) and its receptors." FASEB J. 1999; 13(1): 9-22.
Nguyen, et al.,"Convection-enhanced delivery of AAV-2 combined with heparin increases TK gene transfer in the rat brain." Neuroreport; vol. 12, No. 9, pp. 1961-1964 (Jul. 3, 2001).
Nicklin, et al., "Efficient and selective AAV2-mediated gene transfer directed to human vascular endothelial cells." Molecular Therapy (2001); vol. 4, No. 2, pp. 174-181.
Niederkorn, et al., "See no evil, hear no evil, do no evil: the lessons of immune privilege." Nat Immunol. 2006; 7(4): 354-359.
Nork, et al., "Prevention of Experimental Choroidal Neovascularization and Resolution of Active Lesions by VEGF Trap in Nonhuman Primates." Archives of Ophthalmology (2011); 129 (8): 1042-1052.
Novartis, Application for inclusion in the WHO Essential Medicines List, Section 21, Ophthalmological Preparations Ranibizumab (Lucentis®)—Addition. Webpage [online]. Nov. 28, 2014; Retrieved from the Internet: <URL:http://www.selleckchem.com/products/lmk-235.html>; 49 pages.
Ohno-Matsui, et al., "Novel mechanism for age-related macular degeneration: an equilibrium shift between the angiogenesis factors VEGF and PEDF." J Cell Physiol. 2001; 189(3): 323-333.
Oikawa, et al., "Three novel synthetic retinoids, Re 80, Am 580 and Am 80, all exhibit anti-angiogenic activity in vivo." Eur J Pharmacol. 1993; 249(1): 113-116.
Opie, et al., "Identification of Amino Acid Residues in the Capsid Proteins of Adeno-Associated Virus Type 2 that Contribute to Heparan Sulfate Proteoglycan Binding." Journal of Virology; vol. 77, No. 12, pp. 6995-7006 (Jun. 2003).
Paddison, et al., "Stable suppression of gene expression by RNAi in mammalian cells." Proc. Nat'l Acad. Sci. USA; vol. 99, No. 3, pp. 1443-1448 (Feb. 5, 2002).
Padron, et al., "Structure of adeno-associated virus type 4." Journal of Virology (2005); 79(8): 5047-5058.
Palu et al., "In pursuit of new developments for gene therapy of human diseases", J. of Biotechnology. 1999; 68: 1-13.
Pang, Ji-jing, et al. "Gene therapy restores vision-dependent behavior as well as retinal structure and function in a mouse model of RPE65 Leber congenital amaurosis." Molecular Therapy (2006); 13.3: 565-572.
Papadakis et al. "Promoters and Control Elements: Designing Expression Cassettes for Gene Therapy." Current Gene Therapy (2004); 4(1): 89-113.

(56) References Cited

OTHER PUBLICATIONS

Park, et al., "The fourth immunoglobulin-like loop in the extracellular domain of FLT- 1, a VEGF receptor, includes a major heparin-binding site." Biochem Biophys Res. Commun. 1999; 264(3): 730-734.
Park, et al., "Intravitreal delivery of AAV8 retinoschisin results in cell type-specific gene expression and retinal rescue in the Rs1-KO mouse." Gene Therapy (2009); 16(7): 916-926.
Paulus, et al., "Selective retinal therapy with microsecond exposures using a continuous line scanning laser." Retina. 2011 ; 31(2): 380-388.
Pechan, et al., "Novel anti-VEGF chimeric molecules delivered by AAV vectors for inhibition of retinal neovascularization", Gene Ther. (2009); 16(1): 10-16.
Perabo, et al., "In Vitro Selection of Viral Vectors with Modified Tropism: The Adena-associated Virus Display." Molecular Therapy; vol. 8, No. 1, pp. 151-157 (Jul. 2003).
Perabo, et al., "Combinatorial engineering of a gene therapy vector: directed evolution of adeno-associated virus." The Journal of Gene Medicine (2006); vol. 8, pp. 155-162.
Perabo, et al., "Heparan Sulfate Proteoglycan Binding Properties of Adeno-Associated Virus Retargeting Mutants and Consequences for Their In Vitro Tropism." Journal of Virology; vol. 80, No. 14, pp. 7265-7269 (Jul. 2006).
Perri, et al., "Replicon vectors derived from Sindbis virus and Semliki forest virus that establish persistent replication in host cells." J Virol. 2000; 74(20): 9802-9807.
Petrs-Silva, et al., "High-efficiency transduction of the mouse retina by tyrosine-mutant AAV serotype vectors." Molecular Therapy (2009); 17(3): 463-471.
Petrs-Silva, et al., "Novel properties of tyrosine-mutant AAV2 vectors in the mouse retina." Mol Ther. (Feb. 2001); 19(2): 293-301.
Pfeifer and Verma, "Gene Therapy: Promises and Problems", Annu. Rev. Genomics. Hum. Genet. 2001; 2: 177-211.
Pieramici, et al., "Age-related macular degeneration and risk factors for the development of choroidal neovascularization in the fellow eye." Curr Opin Ophthalmol. 1998; 9(3): 38-46.
Pitcher, et al., "Development and homeostasis of T cell memory in rhesus macaque." J Immunol. 2002; 168(1): 29-43.
Pollock, et al., "Delivery of a stringent dimerizer-regulated gene expression system in a single retroviral vector." Proceedings of the National Academy of Sciences of the United States of America. 2000; 97(24): 13221-6.
Provost, et al., "Biodistribution of rAAV vectors following intraocular administration: evidence for the presence and persistence of vector DNA in the optic nerve and in the brain." Mol Ther. 2005; 11(2): 275-83.
Pshenichkin, et al., "Heat shock enhances CMV-IE promoter-driven metabotropic glutamate receptor expression and toxicity in transfected cells." Neuropharmacology. 2011; 60: 1292-1300.
Quantin, et al., "Adenovirus as an expression vector in muscle cells in vivo." Proc Natl Acad Sci USA. 1992; 89(7): 2581-2584.
Rabinowitz, et al., "Building a Better Vector: The Manipulation of AAV Virions." Virology; vol. 278, pp. 301-308 (2000).
Rabinowitz, et al.,"Insertional mutagenesis of AAV2 capsid and the production of recombinant virus." Virology; vol. 265, No. 2, pp. 274-285 (Dec. 20, 1999).
Rapti, Kleopatra, et al. "Neutralizing antibodies against AAV serotypes 1, 2, 6, and 9 in sera of commonly used animal models." Molecular Therapy (2012); 20.1: 73-83.
Recchia, Alessandra, et al. "Site-specific integration of functional transgenes into the human genome by adeno/AAV hybrid vectors." Molecular Therapy (2004); 10.4: 660-670.
Reffin, J. P., et al. "Trials of a computer-controlled colour vision test that preserves the advantages of pseudoisochromatic plates." Colour Vision Deficiencies X. Springer Netherlands (1991); pp. 69-76.
Regan, Benedict C., et al. "Luminance noise and the rapid determination of discrimination ellipses in colour deficiency." Vision Research (1994); 34.10: 1279-1299.
Regeneron press release, Bayer and Regeneron Report Positive Top-Line Results of Two Phase 3 Studies with VEGF Trap-Eye in Wet Age-related Macular Degeneration. Nov. 22, 2010. http://newsroom.regeneron.com/releasedetail.cfm?ReleaseiD=532099 (last accessed Nov. 24, 2010).
Regillo, et al., "Randomized, double-masked, sham-controlled trial of ranibizumab for neovascular age-related macular degeneration: PIER Study year 1." Am J Ophthalmol. 2008; 145(2): 239-248.
Rein, et al., "Forecasting age-related macular degeneration through the year 2050: the potential impact of new treatments." Arch Ophthalmol. 2009; 127(4): 533-540.
Response to request under 27 CFR 1.1 05, dated Apr. 27, 2015, in U.S. Appl. No. 10/075,415, pp. 8-10 (3 pages).
Ried, et al., "Adeno-associated virus capsids displaying immunoglobulin-binding domains permit anitbody-mediated vector retargeting to specific cell surface receptors." J. Virol.; vol. 76, No. 9, pp. 4559-4566 (May 2002).
Roberts, et al., "Pathogenesis and genetics of pre-eclampsia." Lancet. 2001; 357(9249): 53-56.
Robinson, et al., "The splice variants of vascular endothelial growth factor (VEGF) and their receptors." J Cell Sci. 2001; 114(Pt 5): 853-865.
Rolling, et al., "Long-term real-time monitoring of adena-associated virus-mediated gene expression in the rat retina." Clin Experiment Ophthalmol. 2000; 28(5): 382-386.
Romano, et al., "Latest developments in gene transfer technology: achievements, perspectives, and controversies over therapeutic applications." Stem Cells. 2000; 18(1): 19-39.
Rome, C., et al., "Spatial and temporal control of expression of therapeutic genes using heat shock protein promoters." Methods (2005); 35.2: 188-198.
Rosenfeld, et al., "In vivo transfer of the human cystic fibrosis transmembrane conductance regulator gene to the airway epithelium." Cell. 1992; 68(1): 143-155.
Rosenfeld, et al., "Ranibizumab for neovascular age-related macular degeneration." N Engl J Med. 2006; 355(14): 1419-1431.
Ryals, et al., "Quantifying transduction efficiencies of unmodified and tyrosine capsid mutant AAV vectors in vitro using two ocular cell lines." Mol Vision (Apr. 2011); 7: 1090-1102.
Saishin, et al., "VEGF-TRAP(R1R2) suppresses choroidal neovascularization and VEGF-induced breakdown of the blood-retinal barrier." J Cell Physiol. 2003; 195(2): 241-248.
Salam, et al., "Treatment of proliferative diabetic retinopathy with anti-VEGF agents." Acta Ophthalmol. 2011; 89(5): 405-411.
Samulski, et al., "Helper-Free Stocks of Recombinant Adeno-Associated Viruses: Normal Integration Does Not Require Viral Gene Expression." Journal of Virology (1989); 63.9: 3822-3828.
Sauer, Brian, "Site-specific recombination: developments and applications." Current Opinion in Biotechnology (1994); 5.5: 521-527.
Schaffer, et al.; "Directed evolution of AAV vector mutants for enhanced gene delivery"; Abstracts of Papers American Chemical Society; vol. 227, Part 1, Abstract 172, p. U214 (Mar. 28-Apr. 1, 2004), 2 pages.
Schlake, Thomas, and Bode, Juergen, "Use of mutated FLP recognition target (FRT) sites for the exchange of expression cassettes at defined chromosomal loci." Biochemistry (1994); 33.43: 12746-12751.
Schmidt, Michael, et al., "Adeno-associated virus type 2 Rep78 induces apoptosis through caspase activation independently of p53." Journal of Virology (2000); 74.20: 9441-9450.
Schmidt-Erfurth, "Clinical safety of ranibizumab in age-related macular degeneration." Expert Opin Drug Saf. 2010; 9(1):149-165.
Schmidt-Erfurth, et al., "Efficacy and safety of monthly versus quarterly ranibizumab treatment in neovascular age-related macular degeneration: the EXCITE study." Ophthalmology. 2011; 118(5): 831-839.
Schuele, et al., "RPE damage thresholds and mechanisms for laser exposure in the microsecond-to-millisecond time regimen." Invest Ophthalmol Vis Sci. 2005; 46: 714-719.
Schwartz, et al., "Embryonic stem cell trials for macular degeneration: a preliminary report." Lancet. 2012; 379(9817): 713-720.
Score Search Result 33 for Arbetman et al WO2004112727-A2, Dec. 29, 2004, 3 pages.

(56) References Cited

OTHER PUBLICATIONS

Search Report (English translation) in Chinese Application No. 2013800375773, dated Nov. 24, 2016, 2 pages.
Search result 9, run by the STIC search facility, 2016, 2 pages.
Seddon, et al., "Validation of a prediction algorithm for progression to advanced macular degeneration subtypes." JAMA Ophthalmol. 2013; 131(4): 448-455.
Senecoff, Julie F., et al., "DNA recognition by the FLP recombinase of the yeast 2 μ plasmid: a mutational analysis of the FLP binding site." Journal of Molecular Biology (1988); 201.2: 405-421.
Shaaban, Salam A., et al. "Transgenic mice expressing a functional human photopigment." Investigative Ophthalmology & Visual Science (1998); 39.6: 1036-1043.
Shah et al., "Outcomes and risk factors associated with endophthalmitis after intravitreal injection of anti-vascular endothelial growth factor agents." Jefferson Digital Commons. 2011; pp. 1-14.
Shapley, Robert. "Specificity of cone connections in the retina and color vision. Focus on "specificity of cone inputs to macaque retinal ganglion cells"." Journal of Neurophysiology (2006); 95.2: 587-588.
Shen, et al., "Multiple roles for sialylated glycans in determining the cardiopulmonary tropism of adeno-associated virus 4." J Virol. (Dec. 2013); 87(24): 13206-13213. Epub Sep. 25, 2013.
Shen, et al., "Characterization of the relationship of AAV capsid domain swapping to liver transduction efficiency." Mol Ther. (2007); 15(11): 1955-1962.
Sheridan, C., "Gene therapy finds its niche." Nat Biotechnol. 2011; 29(2): 121-128.
Shi, et al., "Insertional mutagenesis at positions 520 and 584 of adeno-associated virus type 2 (AAV2) capsid gene and generation of AAV2 vectors with eliminated heparin-binding ability and introduced novel tropism." Hum. Gene Ther.; vol. 17, pp. 353-361 (Mar. 2006).
Shi, et al., "Capsid modifications overcome low heterogeneous expression of heparan sulfate proteoglycan that limits AAV2-mediated gene transfer and therapeutic efficacy in human ovarian carinoma." Gynecol. Oncol.; vol. 103, pp. 1054-1062 (2006).
Shi, et al., "Insertional mutagenesis of the adeno-associated virus type 2 (AAV2) capsid gene and generation of AAV2 vectors targeted to alternative cell-surface receptors", Hum Gene Ther (2001); vol. 12, No. 14, pp. 1697-1711.
Shi, et al., "RGD inclusion in VP3 provides adeno-associated virus type 2 (AAV2)-based vectors with a heparan sulfate-independent cell entry mechanism." Mol. Ther.; vol. No. 4, pp. 515-525 (Apr. 2003).
Shiose, et al., "Gene transfer of a soluble receptor of VEGF inhibits the growth of experimental eyelid malignant melanoma" Invest Ophthalmol Vis Sci. 2000; 41(9): 2395-2403.
Shoji and Nakashima, "Current Status of Delivery Systems to Improve Target Efficacy of Oligonu-cleotides", Current Pharmaceutical Design. (2004); 10(7): 785-796.
Silva, et al., "Age-related macular degeneration and risk factors for the development of choroidal neovascularisation in the fellow eye: a 3-year follow-up study." Ophthalmologica. 2011; 226(3): 110-118.
Simonelli, et al., "Gene therapy for Leber's congenital amaurosis is safe and effective through 1.5 years after vector administration." Mol Ther. 2010; 18(3): 643-650.
Sonntag, et al., "Adeno-associated virus type 2 capsids with externalized VP1/VP2 trafficking domains are generated prior to passage through the cytoplasm and are maintained until uncoating occurs in the nucleus." Journal of Virology; vol. 80, No. 22, pp. 11040-11054 (Nov. 2006).
Sramek, C. et al., "Non-damaging retinal phototherapy: Dynamic range of heat shock protein expression." Investigative Ophthalmology & Visual Science. 2011; 52(3):1780-1787.
Stefansson, et al., "Metabolic physiology in age related macular degeneration." Prog Retin Eye Res. 2011; 30(1): 72-80.
Steinbach, et al., "Assembly of adeno-associated virus type 2 capsids in vitro." J of Gen Virology; vol. 78, pp. 1453-1462 (1997).
Stellmach, et al., "Prevention of ischemia-induced retinopathy by the natural ocular antiangiogenic agent pigment epithelium-derived factor." Proc Natl Acad Sci USA. 2001; 98(5): 2593-2597.
Stieger, et al., "AAV-mediated gene therapy for retinal disorders in large animal models." ILAR J. (2009); 50(2): 206-224.
Stieger, et al., "In vivo gene regulation using tetracycline-regulatable systems." Advanced Drug Delivery Reviews. 2009; 61(7-8): 527-41.
Stout, et al., "Surgical approaches to gene and stem cell therapy for retinal disease." Hum Gene Ther. 2011; 22(5): 531-535.
Stratford-Perricaudet, et al., "Widespread long-term gene transfer to mouse skeletal muscles and heart." J Clin Invest. 1992; 90(2): 626-630.
Streilein, et al., "Immunobiology and privilege of neuronal retina and pigment epithelium transplants." Vision Res. 2002; 42(4): 487-495.
Sullivan, et al., "Rationally designed AAV2 and AAVrh8R capsids provide improved transduction in the retina and brain." Gene Ther. (Jun. 2018); 25(3): 205-219. Epub May 22, 2018.
Sun, et al., "Immune response to adeno-associated virus and its recombinant vectors." Gene Therapy; vol. 10, pp. 964-976 (2003).
Surace, et al., "Delivery of Adeno-Associated Virus Vectors to the Fetal Retina: Impact of Viral Capsid Proteins on Retinal Neuronal Progenitor Transduction." Journal of Virology; vol. 77, No. 14, pp. 7957-7963 (Jul. 2003).
Sutter, Erich E. "The fast m-transform: a fast computation of cross-correlations with binary m-sequences." SIAM Journal on Computing (1991); 20.4: 686-694.
Swanson, William H., et al. "Temporal modulation sensitivity and pulse-detection thresholds for chromatic and luminance perturbations." JOSA A (1987); 4.10: 1992-2005.
Szewczenko-Pawlikowski, et al., "Heat shock-regulated expression of calreticulin in retinal pigment epithelium." Mol Cell Biochem. 1997; 177(1-2): 145-52.
Takada, et al., "Synaptic Pathology in Retinoschisis Knockout (Rs1-/y) Mouse Retina and Modification by 4 rAAV-Rs1 Gene Delivery." Investigative Ophthalmology & Visual Science; vol. 49, No. 8, pp. 3677-3678 (Aug. 2008).
Takayama, et al., "Suppression of tumor angiogenesis and growth by gene transfer of a soluble form of vascular endothelial growth factor receptor into a remote organ." Cancer Res. 2000; 60(8): 2169-2177.
Tal, "Adeno-Associated Virus-Based Vectors in Gene Therapy." Journal of Biomedical Science; vol. 7, No. 4, pp. 279-291 (Jul. 2000).
Thyagarajan, Bhaskar, et al. "Site-specific genomic integration in mammalian cells mediated by phage φC31 integrase." Molecular and Cellular Biology (2001); 21.12: 3926-3934.
Tolentino, et al., "Vascular endothelial growth factor is sufficient to produce iris neovascularization and neovascular glaucoma in a nonhuman primate." Arch Ophthalmol. 1996; 114(8): 964-670.
Tomar, et al., "Use of Adeno-Associated Viral Vector for Delivery of Small Interfering RNA." Oncogene; vol. 22, No. 36, pp. 5712-5715 (Aug. 28, 2003).
Tse, et al.; "Structure-guided evolution of antigenically distinct adeno-associated virus variants for immune evasion"; PNAS (2017); E4812-E4821; 10 pages.
Ueyama, Hisao, et al. "Analysis of introns and promoters of L/M visual pigment genes in relation to deutan color-vision deficiency with an array of normal gene orders." Journal of Human Genetics (2009); 54.9: 525-530.
Urabe, et al., "Insect cells as a factory to produce adena-associated virus type 2 vectors." Hum Gene Ther. 2002; 13(16): 1935-1943.
US National Health Institute: "Safety and Efficacy Study of rAAV. sFlt-1 in Patients With Exudative Age-Related Macular Degeneration", NCT01494805, Clinical Trials, Updated Dec. 16, 2011; XP002751808, Retrieved from the Internet: URL:https:jjclinicaltrials. govjarchivejNCT01494805/2011_12_16 [retrieved on-Dec. 4, 2015].
US National Institute of Health: "Safety and Tolerability Study of AAV2-sFLT01 in Patients With Neovascular Age-Related Macular Degeneration (AMD)", NCT01024998, Clinical Trials, Updated

(56) References Cited

OTHER PUBLICATIONS

Apr. 13, 2012; XP002751809, Retrieved from the Internet: URL:https:jjclinicaltrials.govjarchive/NCT01024998/2012_04_13 [retrieved on-Dec. 4, 2015].

Van Vliet, et al., "Proteolytic mapping of the adeno-associated virus capsid." Mol Ther. (Dec. 2006); 14(6): 809-821.

Verma and Somia, "Gene therapy—promises, problems and prospects", Nature 1997; 389: 239-242.

Viard, et al., "Clusterin gene expression mediates resistance to apoptotic cell death induced by heat shock and oxidative stress." J Invest Dermatol. 1999; 112(3): 290-296.

Vigna, et al., "Lentiviral vectors: excellent tools for experimental gene transfer and promising candidates for gene therapy." J Gene Med. 2000; 2(5): 308-316.

Wada, et al., "Expression of vascular endothelial growth factor and its receptor (KDR/flk-1) mRNA in experimental choroidal neovascularization." Curr Eye Res. 1999; 18(3): 203-213.

Wang, et al., "A locus control region adjacent to the human red and green visual pigment genes." Neuron. 1992; 9(3): 429-440.

Wang, et al., "Spatiotemporal control of gene expression by a light-switchable transgene system." Nature Methods. 2012; 9(3): 266-269.

Watanabe, et al., "Tropisms of AAV for Subretinal Delivery to the Neonatal Mouse Retina and Its Application for In Vivo Rescue of Developmental Photoreceptor Disorders." PLoS One; vol. 8, No. 1, 12 paqes. (Jan. 15, 2013).

Waterkamp, et al., "Isolation of targeted AAV2 vectors from novel virus display libraries." J. Gene. Med.; vol. 8, pp. 1307-1319 (Sep. 6, 2006).

Wells, et al., "Levels of vascular endothelial growth factor are elevated in the vitreous of patients with subretinal neovascularisation." Br J Ophthalmol. 1996; 80(4): 363-366.

Wenkel, et al., "Analysis of immune deviation elicited by antigens injected into the subretinal space." Invest Ophthalmol Vis Sci. 1998; 39(10): 1823-1834.

Wenkel, et al., "Evidence that retinal pigment epithelium functions as an immune-privileged tissue." Invest Ophthalmol Vis Sci. 2000; 41(11): 3467-73.

White, et al., "Genetic modification of adeno-associated viral vector type 2 capsid enhances gene transfer efficiency in polarized human airway epithelial cells." Human Gene Therapy; vol. 19, pp. 1407-1414 (Dec. 2008).

White, et al., "Targeted gene delivery to vascular tissue in vivo by tropism-modified adeno-associated virus vectors." Circulation; vol. 109, pp. 513-519 (Feb. 3, 2004).

Wickham, et al., "Increased in vitro and in vivo gene tranfer be adenovirus vectors containing chimeric fiber proteins." Journal of Virology; vol. 71, No. 11, pp. 8221-8229 (Nov. 1997).

Wiesel, Torsten N., and Hubel, David H. "Single-cell responses in striate cortex of kittens deprived of vision in one eye." J Neurophysiol (1963); 26.6: 1003-1017.

Wiesmann, et al., "Crystal structure at 1.7 a resolution of VEGF in complex with domain 2 of the Flt-1 receptor." Cell. 1997; 91(5): 695-704.

Wobus, et al., "Monoclonal antibodies against the adeno-associated virus type 2 (AAV-2) capsid: epitope mapping and identification of capsid domains involved in AAV-2-cell interaction and neutralization of AAV-2 infection." J. Virol.; vol. 74, No. 19, pp. 9281-9293 (Oct. 2000).

Wolf, et al., "Preeclampsia and future cardiovascular disease: potential role of altered angiogenesis and insulin resistance." J Clin Endocrinol Metab. 2004; 89(12): 6239-6243.

Wong, et al., "Intravitreal VEGF and bFGF produce florid retinal neovascularization and hemorrhage in the rabbit." Curr Eye Res. 2001; 22(2): 140-147.

Work, et al., "Vascular bed-targeted in vivo gene delivery using tropism-modified adeno-associated viruses." Mol. Ther.; vol. 13, No. 4, pp. 683-693 (Apr. 2006).

Wu, et al., "Mutational analysis of the adeno-associated virus type 2 (AAV2) capsid gene and construction of AAV2 vectors with altered tropism." Journal of Virology (2000); vol. 71, No. 18, pp. 8635-8647.

Wu, et al., "Self-complementary recombinant adeno-associated viral vectors: packaging capacity and the role of rep proteins in vector purity." Hum Gene Ther. 2007; 18(2): 171-182.

Wu, et al., "$\alpha 2,3$ and $\alpha 2,6$ N-Linked Sialic Acids Facilitate Efficient Binding and Transduction by Adeno-Associated Virus Types 1 and 6.", Journal of Virology (2006); vol. 80, No. 18, pp. 9093-9103.

Wulff, et al., "Luteal angiogenesis: prevention and intervention by treatment with vascular endothelial growth factor trap(A40)." J Clin Endocrinol Metab. 2001; 86(7): 3377-3386.

Wykoff, et al., "Perioperative management of patients with reported povidone-iodine or penicillin/cephalosporin allergies." Presented at the Annual Meeting for the Association for Research in Vision and Opthalmology. Fort Lauderdale, FL. May 5, 2011; Abstract No. 6416/D880.

Xiao, et al., "Production of high-titer recombinant adena-associated virus vectors in the absence of helper adenovirus." J. Virol. 1998; 72(3): 2224-2232.

Xiao, et al.; "Adenovirus-facilitated nuclear translocation of adeno-associated virus type 2." Journal of Virology; vol. 76, No. 22, pp. 11505-11517 (Nov. 2002).

Xi E, et al., "The atomic structure of adeno-associated virus (AAV-2), a vector for human gene therapy." PNAS; vol. 99, No. 16, pp. 10405-10410 (Aug. 6, 2002).

Xu, Zhengyao, et al. "Accuracy and efficiency define Bxb1 integrase as the best of fifteen candidate serine recombinases for the integration of DNA into the human genome." BMC Biotechnology (2013); 13: 87, 17 pages.

Yang, et al., "Cellular and humoral immune responses to viral antigens create barriers to lung-directed gene therapy with recombinant adenoviruses." J Virol. 1995; 69(4): 2004-2015.

Yang, et al., "Directed Evolution of Adeno=Associated Virus (AAV) as Vector for Muscle Gene Therapy." Methods in Molecular Biology; vol. 709, pp. 127-139 (2011).

Yang, et al., "A myocardium tropic adeno-associated virus (AAV) evolved by DNA shuffling and in vivo selection." PNAS; vol. 106, No. 10, pp. 3946-3951 (Mar. 10, 2009).

Ye, et al., "sFlt-1 gene therapy of follicular thyroid carcinoma." Endocrinology. 2004; 145(2): 817-822.

Ye, Guo-jie, et al. "Development and Evaluation of Cone-Specific Promoters in Non-human Primates for Gene Therapy of Congenital Cone Diseases Including Achromatopsia." ARVO Annual Meeting Abstract, Investigative Ophthalmology & Visual Science (2014); 55.13: 837-837, 5 pages.

Yero, et al., "Immunization of mice with Neisseria meningitides serogroup B genomic expression libraries elicits functional antibodies and reduces the level of bacteremia in an infant rat infection model", Vaccine (2005); 23(7): 932-939.

Yin, et al., "Intravitreal injection of AAV2 transduces macaque inner retina." Invest Ophthalmol Vis Sci. 2011; 52(5): 2775-2783.

Zabner, et al., "Adeno-associated virus type 5 (AAV5) but not AAV2 binds to the apical surfaces of airway epithelia and facilitates gene transfer." J Virol.; No. 74, No. 8, pp. 3852-3858 (Apr. 2000).

Zhang, et al., "AAV-mediated Gene Therapy Restores Cone Function in a Rat With an M-cone Opsin Deficiency, A Model for Blue Cone Monochromacy", Investigative Opthamology & Visual Science (2011); ARVO Annual Meeting Abstract, 52:1403.

Zhang, et al., "Suppression of tumor growth by oncolytic adenovirus-mediated delivery of an antiangiogenic gene, soluble Flt-1." Mol Ther. 2005; 11(4): 553-562.

Zhao, et al., "Molecular evolution by staggered extension process (StEP) in vitro recombination." Nat Biotechnol; vol. 16, No. 3, pp. 258-261 (Mar. 1998).

Zheng, et al., "Genomic integration and gene expression by a modified adenoviral vector." Nat Biotechnol. 2000; 18(2): 176-180.

Zolotukhin, et al., "Recombinant adeno-associated virus purification using novel methods improves infectious titer and yield." Gene Therapy (1999); vol. 6, pp. 973-985.

(56) References Cited

OTHER PUBLICATIONS

Zufferey, et al., "Multiply attenuated lentiviral vector achieves efficient gene delivery in vivo." Nat Biotechnol. (1997), 15(9): 871-875.
Clinical Trial NCT01494805, History of Changes for "Safety and Efficacy Study of rAAV.sFlt-1 in Patients With Exudative Age-Related Macular Degeneration (AMD)", NCT01494805, Submitted Date: Dec. 15, 2011 (v1), ClinicalTrials.gov, https://clinicaltrials.gov/ct2/history/NCT01494805?V_1=View#StudyPageTop, 9 pages.
U.S. Appl. No. 14/281,749, filed May 19, 2014, US 2015-0004101 A1, Jan. 1, 2015, U.S. Pat. No. 9,943,573, Apr. 17, 2018, Registered.
U.S. Appl. No. 14/660,657, filed Mar. 17, 2015, US 2015-0259395 A1, Sep. 17, 2015, U.S. Pat. No. 10,000,741, Jun. 19, 2018, Registered.
U.S. Appl. No. 15/388,380, filed Dec. 22, 2016, US 2017-0183647 A1, Jun. 29, 2017, U.S. Pat. No. 10,584,328, Mar. 10, 2020, Registered.
U.S. Appl. No. 15/851,650, filed Dec. 21, 2017, US 2018-0125948 A1, May 10, 2018, U.S. Pat. No. 10,004,788, Jun. 26, 2018, Registered.
U.S. Appl. No. 15/788,446, filed Oct. 19, 2017, US 2018-0127471 A1, May 10, 2018, Pending.
U.S. Appl. No. 15/939,674, filed Mar. 29, 2018, US 2018-0344197 A1, Dec. 6, 2018, Pending.
U.S. Appl. No. 15/961,654, filed Apr. 24, 2018, US 2018-0311319 A1, Nov. 1, 2018, Pending.
U.S. Appl. No. 15/984,085, filed May 18, 2018, US 2018-0320145 A1, Nov. 8, 2018, Pending.
U.S. Appl. No. 16/097,377, filed May 1, 2017, US 2019-0142975 A1, May 16, 2019, Pending.
U.S. Appl. No. 16/098,354, filed May 2, 2017, US 2019-0154667 A1, May 23, 2019, Pending.
U.S. Appl. No. 16/488,689, filed Feb. 28, 2018, Pending.
U.S. Appl. No. 16/494,203, filed Mar. 16, 2018, US 2020-0010851 A1, Jan. 9, 2020, Pending.
U.S. Appl. No. 16/750,736, filed Jan. 23, 2020, Pending.
Cronin, et al., "Efficient transduction and optogenetic stimulation of retinal bipolar cells by a synthetic adeno-associated virus capsid and promoter". EMBO Mol Med. (Sep. 2014); 6(9): 1175-1190.
Gardner, et al., "X-Linked Cone Dystrophy Caused by Mutation of the Red and Green Cone Opsins". Am J Hum Genet. (Jul. 9, 2010); 87(1): 26-39.
Khaboo, et al., "Insight into the mechanisms of enhanced retinal transduction by the engineered AAV2 capsid variant—7m8". Biotechnol Bioeng. (Dec. 2016); 113(12): 2712-2724. Epub Jun. 30, 2016.
NCBI Reference Sequence NM_000513.2, by Gen Bank, on line published and documented at https://www.ncbi.nlm.nih.gov/nuccore/NM_000513.2/, printed Jun. 23, 2020, 5 pages (Year: 2020).
Ortolano, et al., "Present and future of adeno associated virus based gene therapy approaches". Recent Pat Endocr Metab Immune Drug Discov. (Jan. 2012); 6(1): 47-66.
Popa-Wagner, et al., "Impact of VP1-Specific Protein Sequence Motifs on Adeno-Associated Virus Type 2 Intracellular Trafficking and Nuclear Entry". Journal of Virology (Sep. 2012); 86(17): 9163-9174. Epub Jun. 13, 2012.
Rayaprolu, et al., "Comparative analysis of adeno-associated virus capsid stability and dynamics". Jornal of Virology (Dec. 2013); 87(24): 13150-13160. Epub Sep. 25, 2013.
Santiago-Ortiz, et al., "AAV ancestral reconstruction library enables selection of broadly infectious viral variants". Gene Ther. (Dec. 2015); 22(12): 934-946. Epub Jul. 17, 2015.
Venkatakrishnan, et al., "Structure and Dynamics of Adeno-Associated Virus Serotype 1 VP1-Unique N-Terminal Domain and Its Role in Capsid Trafficking". Journal of Virology (Apr. 2013); 87 (9): 4974-4984.
Winderickx, et al., "Defective Colour Vision Associated With a Missense Mutation in the Human Green Visual Pigment Gene". Nat Genet. (Jul. 1992); 1(4): 251-256.
Lane, et al.; "Production, purification, crystallization and preliminary X-ray analysis of adeno-associated virus serotype 8"; Acta Crystallographica; F61, pp. 558-561 (2005).
Lochrie, et al., "Mutations on the External Surfaces of Adeno-Associated Virus Type 2 Capsids That Affect Transduction and Neutralization" Journal of Virology (Jan. 2006); 80(2): 821-834.
Miller, et al.; "Production, purification and preliminary X-ray crystallographic studies of adeno-associated virus serotype 1"; Acta Crystallographica; F62, pp. 1271-1274 (2006).
Walters, et al.; "Structure of Adeno-Associated Virus Serotype 5"; Journal of Virology; vol. 78, No. 7, nns. 3361-3371 (Apr. 2004).
Wu, et al.; "Single Amino Acid Changes Can Influence Titer, Heparin Binding, and Tissue Tropism in Different Adeno-Associated Virus Serotypes"; Journal of Virology; vol. 80, No. 22, pp. 11393-11397 (Nov. 2006).
U.S. Appl. No. 14/281,749 dated May 19, 2014, U.S. Publication No. US 2015-0004101 A1 dated Jan. 1, 2015.
U.S. Appl. No. 14/660,657 dated Mar. 17, 2015, U.S. Publication No. US 2015-0259395 A1 dated Sep. 17, 2015.
U.S. Appl. No. 15/388,380 dated Dec. 22, 2016, U.S. Publication No. US 2017-0183647 A1 dated Jun. 29, 2017.
U.S. Appl. No. 15/851,650 dated Dec. 21, 2017, U.S. Publication No. US 2018-0125948 A1 dated May 10, 2018.
U.S. Appl. No. 13/889,275 dated May 7, 2013, U.S. Publication No. US 2013-0323302 A1 dated Dec. 5, 2013, Abandoned.
U.S. Appl. No. 14/281,765 dated May 19, 2014, U.S. Publication No. US 2014-0341977 A1 dated Nov. 20, 2014, Abandoned.
U.S. Appl. No. 14/281,763 dated May 19, 2014, Abandoned.
U.S. Appl. No. 14/407,054 dated Jun. 10, 2013, U.S. Publication No. US 2015-0111275 A1 dated Apr. 23, 2015, Abandoned.
U.S. Appl. No. 16/488,689 dated Feb. 28, 2018.
U.S. Appl. No. 16/998,540 dated Aug. 20, 2020.
U.S. Appl. No. 15/939,674 dated Mar. 29, 2018, U.S. Publication No. US 2018-0344197 A1 dated Dec. 6, 2018.
U.S. Appl. No. 15/984,085 dated May 18, 2018, U.S. Publication No. US 2018-0320145 A1 dated Nov. 8, 2018.
U.S. Appl. No. 16/097,377 dated May 1, 2017, U.S. Publication No. US 2019-014975 A1 dated May 16, 2019.
U.S. Appl. No. 15/788,446 dated Oct. 19, 2017, U.S. Publication No. US 2018-0127471 A1 dated May 20, 2018.
U.S. Appl. No. 15/961,654 dated Apr. 24, 2018, U.S. Publication No. US 2016-0311319 A1 dated Nov. 1, 2018.
U.S. Appl. No. 16/098,354 dated May 2, 2017, U.S. Publication No. US 2019-0154667 A1 dated May 23, 2019.
U.S. Appl. No. 16/494,203 dated Mar. 16, 2018, U.S. Publication No. US 2020-0010851 A1 dated Jan. 9, 2020.
U.S. Appl. No. 16/750,736 dated Jan. 23, 2020, U.S. Publication No. US 2020-0149033 A1 dated May 14, 2020.
U.S. Appl. No. 15/388,380 dated Dec. 22, 2016, U.S. Publication No. US 2017-0183467 A1 dated Jun. 29, 2017.
U.S. Appl. No. 15/939,674 dated Mar. 29, 2016, U.S. Publication No. US 2018-0344197 A1 dated Dec. 6, 2018.
U.S. Appl. No. 16/097,377 dated May 1, 2017, U.S. Publication No. US 2019-0149275 A1 dated May 16, 2019.
U.S. Appl. No. 15/788,446 dated Oct. 19, 2017, U.S. Publication No. US 2018-0147471 A1 dated May 10, 2018.
U.S. Appl. No. 15/961,654 dated Apr. 24, 2018, U.S. Publication No. US 2018-0311319 A1 dated Nov. 1, 2018.
U.S. Appl. No. 16/750,736 dated Jan. 23, 2020, U.S. Publication No. US 2020-0419033 A1 dated May 14, 2020.
U.S. Appl. No. 15/939,674 dated Mar. 29, 2018, U.S. Publication No. US 2018-0344197 dated Dec. 6, 2018.
U.S. Appl. No. 14/075,415 dated Nov. 8, 2013, U.S. Publication No. US 2014-0080900 dated Mar. 30, 2014.

* cited by examiner

COMPOSITIONS AND METHODS FOR INTRAVITREAL DELIVERY OF POLYNUCLEOTIDES TO RETINAL CONES

CROSS REFERENCE TO RELATED APPLICATIONS

This application is a U.S. National Phase Application of International Patent Application No. PCT/US2016/020482, filed Mar. 2, 2016; which claims the benefit under 35 U.S.C. § 119(e) of U.S. Provisional Application No. 62/127,194, filed on Mar. 2, 2015, and U.S. Provisional Application No. 62/134,466, filed on Mar. 17, 2015; each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AVBI_006_02US_ST25.bd. The text file is 81 KB, was created on Mar. 19, 2020, and is being submitted electronically via EFS-Web.

FIELD OF THE INVENTION

This invention pertains to viral-based gene therapy of retinal disorders.

BACKGROUND OF THE INVENTION

Photoreceptors are a specialized type of neuron found in the retina that are capable detecting light and converting that light signal into electrical signals. There are two types of photoreceptors in the retina: rod photoreceptors, which are more sensitive to light and hence support vision in dim lighting; and cone photoreceptors, which are sensitive to specific wavelengths of light and hence support the perception of color, and which respond faster to stimuli than rods so perceive finer detail and more rapid changes in images than rods and hence support high acuity vision.

A number of vision disorders are associated with a loss of viability or function of the cone photoreceptors, including, for example, those associated with defects within cones, i.e. cone-intrinsic defects, such as Stargardt's macular dystrophy, cone dystrophy, cone-rod dystrophy, Spinocerebellar ataxia type 7, and Bardet-Biedl syndrome-1, as well as color vision disorders, including achromotopsia, blue cone monochromacy, and protan, deutan, and tritan defects; and those that are associated with retinal disorders that affect the central macula, such as age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis. It is expected that these cone cell disorders may be treated by delivering to cone photoreceptors a therapeutic gene that, when expressed by the cone photoreceptors, complements the deficiency and "rescues" the cone cell viability and/or function.

The highest density of cone photoreceptors exist at the 1.5 mm depression located in the center of the macula of the retina. This region, called the "fovea centralis" or "foveal pit", is responsible for sharp central vision (also called foveal vision), which is necessary in humans for activities where visual detail is of primary importance, such as reading and driving. The fovea centralis consists of two sub-regions: the foveola, a 0.35 mm diameter rod-free region of retina at the center of the pit; and the fovea, a 1.5 mm-diameter cone-enriched region of retina that surrounds the foveola and forms the slopes of the pit. Surrounding the fovea centralis is the parafovea, which forms the lip of the depression and is comprised of all cells of the retina, cone photoreceptors being represented in reduced numbers relative to in the fovea centralis. Beyond the parafovea is the perifovea, a region of retina which contains an even more diminished density of cones. Because cone cells of the fovea constitute the vast majority of cone photoreceptors in the retina, these cells are ideal target recipients of therapeutic genes delivered for the treatment of cone-associated disorders (Oster 1935).

Some success at delivering genes to cells of the retina has been achieved by employing viral vectors such as adeno-associated virus (AAV) or lentivirus. However, these vectors must be administered by subretinal injection, a procedure that disrupts the structure of the retina and carries with it a risk of creating additional damage to retinal tissue that is often already damaged by the disorder being treated. One alternative is to deliver the viral vector to the retina intravitreally, i.e., by injecting the vector into the vitreous of the eye and hoping that the vector permeates the retina and transduces the retinal cells. However, as demonstrated by the art, foveal cone cells are notoriously resistant to transduction by viral vectors delivered intravitreally to the retina.

Thus, there is a need in the art for viral vectors that transduce cone cells with high efficiency when delivered from the vitreous of the eye. The present invention addresses these issues.

SUMMARY OF THE INVENTION

Methods and compositions are provided for intravitreally delivering a polynucleotide to cone photoreceptors. Aspects of the methods include injecting a recombinant adeno-associated virus comprising a polynucleotide of interest into the vitreous of the eye. These methods and compositions find particular use in treating ocular disorders associated with cone dysfunction and/or death.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
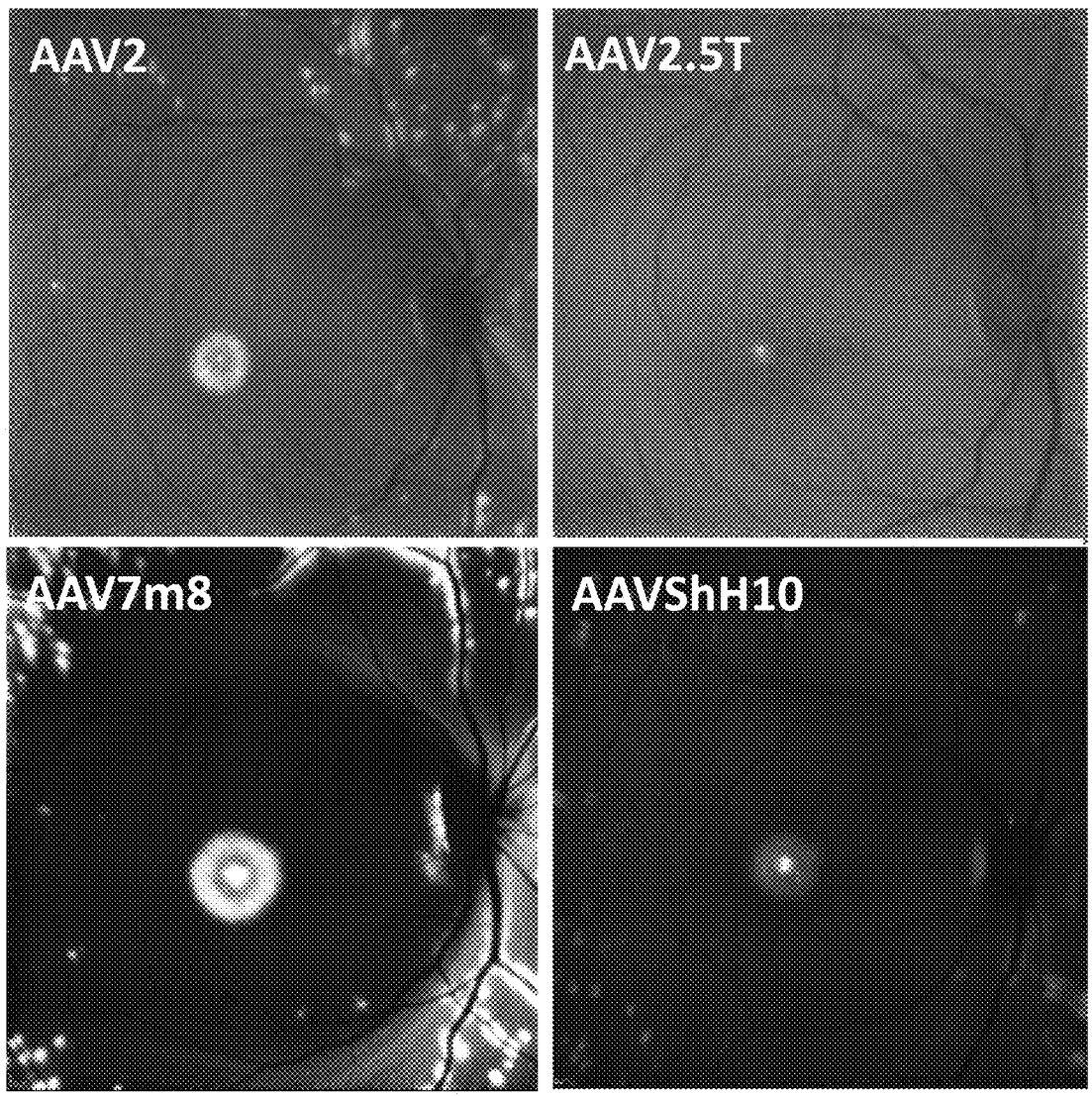
FIG. 1 illustrates how intravitreally-delivered AAV2 variant AAV2-7m8 transduces retinal cells in the fovea centralis and parafovea of primates more efficiently than intravitreally-delivered AAV2. $5 \times 10^{11}$ vector genomes of AAV2.CMV.GFP (upper left); AAV-2.5T.CMV.GFP (upper right) (Excoffon K. J., et al. 2009. Proc. Natl. Acad. Sci. U.S.A 106:3865-3870); (lower left) AAV2-7.8.CMV.GFP (Dalkara D, et al. Sci Transl Med. 2013 Jun. 12; 5(189): 189ra76); or AAV-ShH10.CMV.GFP (lower right) (Klimczak R R et al. PLoS One. 2009 Oct. 14; 4(10):e7467) was injected into the vitreous of an African green monkey in a volume of 50 uL, and GFP expression was observed 8 weeks later by OCT fluorescence imaging in vivo.

Methods and compositions are provided for intravitreally delivering a polynucleotide to cone photoreceptors. Aspects of the methods include injecting a recombinant adeno-associated virus comprising the polynucleotide of interest into the vitreous of the eye. These methods and compositions find particular use in treating ocular disorders associated with cone dysfunction and/or death. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

It must be noted that as used herein and in the appended claims, the singular forms "a", "an", and "the" include plural referents unless the context clearly dictates otherwise. Thus, for example, reference to "a cell" includes a plurality of such cells and reference to "the polynucleotide" includes reference to one or more polynucleotides and equivalents thereof, e.g. nucleic acid sequences, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors (virus or the viral genome thereof), liposomes, and other gene delivery vehicles.

By a "virus" it is meant a viral particle comprising a viral capsid and a viral genome. For example, an adeno-associated virus refers to a viral particle comprising at least one adeno-associated virus capsid protein or variant thereof and an encapsidated adeno-associated virus vector genome or variant thereof.

By a viral "capsid" it is meant the protein shell of a virus. Viral capsids typically comprise several oligomeric structural subunits made of protein called protomers. The capsid encloses, or "encapsidates", the genetic material, or "genome", of the virus. In some viruses, the capsid is enveloped, meaning that the capsid is coated with a lipid membrane known as a viral envelope.

By a viral "genome" (referred to interchangeably herein as "viral genome", "viral vector DNA" and "viral DNA"), it is meant a polynucleotide sequence comprising at least one, and generally two, viral terminal repeats (e.g. inverted terminal repeats (ITRs), long terminal repeats (LTR)) at its ends.

By a "recombinant viral genome" it is meant a viral genome comprising a heterologous nucleic acid sequence and at least one, and generally two, viral terminal repeats at its ends. By a "recombinant virus" it is meant a viral particle comprising a recombinant viral genome.

As used herein, the term "heterologous" means derived from a genotypically distinct entity from that of the rest of the entity to which it is being compared. For example, a polynucleotide introduced by genetic engineering techniques into a plasmid or vector derived from a different species, e.g. a viral genome, is a heterologous polynucleotide. As another example, a promoter removed from its native coding sequence and operatively linked to a coding sequence with which it is not naturally found linked is a heterologous promoter. As a third example, a heterologous gene product, e.g. RNA, protein, is a gene product not normally encoded by a cell in which it is being expressed.

The term "replication defective" as used herein relative to the viruses of the disclosure refers to a virus that cannot independently replicate and package its genome. For example, when a cell of a subject is infected with recombinant virions, the heterologous gene is expressed in the infected cells; however, due to the fact that the infected cells lack AAV rep and cap genes and accessory function genes, the recombinant virus is not able to replicate further.

The term "AAV" is an abbreviation for adeno-associated virus. When used herein, the term AAV may be used to refer to the virus itself or derivatives thereof, e.g. the viral capsid, the viral genome, and the like. The term "AAV" encompasses all subtypes, both naturally occurring and recombinant forms, and variants thereof except where required otherwise.

By "naturally occurring" or "wild-type" AAV it is meant any adeno-associated virus or derivative thereof comprising a viral capsid that consists of viral capsid proteins that occur in nature. Non-limiting examples of naturally occurring AAV include AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV9, AAV10, AAV11, AAV12, rh10, avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

By an "AAV variant" or a "variant AAV" it is meant to include an AAV viral particle comprising a variant, or mutant, AAV capsid protein. Examples of variant AAV capsid proteins include AAV capsid proteins comprising at least one amino acid difference (e.g., amino acid substitution, amino acid insertion, amino acid deletion) relative to a corresponding parental AAV capsid protein, i.e. an AAV capsid protein from which it was derived, a wild type AAV capsid protein, etc., where the variant AAV capsid protein does not consist of an amino acid sequence present in a naturally occurring AAV capsid protein. In addition to differing structurally, i.e. at the sequence level, from the corresponding parental AAV, the AAV variant may differ functionally from the corresponding parental AAV. Put another way, the variant capsid protein comprising the at least one amino acid difference relative to a corresponding parental AAV capsid protein may confer functional characteristics on the AAV variant that are not possessed by the corresponding parental AAV. For example, the AAV variant may have a different cellular tropism, i.e. a different affinity for and/or ability to infect a particular type of cell, e.g. the AAV variant may bind to a cell, e.g. a retinal cell, with an increased (or decreased) affinity than the parental AAV, and/or infect/transduce a cell, e.g. a retinal cell, with an increased (or decreased) efficiency than the parental AAV such that more (or less) cells of a cell population is transduced/infected with the same titer of viral particles. As a second example, the AAV variant may have a greater (or lesser) affinity for antibodies produced by the host animal, e.g. the AAV variant may bind with greater (or lesser) affinity to neutralizing antibodies and be cleared from the host tissue to a greater (or lesser) extent.

By "recombinant AAV", or "rAAV" it is meant to include any AAV that comprises a heterologous polynucleotide sequence in its viral genome. In general, the heterologous polynucleotide is flanked by at least one, and generally by two naturally occurring or variant AAV inverted terminal repeat sequences (ITRs). The term rAAV vector encompasses both rAAV vector particles and rAAV vector plasmids. Thus, for example, an rAAV that comprises a heterologous polynucleotide sequence would be an rAAV that includes a nucleic acid sequence not normally included in a naturally-occurring, wild-type AAV, for example, a transgene (e.g. a non-AAV RNA-coding polynucleotide sequence, non-AAV protein-coding polynucleotide sequence), a non-AAV promoter sequence, a non-AAV poly-adenylation sequence, etc.

As used herein, the term "expression vector" refers to a vector comprising a region which encodes a gene product of interest, and is used for effecting the expression of a gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

As used herein, the term "expression" refers to the transcription and/or translation of a coding sequence, e.g. an endogenous gene, a heterologous gene, in a cell.

As used herein, the terms "gene" or "coding sequence" refer to a polynucleotide sequence that encodes a gene product, and encompasses both naturally occurring polynucleotide sequences and cDNA. A gene may or may not include regions preceding and following the coding region, e.g. 5' untranslated (5' UTR) or "leader" sequences and 3' UTR or "trailer" sequences, or intervening sequences (introns) between individual coding segments (exons).

As used herein, the term "gene product" refers the desired expression product of a polynucleotide sequence such as a polypeptide, peptide, protein or RNA including, for example, a ribozyme, short interfering RNA (siRNA), miRNA or small hairpin RNA (shRNA). The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component.

As used herein, the terms "operatively linked" or "operably linked" refers to a juxtaposition of genetic elements on a single polynucleotide, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained. The combination of control elements, e.g. promoter, enhancer(s), etc. and a gene or genes to which they are operably linked for expression is sometimes referred to as an "expression cassette," a large number of which are known and available in the art or can be readily constructed from components that are available in the art.

By a "promoter" it is generally meant a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species-specific. Promoters may be "constitutive," meaning continually active, or "inducible," meaning the promoter can be activated or deactivated by the presence or absence of biotic or abiotic factors.

By an "enhancer" it is generally meant a cis-acting regulatory element that stimulates, i.e. promotes or enhances, transcription of an adjacent genes. By a "silencer" it is meant a cis-acting regulatory element that inhibits, i.e. reduces or suppresses, transcription of an adjacent gene, e.g. by actively interfering with general transcription factor assembly or by inhibiting other regulatory elements, e.g. enhancers, associated with the gene. Enhancers can function (i.e., can be associated with a coding sequence) in either orientation, over distances of up to several kilobase pairs (kb) from the coding sequence and from a position downstream of a transcribed region. Enhancer sequences influence promoter-dependent gene expression and may be located in the 5' or 3' regions of the native gene. Enhancer sequences may or may not be contiguous with the promoter sequence. Likewise, enhancer sequences may or may not be immediately adjacent to the gene sequence. For example, an enhancer sequence may be several thousand basepairs from the promoter and/or gene sequence. For example, the L/M minimal opsin enhancer, referred to as the Locus Control Region (LCR) (Wang et al., 1992. Neuron 9: 429-440) (SEQ ID NO:25) can be used to enhance gene expression in cone cells; its absence results in blue cone monochromacy (Nathans et al., 1989; Science, 245: 831-838). The LCR has been shown to be useful in gene therapy, for example with AAV vectors (Li et al., Vision Research 48(2008): 332-338). Furthermore, a functional fragment consisting essentially of a 36 bp "core" LCR sequence has been identified that is necessary and sufficient for expression from the opsin promoter in cone cells (SEQ ID NO:24).

A "termination signal sequence" within the meaning of the invention may be any genetic element that causes RNA polymerase to terminate transcription, such as for example a polyadenylation signal sequence. A polyadenylation signal sequence is a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

The terms "identical" or percent "identity" in the context of two or more nucleotide sequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

As used herein, the term "sequence identity" refers to the degree of identify between nucleotides in two or more aligned sequences, when aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Sequence identity may be determined by aligning sequences using any of a number of publicly available alignment algorithm tools, e.g., the local homology algorithm of Smith & Waterman, Adv. Appl. Math. 2: 482 (1981), the homology alignment algorithm of Needleman & Wunsch, J Mol. Biol. 48: 443 (1970), the search for similarity method of Pearson & Lipman, Proc. Nat'l. Acad. Sci. USA 85: 2444 (1988), computerized implementations of these algorithms (GAP, BESTFIT, FASTA, and TFASTA in the Wisconsin Genetics Software Package, Genetics Computer Group, 575 Science Dr., Madison, Ws.), by the BLAST algorithm, Altschul et al., J Mol. Biol. 215: 403-410 (1990), with software that is publicly available through the National Center for Biotechnology Information (www.ncbi.nlm.nih.gov/), or by visual inspection (see generally, Ausubel et al., infra).

The terms "complement" and "complementary" refer to two antiparallel nucleotide sequences capable of pairing with one another upon formation of hydrogen bonds between the complementary base residues in the antiparallel nucleotide sequences.

The term "native", when used in the context of a polynucleotide or polypeptide herein, refers to a polynucleotide or polypeptide sequence that is found in nature; i.e., that is present in the genome of a wild-type virus or cell.

The term "variant", when used in the context of a polynucleotide or polypeptide herein, refers to a mutants of a native polynucleotide or polypeptide having less than 100% sequence identity with the native sequence or any other native sequence. Such variants may comprise one or more substitutions, deletions, or insertions in the corresponding native gene or gene product sequence. The term "variant" also includes fragments of the native gene or gene product, and mutants thereof, e.g. fragments comprising one or more substitutions, deletions, or insertions in the corresponding native gene or gene product fragment. In some embodiments, the variant retains a functional activity of the native gene product, e.g. ligand binding, receptor binding, protein signaling, etc., as known in the art.

The term "fragment," when referring to a recombinant protein or polypeptide of the invention means a polypeptide having an amino acid sequence which is the same as part of, but not all of, the amino acid sequence of the corresponding full length protein or polypeptide, which retains at least one of the functions or activities of the corresponding full length protein or polypeptide. The fragment preferably includes at least 20-100 contiguous amino acid residues of the full length protein or polypeptide.

As used herein, the terms "biological activity" and "biologically active" refer to the activity attributed to a particular gene product, e.g. RNA or protein, in a cell line in culture or in vivo. For example, the "biological activity" of an RNAi molecule refers to the ability of the molecule to inhibit the production of a polypeptide from a target polynucleotide sequence.

As used herein, the term "antagonist" refers a molecule that acts to inhibit the activity of a target molecule. Antagonists include both structural antagonists that inhibit the activity of the target molecule by, for example, binding directly to the target or inactivating its receptor and functional antagonists, which, for example, decrease production of the target in a biological system or increase production of inhibitors of the target in a biological system.

The terms "administering" or "introducing", as used herein refer to contacting a cell, tissue, or subject with a vector for the purposes of delivering a polynucleotide to the cell or to cells and or organs of the subject. Such administering or introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" or "transfection" as used herein refers to the delivery of a heterologous DNA to the interior of a cell, e.g. a mammalian cell, an insect cell, a bacterial cell, etc. by a vector. A vector used to "transform" a cell may be a plasmid, minicircle DNA, or other vehicle. Typically, a cell is referred to as "transduced", "infected"; "transfected" or "transformed" dependent on the means used for administration, introduction or insertion of heterologous DNA (i.e., the vector) into the cell. The terms "transfected" and "transformed" are used interchangeably herein to refer to the introduction of heterologous DNA by non-viral methods, e.g. electroporation, calcium chloride transfection, lipofection, etc., e.g. as when preparing the subject viral vectors for use in the subject methods. The terms "transduced" and "infected" are used interchangeably herein to refer to introduction of the heterologous DNA to the cell in the context of a viral particle.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

As used herein, a "therapeutic" gene refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.); particularly humans.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a therapeutic polypeptide operably linked to a promoter and a polyadenylation sequence consists only of the promoter, polynucleotide sequence encoding the therapeutic polypeptide, and polyadenylation sequence. As another example, a polypeptide "consisting of" a recited sequence contains only the recited amino acid sequence.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Methods and Compositions

In some aspects of the invention, methods and compositions are provided for delivering a polynucleotide to cone photoreceptors. As discussed above, cone photoreceptors, referred to interchangeably herein as "cone cells", "retinal cones", and most simply, "cones," are one of two subtypes of photoreceptor cells in the retina of the eye, the other being rod photoreceptors. Cone photoreceptors may be readily distinguished from rod photoreceptors by a number of physical, biochemical, and functional characteristics. For example, cone photoreceptors comprise an outer segment region that is shaped like a cone, whereas rod photoreceptors comprise an outer segment that is shaped like a rod. Cone photoreceptors express a number of proteins that are not expressed by rod photoreceptors, including, e.g., L-opsin (OPN1LW, the nucleic acid and amino acid sequences for which may be found at GenBank Accession No: NM_020061.5), M-opsin (OPN1MW, the nucleic acid and amino acid sequences for which may be found at GenBank Accession No: NM_000513.2), or S-opsin (OPN1SW, the nucleic acid and amino acid sequences for which may be found at GenBank Accession No: NM_001708.2); whereas rod photoreceptors express a number of proteins that are not expressed by cone photoreceptors, e.g. rhodopsin (RHO, the nucleic acid and amino acid sequences for which may be found at GenBank Accession No: NM_000539.3) and rod-derived cone viability factor (RDCVF, also known as NXNL1, the nucleic acid and amino acid sequences for which may be found at GenBank Accession No:NM_138454.1). Functionally, cone photoreceptors differ from rod photoreceptors in that cone photoreceptors are responsible for color vision and function best in relatively bright light, whereas rod photoreceptors support vision at low light levels and function best in dim light; cones and rods can be distinguished based on this difference using an electroretinogram (ERG) or color ERG (cERG). Finally, cone photoreceptors may be distinguished from rod photoreceptors by their location in the retina. As discussed above, the vast majority of cone photoreceptors—all of them L- and M-cone photoreceptors—are densely packed in a 1.5 mm depression located in the center of the macula of the retina, called the fovea centralis, with the remaining L- and M-cone photoreceptors and the S-cone photoreceptors scattered in the parafovea, the perifovea, and the peripheral retina. In contrast, rod photoreceptors are excluded from the foveola and are poorly represented in the fovea, instead being primarily found in the parafovea, the perifovea, and the peripheral retina.

As discussed above, prior to the present disclosure, it was common understanding in the art that cone photoreceptors—and more particularly, the L- and M-cone photoreceptors in the fovea—were resistant to transduction by AAV delivered from the vitreous. However, as demonstrated by the working examples herein, foveal cones can, in fact, be transduced by intravitreally delivery using the methods and compositions of the present disclosure. In some embodiments, the cone photoreceptors that are transduced by the subject methods and compositions reside anywhere in the retina, i.e. the macula (the foveal centralis, the parafovea, the perifovea), or the periphery. In some embodiments, the cone photoreceptors reside in the fovea centralis. In certain embodiments, the cone photoreceptors are foveal cones, that is, they are L- or M-cones that reside within the fovea, this being the region of the fovea centralis spanning from about 0.175 mm from the center of the fovea centralis to about 0.75 mm from the center of the fovea centralis.

rAAV Virions

In practicing the subject methods, the polynucleotide of interest is delivered to cone photoreceptors by injecting into the vitreous of the eye a recombinant viral particle comprising the polynucleotide of interest as a heterologous sequence within its genome. In some instances, the recombinant viral particles are recombinant adeno-associated virus (rAAV) particles. In some embodiments, the rAAV are of a wild-type serotype; that is, they comprise a viral capsid that consists of viral capsid proteins that occur in nature. In other embodiments, the rAAV are an AAV serotype variant, i.e., they comprise a variant AAV capsid protein, that is, an AAV capsid protein that comprises at least one amino acid difference relative to a corresponding parental AAV capsid protein, e.g. a wild type AAV capsid protein, and does not consist of an amino acid sequence present in a naturally occurring AAV capsid protein.

As demonstrated in the working examples of the present application, rAAV virions comprising a variant AAV capsid protein comprising at least one amino acid difference in the GH loop, or more particularly, in subloop IV of the GH loop, demonstrate an increased infectivity of cone photoreceptors relative to rAAV virions comprising wild type AAV capsid protein when delivered intravitreally. By "increased infectivity," it is meant that the variant rAAV virion is better able to transduce the target cell than the wild type AAV capsid protein. Improvements in the ability of an AAV to transduce a cell can be observed by observing more polynucleotide being delivered to each cell and more cells being transduced in a tissue, resulting in an increase in the amount of polynucleotide delivered to each cell and to the tissue. Accordingly, in some aspects of the invention, methods are provided for the improved delivery of a polynucleotide of interest to cone photoreceptors, the improvement comprising delivering to the vitreous of the eye an effective amount of a rAAV variant, the rAAV variant comprising i) a variant AAV capsid protein that comprises at least one amino acid difference relative to a corresponding parental AAV capsid protein, e.g. a wild type AAV capsid protein, and does not consist of an amino acid sequence present in a naturally occurring AAV capsid protein, and ii) the polynucleotide of interest as a heterologous sequence within the viral genome.

Of particular interest in the subject disclosure are rAAV variants that comprise at least one amino acid difference in the GH loop, or "loop IV", of an AAV capsid protein relative to a corresponding parental AAV capsid protein. By the GH loop, or loop IV, it is meant the loop created between the G and H strands of the jelly-roll β-barrel of the AAV capsid protein VP1, as described in, e.g., Xie et al. (2002) PNAS 99(16):10405-10410, van Vliet et al. (2006) Mol. Ther. 14:809; Padron et al. (2005) J. Virol. 79:5047; and Shen et al. (2007) Mol. Ther. 15:1955. In some instances, the at least one amino acid difference is within subloop 4 of the GH loop, i.e., the solvent-accessible portion of the GH loop, consisting essentially of about amino acids 571-612 of AAV1 VP1 (SEQ ID NO:1), about amino acids 570-611 of AAV2 VP1 (SEQ ID NO:2), about amino acids 571-612 of AAV3 VP1 (SEQ ID NO:3), about amino acids 569-610 of AAV4 VP1 (SEQ ID NO:4), about amino acids 560-601 of AAV5 VP1 (SEQ ID NO:5), about amino acids 571 to 612 of AAV6 VP1 (SEQ ID NO:6), about amino acids 572 to 613 of AAV7 VP1 (SEQ ID NO:7), about amino acids 573 to 614 of AAV8 VP1 (SEQ ID NO:8), about amino acids 571 to 612 of AAV9 VP1 (SEQ ID NO:9), about amino acids 573 to 614 of AAV10 VP1 (SEQ ID NO:10); or about the corresponding amino acid range of a variant thereof. In certain instances, the at least one amino acid difference is within the range of amino acids consisting essentially of amino acids 581-596 of AAV1 VP1, 580-595 of AAV2 VP1, 581-596 of AAV3 VP1, 579-594 of AAV4, 570-585 of AAV5 VP1, 581-596 of AAV6 VP1, 582-597 of AAV7 VP1, 583-598 of AAV8 VP1, 581-596 of AAV9 VP1, 583-598 of AAV10 VP1, or within the corresponding amino acid range of a variant thereof. Those skilled in the art would know, based on a comparison of the amino acid sequences of capsid proteins of various AAV serotypes, where the amino acids "corresponding to amino acids 570-611 of VP1 from AAV2", for example, would be in a capsid protein of any given AAV serotype.

In some embodiments, the at least one amino acid difference is an insertion of a peptide between two amino acids in the GH loop of the AAV capsid protein, e.g. between about amino acids 571-612 of AAV1 VP1 (SEQ ID NO:1), about amino acids 570-611 of AAV2 VP1 (SEQ ID NO:2), about amino acids 571-612 of AAV3 VP1 (SEQ ID NO:3), about amino acids 569-610 of AAV4 VP1 (SEQ ID NO:4), about amino acids 560-601 of AAV5 VP1 (SEQ ID NO:5), about amino acids 571 to 612 of AAV6 VP1 (SEQ ID NO:6), about amino acids 572 to 613 of AAV7 VP1 (SEQ ID NO:7), about amino acids 573 to 614 of AAV8 VP1 (SEQ ID NO:8), about amino acids 571 to 612 of AAV9 VP1 (SEQ ID NO:9), about amino acids 573 to 614 of AAV10 VP1 (SEQ ID NO:10); or about the corresponding amino acid range of a variant thereof; for example, between two amino acids within amino acids 581-596 of AAV1 VP1, 580-595 of AAV2 VP1, 581-596 of AAV3 VP1, 579-594 of AAV4, 570-585 of AAV5 VP1, 581-596 of AAV6 VP1, 582-597 of AAV7 VP1, 583-598 of AAV8 VP1, 581-596 of AAV9 VP1, 583-598 of AAV10 VP1, or within the corresponding amino acid range of a variant thereof. For example, the insertion site can be between amino acids 580 and 581, amino acids 581 and 582, amino acids 582 and 583, amino acids 583 and 584, amino acids 584 and 585, amino acids 585 and 586, amino acids 586 and 587, amino acids 587 and 588, amino acids 588 and 589, amino acids 589 and 590, amino acids 590 and 591, amino acids 591 and 592, amino acids 592 and 593, amino acids 593 and 594, or amino acids 594 and 595 of AAV2 VP1, or the corresponding amino acids in another AAV VP1 or variant thereof.

Of particular interest in some embodiments of the present disclosure are the rAAV variants comprising a peptide insertion as disclosed in PCT Publication No. WO 2012/145601, the full disclosure of which is incorporated herein by reference. These rAAV variants comprise a peptide insert having 5 to 11 amino acids in length, that is, the inserted peptide comprises 5 amino acids, 6 amino acids, 7 amino acids, 8 amino acids, 9 amino acids, 10 amino acids, or 11 amino acids.

One exemplary peptide of particular interest is a peptide of Formula I:

$$Y_1Y_2X_1X_2X_3X_4X_5X_6X_7Y_3Y_4 \quad \text{(SEQ ID NO: 20)}$$

where:
each of Y1-Y4, if present, is independently selected from Ala, Leu, Gly, Ser, and Thr;
X1, if present, is selected from Leu, Asn, and Lys;
X2 is selected from Gly, Glu, Ala, and Asp;
X3 is selected from Glu, Thr, Gly, and Pro;
X4 is selected from Thr, Ile, Gln, and Lys;
X5 is selected from Thr and Ala;
X6 is selected from Arg, Asn, and Thr;
X7, if present, is selected from Pro and Asn.
In certain embodiments, X1 and/or X7 is absent.

A second exemplary peptide of particular interest is a peptide of Formula II:

$$Y_1Y_2X_1X_2X_3X_4X_5X_6X_7Y_3Y_4 \quad \text{(SEQ DI NO: 21)}$$

where:
each of Y1-Y4, if present, is independently selected from Ala, Leu, Gly, Ser, and Thr;
each of X1-X4 is any amino acid;
X5 is Thr
X6 is Arg; and
X7 is Pro.
In certain embodiments, any one or more of Y1-Y4 are absent.

A third exemplary peptide of particular interest is a peptide of Formula III:

$$Y_1Y_2X_1X_2X_3X_4X_5X_6X_7Y_3Y_4 \quad \text{(SEQ ID NO: 22)}$$

where:
each of Y1-Y4, if present, is independently selected from Ala, Leu, Gly, Ser, and Thr;
X1, if present, is selected from Leu and Asn;
X2, if present, is selected from Gly and Glu;
X3 is selected from Glu and Thr;
X4 is selected from Thr and Ile;
X5 is Thr;
X6 is Arg; and
X7 is Pro.
In certain embodiments, any one or more of Y1-Y4, X1 and X2 are absent.

A fourth exemplary peptide of particular interest is a peptide of Formula IV:

$$Y1Y2X1X2X3X4X5X6X7Y3Y4 \quad \text{(SEQ ID NO: 23)}$$

where:
each of Y1-Y4, if present, is independently selected from Ala, Leu, Gly, Ser, and Thr;
X1, if present, is selected from Leu, Asn, Arg, Ala, Ser, and Lys;
X2 is selected from Gly, Glu, Ala, Val, Thr, and Asp;
X3 is selected from Glu, Thr, Gly, Asp, or Pro;
X4 is selected from Thr, Ile, Gly, Lys, Asp, and Gln;
X5 is selected from Thr, Ser, Val, and Ala;
X6 is selected from Arg, Val, Lys, Pro, Thr, and Asn; and
X7 is selected from Pro, Gly, Phe, Asn, and Arg.
In certain embodiments, any one or more of Y1-Y4 and X1 are absent.

Exemplary insertion peptides of particular interest having these formulas include peptides comprising the sequence LGETTRP (SEQ ID NO:11) and NETITRP (SEQ ID NO:12), or variants thereof. In some cases, the insertion peptide has from 1 to 4 spacer amino acids (Y1-Y4) at the amino terminus and/or at the carboxyl terminus. Suitable spacer amino acids include, but are not limited to, leucine, alanine, glycine, and serine. For example, in some cases, an insertion peptide has the amino acid sequence: LALGETTRPA (SEQ ID NO:13); LANETITRPA (SEQ ID NO:14), As another example, in some cases, the insertion peptide has the amino acid sequence AALGETTRPA (SEQ ID NO:15) or AANETITRPA (SEQ ID NO:16), As yet another example, in some cases, an insertion peptide has the amino acid sequence GLGETTRPA (SEQ ID NO:17) or GNETITRPA (SEQ ID NO:18).

In some embodiments, a subject rAAV virion capsid does not include any amino acid substitutions, insertions, or deletions, other than an insertion of from about 5 to 11 amino acids in the GH loop or subregion thereof relative to a corresponding parental AAV capsid protein. In other embodiments, a subject rAAV virion capsid may include from 1 to about 25 amino acid insertions, deletions, or substitutions, compared to the parental AAV capsid protein, in addition to an insertion of from about 5 to 11 amino acids in the GH loop or subregion thereof as described above. For example, a number of amino acid sequence alterations have been disclosed in the art, any of which may be included in the subject rAAV. In some embodiments, a subject rAAV virion capsid is a chimeric capsid, e.g., the capsid comprises a portion of an AAV capsid of a first AAV serotype and a portion of an AAV capsid of a second serotype; and comprises an insertion of from about 5 amino acids to about 11 amino acids in the GH loop or subregion thereof relative to a corresponding parental AAV capsid protein.

In some embodiments, a subject rAAV virion comprises a capsid protein comprising an amino acid sequence having a sequence identity of 80% or more to the VP1 capsid protein of the corresponding parental capsid protein, e.g. 85% or more, 90% or more, 95% or more or 97 C % identity or more to the corresponding parental capsid protein and an insertion of from about 5 to 11 amino acids in the GH loop or subregion thereof relative to a corresponding parental AAV capsid protein. For example a sequence identity of 80% or more to the 7m8 VP1 sequence described in SEQ ID NO:19, e.g. 85% identity or more, 90% identity or more, or 95% identity or more to the 7m8 VP1 sequence, in some instances 97% identity or more, 98% identity or more, or at least about 99% sequence identity to the amino acid sequence provided in SEQ ID NO:19.

rAAV variants that are encompassed by the subject compositions and that find use in the subject methods may be readily validated as such by determining the efficacy by which they transduce cone photoreceptors, e.g. foveal cone photoreceptors. For example, viral particles may be created comprising an AAV viral genome comprising an expression cassette comprising GFP operably linked to a cone promoter as known in the art, packaged into the subject rAAV, and the viral particles injected into the vitreous of a mammalian eye, e.g. the eye of a mouse, rat, rabbit, gerbil, hamster, squirrel, or primate, e.g. non-human primate. rAAV virions encompassed by the present disclosure will typically exhibit at least a 2-fold, at least a 5-fold, at least a 10-fold, at least a 15-fold, at least a 20-fold, at least a 25-fold, at least a 50-fold, in some instances, more than 50-fold, e.g. at least a 60-fold, at least a 70-fold, at least an 80-fold, at least a 90-fold, for example, a 100-fold increased infectivity of cone photoreceptors or more when administered via intravitreal injection as compared to the infectivity of cone photoreceptors by an AAV virion comprising the corresponding parental AAV capsid protein. Put another way, rAAV virions suitable for use in the subject methods will infect at least 10-fold more, at least 15-fold more, at least 20-fold more, at least 50-fold more, in some instances more than 50-fold more cone photoreceptors, e.g. at least 60-fold, at least 70-fold, at least 80-fold, at least 90-fold, for example, a 100-fold more cone photoreceptors than AAV virions comprising the corresponding parental AAV capsid protein.

In some embodiments, the method may further comprise the step of detecting the presence of the delivered polynucleotide in the cone photoreceptor. Any convenient method may be employed for detecting the presence of the polynucleotide. For example, the polynucleotide may be detecting using, e.g., PCR, Next Gen sequencing, and the like, or the expression of a gene product encoded by the polynucleotide may be detected by, e.g., RT-PCR, Northern blot, RNAse protection, Western blot, ELISA, immunohistochemistry, and the like. These methods are particularly suited to preclinical studies. In clinical studies, in may be preferably to detect the presence of the polynucleotide by detecting the presence of a functional gene product, that is, by detecting the impact of the gene product on the viability or function of the cone photoreceptor in the subject. For example, if the gene product encoded by the polynucleotide improves the viability of the cone photoreceptor, an improvement in viability of the cone photoreceptor may be detected by, e.g., fundus photography, Optical coherence tomography (OCT), Adaptive Optics (AO), and the like, as a way of detecting the presence of the polynucleotide. If the gene product encoded by the polynucleotide alters the activity of the cone photoreceptor, the modified activity of the cone photoreceptor may be detected by, e.g., electroretinogram (ERG) and color ERG (cERG); color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, and the like, as a way of detecting the presence of the delivered polynucleotide.

As discussed above, in some embodiments, the polynucleotide that is delivered by the subject compositions and methods is expressed by the cone photoreceptor to which it is delivered. In other words, in some aspects of the invention, methods are provided for expressing a gene product in a cone photoreceptor, the methods comprising delivering to the cone photoreceptor a polynucleotide that encodes the gene product of interest. As will be well understood by the ordinarily skilled artisan, expression by a cone cell of a polynucleotide of interest typically requires that the polynucleotide of interest be operably linked to a promoter. As will also be appreciated by the ordinarily skilled artisan, there are a number of ways in which this can be achieved. For example, the polynucleotide may be delivered to the host cell, i.e. the cone photoreceptor, operatively linked to a promoter. In other words, the viral genome comprising the polynucleotide of interest also comprises a promoter, wherein the promoter is operably linked to the polynucleotide to form an expression cassette. As another example, the polynucleotide may be delivered to the host cell i.e. the cone photoreceptor, flanked by sequences that promoter the integration of the polynucleotide into the host genome. In other words, the viral genome comprising the polynucleotide of interest comprises sequences flanking the polynucleotide of interest that are homologous to sequences flanking the 3' end of a host cell promoter and promote the recombination of the polynucleotide of interest into the host genome such that it is operably linked to the host cell promoter. Other arrangements of the recombinant viral genome that may be employed to ensure the expression of the polynucleotide of interest will be readily envisioned by the ordinarily skilled artisan; see, for example, US Application Publication No. 2013/0280222, the full disclosure of which is incorporated herein by reference.

Accordingly, in some instances, the viral genome comprised by the rAAV comprises a promoter operably linked to the polynucleotide of interest. In some instances, the promoter is a ubiquitous promoter, i.e., it is a promoter that is active in a wide range of cells, tissues and species. In other instances, the promoter is a cone promoter. By a cone promoter it is meant a promoter that is active in cone photoreceptors, i.e., that promotes the expression in cone photoreceptors of a polynucleotide to which it is operably linked. Non-limiting examples of cone promoters that find use in the subject compositions include the pMNTC promoter as disclosed in U.S. Provisional Application Nos. 61/954,330 and 62/127,185; the pR2.1 promoter or variants thereof (e.g. pR1.7, pR1.5, pR1.1, etc.) as disclosed in, e.g., US Application No. 2013/0317091; or the synthetic IRBP/GNAT2 promoter as disclosed in US Application No. 2014/0275231; the full disclosures of which are incorporated herein by reference. In some embodiments, the promoter region comprises, consists essentially of, or consists of the core M-opsin promoter sequence (SEQ ID NO:26); or a functional fragment or variant thereof. In other instances, the viral genome comprised by the rAAV comprises two sequences having homology to a target integration site in the host genome, a first sequence that is homologous to the region 5' of the integration site and located 5' to the polynucleotide on the viral genome, and a second sequence that is homologous to the region 3' of the integration site and located 3' to the polynucleotide on the viral genome, wherein the target integration site is 3' to and operably linked to a host promoter, e.g. a cone promoter, e.g. an L-opsin promoter, an M-opsin promoter. As another example, the subject polynucleotide cassette may comprise an optimized enhancer, optimized promoter, optimized 5'UTR, optimized intron, optimized kozak and optimized polyA region in operable linkage; see, e.g. SEQ ID NO:27. In some embodiments, transduction is enhanced relative to expression as observed when a wild type or other parental capsid is employed. By enhanced, it is meant transduction that is elevated, increased, or augmented for example, at least 2-fold, at least 5-fold, at least 10-fold, at least 15-fold, at least 20-fold, at least 25-fold, at least 50-fold, in some instances, more than 50-fold, e.g. at least 60-fold, at least 70-fold, at least 80-fold, at least 90-fold, for example, 100-fold in a subject's cone photoreceptors over levels that would be observed using a wild type or other parental capsid protein, and usually to an amount to have an impact on cone viability and/or function, e.g. to provide a therapeutic benefit to the subject.

Enhanced transduction of cone cells by the subject variant rAAVs is expected to result in enhanced expression of polynucleotides, e.g., expression cassettes, being delivered to those cells by the variant rAAV. Enhanced expression of a polynucleotide by the rAAVs of the subject disclosure may be observed in a number of ways. For example, enhanced expression may be observed by detecting the expression of the polynucleotide following contact of the variant rAAV to the cone cells sooner, e.g. 7 days sooner, 2 weeks sooner, 3 weeks sooner, 4 weeks sooner, 8 weeks sooner, 12 weeks sooner, or more, than expression would be detected if the polynucleotide were delivered by the parental rAAV. Enhanced expression may also be observed as an increase in the amount of gene product per cell. For example, there may be a 2-fold increase or more, e.g. a 3-fold increase or more, a 4-fold increase or more, a 5-fold increase or more, or a 10-fold increase or more in the amount of gene product per cone cell. Enhanced expression may also be observed as an increase in the number of cone cells that express detectable levels of the polynucleotide carried by the variant rAAV. For example, there may be a 2-fold increase or more, e.g. a 3-fold increase or more, a 4-fold increase or more, a 5-fold increase or more, or a 10-fold increase or more in the number of cone cells that express detectable levels of the polynucleotide. As another example, the polynucleotide of the present invention may promote detectable levels of the polynucleotide in a greater percentage of cells as compared to a parental rAAV; for example, where a parental rAAV may promote detectable levels of polynucleotide expression in, for example, less than 5% of the cone cells in a certain region, the rAAV of the present invention promotes detectable levels of expression in 5% or more of the cone cells in that region; e.g. 10% or more, 15% or more, 20% or more, 25% or more, 30% or more, 35% or more, 40% or more, or 45% or more, in some instances 50% or more, 55% or more; 60% or more, 65% or more, 70% or more, or 75% or more, for example 80% or more, 85% or more, 90% or more, or 95% or more of the cone cells that are contacted, will express detectable levels of gene product. Enhanced expression may also be observed as an alteration in the viability and/or function of the cone cells, e.g. as measured using assessment tools such as fundus photography, OCT, adaptive optics, cERG, color vision tests, visual acuity tests, and the like, as known in the art and as described herein.

In some embodiments, the method may further comprise the step of detecting the expression of the polynucleotide in the cone photoreceptor. In such embodiments, any convenient method as known in the art or described herein may be employed for detecting the expression of the polynucleotide, including, for example, detecting the gene product, i.e., the encoded RNA or protein, e.g., by RT-PCR, Northern blot, RNAse protection, Western blot, ELISA, immunohistochemistry, and the like; detecting the impact of the gene product on the viability of the cone photoreceptor, e.g., by fundus photography, Optical coherence tomography (OCT), Adaptive Optics (AO); or detecting the impact of the gene product on cone function, e.g. electroretinography (ERG), color vision tests, visual acuity tests, etc., any of which may be employed in the subject methods.

rAAV virions comprising the polynucleotide of interest of the present disclosure may be produced using any convenient methodologies, AAV packaging cells, and packaging technology as known to those of skill in the art. For example, an AAV expression vector (that is, a plasmid comprising the rAAV genome as well as elements useful for the cloning of the genomic elements in, e.g. bacteria, e.g. origin of replication, selectable marker, etc.) may be transfected into mammalian producer cells. Also transfected into the mammalian producer cells is an AAV helper construct, i.e. a plasmid comprising AAV REP and CAP coding regions that can be expressed in the producer cell, which complement AAV helper functions absent from the AAV expression vector. The dually-transfected producer cells are then infected by a helper virus, e.g. adenovirus, or transfected with a plasmid comprising helper virus accessory genes that promote AAV vector replication, e.g., regions VA, E2A, E4, so as to promote efficient rAAV virus production. The producer cells are then cultured to produce rAAV, and AAV vectors are purified and formulated using standard techniques known in the art.

As another example, an AAV expression vector may be packaged as a baculovirus and introduced into insect producer cells, e.g. Sf9 cells. Also introduced into the insect cells by another baculovirus are the AAV REP and CAP genes. Baculovirus-being a virus—comprises the genes encoding the accessory functions necessary for efficient rAAV virus production. Accordingly, upon infection of the insect cells by the two baculoviruses, the producer cells can be cultured to produce rAAV, and AAV vectors purified and formulated using standard techniques known in the art.

Examples of these and other methods may be found in, for example, U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

Any convenient host cells used in the art for producing rAAV virions may be employed in the production of the subject vectors, including, for example, mammalian cells, insect cells, microorganisms and yeast, e.g. SF-9, 293, A549, HeLa cells, etc. In some instances, the host cells are packaging cells in which the AAV rep and cap genes are stably maintained in the host cell. In some instances, the host cells are producer cells in which the AAV vector genome is stably maintained and packaged.

Pharmaceutical Compositions and Unit Dosages

In some embodiments, e.g. gene therapy uses, it will be desirable to formulate the subject rAAV as a pharmaceutical composition. In certain embodiments, a pharmaceutical composition comprises a vector or virion (e.g., rAAV) described herein and one or more pharmaceutically acceptable carriers, diluents or excipients. Pharmaceutical compositions suitable for use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof In one embodiment, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions of the subject disclosure encompass any pharmaceutically acceptable salts, esters, or salts of such esters, or any other compound which, upon administration to an animal comprising a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bio-equivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salt" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" comprises a pharmaceutically acceptable salt of an acid form of one of the components of the compositions of the invention. These comprise organic or inorganic acid salts of the amines. Preferred acid salts are the hydrochlorides, acetates, salicylates, nitrates and phosphates. Other suitable pharmaceutically acceptable salts are well known to those skilled in the art and comprise basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in Nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and comprise alkaline, alkaline earth, ammonium and quaternary ammonium cations. Carbonates or hydrogen carbonates are also possible. For oligonucleotides, preferred examples of pharmaceutically acceptable salts comprise but are not limited to: (I) salts formed with cations such as sodium, potassium, ammonium, magnesium, calcium, polyamides such as spermine and spermidine, and the like; (II) acid addition salts formed with inorganic acids, for example hydrochloric acid, hydrobromic acid, sulfuric acid, phosphoric acid, nitric acid and the like; (Ill) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, napthalenesulfonic acid, methanesulfonic acid, p-toluenesulfonic acid, naphthalene-disulfonic acid, polygalacturonic acid, and the like; and (IV) salts formed from elemental anions such as chlorine, bromine, and iodine.

Pharmaceutical compositions of the present invention comprise, but are not limited to, solutions, emulsions, and liposome-containing formulations. These compositions may be generated from a variety of components that comprise, but are not limited to, preformed liquids, self-emulsifying solids and self-emulsifying semisolids.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extra circulatory reservoirs, presumably due to competition between the carrier compound and the nucleic acid for a common receptor. For example, the recovery of a partially phosphorothioate oligonucleotide in hepatic tissue can be reduced when it is co-administered with polyinosinic acid, dextran sulphate, polycytidic acid or 4-acetamido-4'isothiocyano-stilbene-2,2'disulfonic acid (Miyao et al., Antisense Res. Dev., 1995, 5, 115-121; Takakura et al., Antisense & Nucl. Acid Drug Dev., 1996, 6, 177-183).

The subject recombinant AAV can be incorporated into pharmaceutical compositions for administration to mammalian patients, particularly humans. The virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some embodiments, the pharmaceutical composition provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

In some embodiments, the pharmaceutical composition provided herein comprises substances which increase the viscosity of the suspension, such as sodium carboxymethyl cellulose, sorbitol, or dextran, in the amount about 1-10 percent, such as 1, 2, 3, 4, 5, 6, 7, 8, 9, or 10 percent.

The pharmaceutical compositions can be included in a container, pack, or dispenser together with instructions for administration.

In some instances, e.g. for administration intraocularly, orally, or parentally, it may be especially advantageous to formulate the pharmaceutical composition in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In some cases, the unit dose of the pharmaceutical composition of the disclosure may be measured as pfu (plaque forming units). In some cases, the pfu of the unit dose of the pharmaceutical composition of the disclosure may be about $1 \times 10^8$ to about $5 \times 10^{10}$ pfu. In some cases, the pfu of the unit dose of the pharmaceutical composition of the disclosure is at least about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu. In some cases, the pfu of the unit dose of the pharmaceutical composition of the disclosure is at most about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu.

In some cases, the viral vector of the disclosure may be measured as vector genomes. In some cases, the unit dose of the pharmaceutical composition of the disclosure is $1 \times 10^8$ vector genomes or more, e.g. $1 \times 10^9$, $1 \times 10^{10}$, $1 \times 10^{11}$, $1 \times 10^{12}$, or $1 \times 10^{13}$ vector genomes or more, in certain instances, $1 \times 10^{14}$ vector genomes or more, and usually no more than $1 \times 10^{15}$ vector genomes. In some embodiments, the unit dose of the pharmaceutical composition of the disclosure is at most about $1 \times 10^{15}$ vector genomes, e.g. $1 \times 10^{14}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes, and typically no less than $1 \times 10^8$ vector genomes. In some cases, the unit dose of the pharmaceutical composition of the disclosure is $1 \times 10^{10}$ to $1 \times 10^{11}$ vector genomes. In some cases, the unit dose of the pharmaceutical composition of the disclosure is $1 \times 10^{10}$ to $3 \times 10^{12}$ vector genomes. In some cases, the unit dose of the pharmaceutical composition of the disclosure is $1 \times 10^9$ to $3 \times 10^{13}$ vector genomes. In some cases, the unit dose of the pharmaceutical composition of the disclosure is $1 \times 10^8$ to $3 \times 10^{14}$ vector genomes.

In some cases, the unit dose of the pharmaceutical composition of the disclosure may be measured using multiplicity of infection (MOI). In some cases, MOI may refer to the ratio, or multiple of vector or viral genomes to the cells to which the nucleic may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI.

In some aspects, the pharmaceutical composition comprises about $1 \times 10^8$ to about $1 \times 10^{15}$ recombinant viruses, about $1 \times 10^9$ to about $1 \times 10^{14}$ recombinant viruses, about $1 \times 10^{10}$ to about $1 \times 10^{13}$ recombinant viruses, about $1 \times 10^{109}$ to about $3 \times 10^{12}$ recombinant viruses, or about $1 \times 10^{11}$ to about $3 \times 10^{12}$ recombinant viruses.

Methods of Administration

The pharmaceutical composition of the present invention may be administered to the eye of the subject by any convenient method, e.g. intraocularly, intravenously, intraperitoneally, etc. In some instances, the administration is intraocular, e.g. by intravitreal injection or subretinal injection. The general methods for delivering a vector via intravitreal injection or via subretinal injection may be illustrated by the following brief outlines. These examples are merely meant to illustrate certain features of the methods, and are in no way meant to be limiting.

In preferred embodiments, the subject rAAV is delivered intravitreally. For intravitreal administration, the vector can be delivered in the form of a suspension. Initially, topical anesthetic is applied to the surface of the eye followed by a topical antiseptic solution. The eye is held open, with or without instrumentation, and the vector is injected through the sclera with a short, narrow, for example a 30 gauge needle, into the vitreous cavity of the eye of a subject under direct observation. Intravitreal administration is generally well tolerated. At the conclusion of the procedure, there is sometimes mild redness at the injection site. There is occasional tenderness, but most patients do not report any pain. No eye patch or eye shield is necessary after this procedure, and activities are not restricted. Sometimes, an antibiotic eye drop is prescribed for several days to help prevent infection.

In some embodiments, the subject rAAV is delivered subretinally. For subretinal administration, the vector can be delivered in the form of a suspension injected subretinally under direct observation using an operating microscope. This procedure may involve vitrectomy followed by injection of vector suspension using a fine cannula through one or more small retinotomies into the subretinal space.

Briefly, an infusion cannula can be sutured in place to maintain a normal globe volume by infusion (of e.g. saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g. saline) creates space to accommodate the intraocular injection of vector, and (3) its controlled removal reduces the possibility of retinal tears and unplanned retinal detachment.

In practicing the subject methods, the subject rAAV virion is delivered to the eye in an amount effective to deliver the polynucleotide of interest to 5% or more of the subject's cone photoreceptors, for example, 10% or more, 20% or more, 30% or more, 40% or more, or 50% or more of the subject's cone photoreceptors, e.g. 60% or more, 70% or more, 80% or more, or 90% or more of the subject's cone photoreceptors, in some instance, 95% or more, 98% or more, or 100% of the subject's cone photoreceptors to provide therapeutic benefit to the subject individual. Put another way, following the administering, 5% or more of the subject's cone photoreceptors, e.g. 10% or more, 20% or more, 30% or more, 40% or more, or 50% or more, in some instance 60% or more, 70% or more, 80% or more, or 90% or more, e.g. 95%, 98%, or 100% of the cones, will comprise a sufficient amount of the polynucleotide of interest to have an impact on cone viability and/or function, e.g. to treat or prevent a disorder. In some embodiments, the transduced cones photoreceptors will be located throughout the retina. In some embodiments, the transduced cone photoreceptors will be cones in the fovea and foveola. In some embodiments, the transduced cone photoreceptors will be foveal cones, i.e. L- or M-cones located in the fovea.

Typically, an effective amount will be about $1\times10^8$ vector genomes or more of the subject rAAV, e.g. $1\times10^9$, $1\times10^{10}$, $1\times10^{11}$, $1\times10^{12}$, or $1\times10^{13}$ vector genomes or more, in certain instances, $1\times10^{14}$ vector genomes or more, and usually no more than $1\times10^{15}$ vector genomes. In some cases, the amount of vector genomes that is delivered is at most about $1\times10^{15}$ vector genomes, e.g. $1\times10^{14}$ vector genomes or less, for example $1\times10^{13}$, $1\times10^{12}$, $1\times10^{11}$, $1\times10^{10}$, or $1\times10^9$ vector genomes or less, in certain instances $1\times10^8$ vector genomes, and typically no less than $1\times10^8$ vector genomes. In some cases, the amount of vector genomes that is delivered is $1\times10^{10}$ to $1\times10^{11}$ vector genomes. In some cases, the amount of vector genomes that is delivered is $1\times10^{10}$ to $3\times10^{12}$ vector genomes. In some cases, the amount of vector genomes that is delivered is $1\times10^9$ to $3\times10^{13}$ vector genomes. In some cases, the amount of vector genomes that is delivered is $1\times10^8$ to $3\times10^{14}$ vector genomes.

In some cases, the amount of pharmaceutical composition to be administered may be measured using multiplicity of infection (MOI). In some cases, MOI may refer to the ratio, or multiple of vector or viral genomes to the cells to which the nucleic may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of the disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI. In some cases, recombinant viruses of the disclosure are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects, the amount of pharmaceutical composition comprises about $1\times10^8$ to about $1\times10^{15}$ recombinant viruses, about $1\times10^9$ to about $1\times10^{14}$ recombinant viruses, about $1\times10^{10}$ to about $1\times10^{13}$ recombinant viruses, about $1\times10^{10}$ to about $3\times10^{12}$ recombinant viruses, or about $1\times10^{11}$ to about $3\times10^{12}$ recombinant viruses.

Utility

Methods and compositions for the intravitreal delivery of polynucleotides to cone photoreceptors, and more particular foveal cones, find many uses in research and in medicine.

For example, such methods and compositions may be used in research to test the function of the gene product encode by the polynucleotide in vivo, e.g. to better understand the function of the cone photoreceptor and/or whether the gene product will impact the viability and/or function of the cone photoreceptor.

As alluded to above, the subject rAAVs, referred to collectively herein as "subject compositions", find use in expressing a transgene in cone cells of an animal, for example, in foveal cones of an animal. For example, the subject compositions may be used in research, e.g. to determine the effect that the gene has on cone cell viability and/or function. As another example, the subject compositions may be used in medicine, e.g. to treat a cone cell disorder. Thus, in some aspects of the invention, methods are provided for the expression of a gene in cone cells, the method comprising contacting cone cells with a composition of the present disclosure. In some embodiments, contacting occurs in vitro. In some embodiments, contacting occurs in vivo, i.e., the subject composition is administered to a subject.

For instances in which cone cells are to be contacted in vitro with a subject rAAV, the cells may be from any mammalian species, e.g. rodent (e.g. mice, rats, gerbils, squirrels), rabbit, feline, canine, goat, ovine, pig, equine, bovine, primate, human. Cells may be from established cell lines, e.g. WERI cells, 661W cells, or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from a mammal by any convenient method, e.g. whole explant, biopsy, etc. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To promote expression of the transgene, the subject rAAV will be contacted with the cells for about 30 minutes to 24 hours or more, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, 24 hours, etc. The subject rAAV may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. Contacting the cells may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Typically, an effective amount of subject rAAV is provided to produce the expression of the transgene in cells. As discussed elsewhere herein, the effective amount may be readily determined empirically, e.g. by detecting the presence or levels of transgene gene product, by detecting an effect on the viability or function of the cone cells, etc. Typically, an effect amount of subject rAAV will promote greater expression of the transgene in cone cells than the same amount of parental rAAV from which its capsid was derived. Typically, expression will be enhanced 2-fold or more relative to the expression from parental rAAV, for example 3-fold, 4-fold, or 5-fold or more, in some instances 10-fold, 20-fold or 50-fold or more, e.g. 100-fold.

In some embodiments, as when the transgene is a selectable marker, the population of cells may be enriched for those comprising the transgene by separating the modified cells from the remaining population. Separation may be by any convenient separation technique appropriate for the selectable marker used. For example, if the transgene is a fluorescent marker, cells may be separated by fluorescence activated cell sorting, whereas if the transgene is a cell surface marker, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the cells. Cell compositions that are highly enriched for cells comprising the transgene are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

For instances in which cone cells are to be contacted in vivo with the subject rAAV, the subject may be any mammal, e.g. rodent (e.g. mice, rats, gerbils), rabbit, feline, canine, goat, ovine, pig, equine, bovine, or primate. In certain embodiments, the subject is a primate of the Parvorder Catarrhini. As is known in the art, Catarrhini is one of the two subdivisions of the higher primates (the other being the New World monkeys), and includes Old World monkeys and the apes, which in turn are further divided into the lesser apes or gibbons and the great apes, consisting of the orangutans, gorillas, chimpanzees, bonobos, and humans. In a further preferred embodiment, the primate is a human.

The subject rAAV may be administered to the retina of the subject by any suitable method. For example, the subject composition may be administered intraocularly via intravitreal injection or subretinal injection. The general methods for delivering a vector via intravitreal injection or via subretinal injection may be illustrated by the following brief outlines. These examples are merely meant to illustrate certain features of the methods, and are in no way meant to be limiting.

For subretinal administration, the subject rAAV can be delivered in the form of a suspension injected subretinally under direct observation using an operating microscope. Typically, a volume of 1 to 200 uL, e.g. 50 uL, 100 uL, 150 ul, or 200 uL, but usually no more than 200 uL, of the subject composition will be administered by such methods. This procedure may involve vitrectomy followed by injection of vector suspension using a fine cannula through one or more small retinotomies into the subretinal space. Briefly, an infusion cannula can be sutured in place to maintain a normal globe volume by infusion (of e.g. saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g. saline) creates space to accommodate the intraocular injection of vector, and (3) its controlled removal reduces the possibility of retinal tears and unplanned retinal detachment.

For intravitreal administration, the subject rAAV can be delivered in the form of a suspension. Initially, topical anesthetic is applied to the surface of the eye followed by a topical antiseptic solution. The eye is held open, with or without instrumentation, and the rAAV is injected through the sclera with a short, narrow, for example a 30 gauge needle, into the vitreous cavity of the eye of a subject under direct observation. Typically, a volume of 1 to 100 uL, e.g. 25 uL, 50 uL, or 100 uL, and usually no more than 100 uL, of the subject composition may be delivered to the eye by intravitreal injection without removing the vitreous. Alternatively, a vitrectomy may be performed, and the entire volume of vitreous gel is replaced by an infusion of the subject composition. In such cases, up to about 4 mL of the subject composition may be delivered, e.g. to a human eye. Intravitreal administration is generally well tolerated. At the conclusion of the procedure, there is sometimes mild redness at the injection site. There is occasional tenderness, but most patients do not report any pain. No eye patch or eye shield is necessary after this procedure, and activities are not restricted. Sometimes, an antibiotic eye drop is prescribed for several days to help prevent infection.

The subject methods and/or compositions may be used in medicine to express a therapeutic polynucleotide in cone photoreceptors as a therapy to treat or prevent a retinal disorder. The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

There are a number of retinal disorders that may be treated or prevented using the subject methods and/or compositions. Of particular interest are cone-associated disorders; that is, disorders that are associated with a loss of cone viability and/or a reduction in cone function. As discussed above, cone photoreceptors are responsible for color vision and high acuity foveal vision, and are densely packed in a 1.5 mm depression located in the center of the macula of the retina, called the fovea centralis. Consistent with this, disorders associated with cone dysfunction and viability typically manifest in the macula and impact color vision and high acuity vision. Non-limiting examples of cone-associated disorders include rod-cone dystrophy; cone-rod dystrophy; progressive cone dystrophy; retinitis pigmentosa (RP); Stargardt Disease; macular telangiectasia, Leber hereditary optic neuropathy, Best's disease; adult vitelliform macular dystrophy; X-linked retinoschisis; color vision disorders such as blue cone monochromacy, achromatopsia, incomplete achromatopsia, protan defects, deutan defects, and tritan defects; and retinal disorders that affect the central macula, such as, for example, age-related macular degeneration, wet age-related macular degeneration, geographic atrophy, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis.

Stargardt's Macular Dystrophy.

Stargardt's macular dystrophy, also known as Stargardt Disease and fundus flavimaculatus, is an inherited form of juvenile macular degeneration that causes progressive vision loss usually to the point of legal blindness. The onset of symptoms usually appears between the ages of six and thirty years old (average of about 16-18 years). Mutations in several genes, including ABCA4, CNGB3, ELOVL4, PROM1, are associated with the disorder. Symptoms typically develop by twenty years of age, and include wavy vision, blind spots, blurriness, impaired color vision, and difficulty adapting to dim lighting. The main symptom of Stargardt disease is loss of visual acuity, which ranges from 20/50 to 20/200. In addition, those with Stargardt disease are sensitive to glare; overcast days offer some relief. Vision is most noticeably impaired when the macula is damaged, which can be observed by fundus exam.

Cone Dystrophy.

Cone dystrophy (COD) is an inherited ocular disorder characterized by the loss of cone cells. The most common symptoms of cone dystrophy are vision loss (age of onset ranging from the late teens to the sixties), sensitivity to bright lights, and poor color vision. Visual acuity usually deteriorates gradually, but it can deteriorate rapidly to 20/200; later, in more severe cases, it drops to "counting fingers" vision. Color vision testing using color test plates (HRR series) reveals many errors on both red-green and blue-yellow plates. It is believed that the dystrophy is primary, since subjective and objective abnormalities of cone function are found before ophthalmoscopic changes can be seen. However, the retinal pigment epithelium (RPE) rapidly becomes involved, leading to a retinal dystrophy primarily involving the macula. The fundus exam via ophthalmoscope is essentially normal early on in cone dystrophy, and definite macular changes usually occur well after visual loss. The most common type of macular lesion seen during ophthalmoscopic examination has a bull's-eye appearance and consists of a doughnut-like zone of atrophic pigment epithelium surrounding a central darker area. In another, less frequent form of cone dystrophy there is rather diffuse atrophy of the posterior pole with spotty pigment clumping in the macular area. Rarely, atrophy of the choriocapillaris and larger choroidal vessels is seen in patients at an early stage. Fluorescein angiography (FA) is a useful adjunct in the workup of someone suspected to have cone dystrophy, as it may detect early changes in the retina that are too subtle to be seen by ophthalmoscope. Because of the wide spectrum of fundus changes and the difficulty in making the diagnosis in the early stages, electroretinography (ERG) remains the best test for making the diagnosis. Abnormal cone function on the ERG is indicated by a reduced single-flash and flicker response when the test is carried out in a well-lit room (photopic ERG). Mutations in several genes, including GUCA1A, PDE6C, PDE6H, and RPGR, are associated with the disorder.

Cone-Rod Dystrophy.

Cone-rod dystrophy (CRD, or CORD) is an inherited retinal dystrophy that belongs to the group of pigmentary retinopathies. CRD is characterized by retinal pigment deposits visible on fundus examination, predominantly localized to the macular region and the loss of both cone and rod cells. In contrast to rod-cone dystrophy (RCD) resulting from the primary loss in rod photoreceptors and later followed by the secondary loss in cone photoreceptors, CRD reflects the opposite sequence of events: primary cone involvement, or, sometimes, by concomitant loss of both cones and rods. Symptoms include decreased visual acuity, color vision defects, photoaversion and decreased sensitivity in the central visual field, later followed by progressive loss in peripheral vision and night blindness. Mutations in several genes, including ADAM9, PCDH21, CRX, GUCY2D, PITPNM3, PROM1, PRPH2, RAX2, RIMS1, RPGR, and RPGRIP1, are associated with the disorder.

Spinocerebellar Ataxia Type 7.

Spinocerebellar ataxia is a progressive, degenerative, inherited disease characterized by slowly progressive incoordination of gait and is often associated with poor coordination of hands, speech, and eye movements. There are multiple types of SCA, with Spinocerebellar ataxia type 7 (SCA-7) differing from most other SCAs in that visual problems can occur in addition to poor coordination. SCA-7 is associated with automosmal dominant mutations in the ATXN7/SCA7 gene. When the disease manifests itself before age 40, visual problems rather than poor coordination are typically the earliest signs of disease. Early symptoms include difficulty distinguishing colors and decreased central vison. In addition, symptoms of ataxia (incoordination, slow eye movements, and mild changes in sensation or reflexes) may be detectable. Loss of motor control, unclear speech, and difficulty swallowing become prominent as the disease progresses.

Bardet-Biedl Syndrome-1.

Bardet-Biedl syndrome-1 (BBS-1) is a pleiotropic disorder with variable expressivity and a wide range of clinical variability observed both within and between families. The main clinical features are rod-cone dystrophy, with childhood-onset visual loss preceded by night blindness; postaxial polydactyly; truncal obesity that manifests during infancy and remains problematic throughout adulthood; specific learning difficulties in some but not all individuals; male hypogenitalism and complex female genitourinary malformations; and renal dysfunction, a major cause of morbidity and mortality. Vision loss is one of the major features of Bardet-Biedl syndrome. Problems with night vision become apparent by mid-childhood, followed by blind spots that develop in the peripheral vision. Over time, these blind spots enlarge and merge to produce tunnel vision. Most people with Bardet-Biedl syndrome also develop blurred central vision (poor visual acuity) and become legally blind by adolescence or early adulthood. Bardet-Biedl syndrome can result from mutations in at least 14 different genes (often called BBS genes) known or suspected to play critical roles in cilia function, with mutations in BBS1 and BBS10 being the most common.

Achromatopsia.

Achromatopsia, or Rod monochromatism, is a disorder in which subjects experience a complete lack of the perception of color, such that the subject sees only in black, white, and shades of grey. Other symptoms include reduced visual acuity, photophobia, nystagmus, small central scotoma, and eccentric fixation. The disorder is frequently noticed first in children around six months of age by their photophobic activity and/or their nystagmus. Visual acuity and stability of the eye motions generally improve during the first 6-7 years of life (but remain near 20/200). Mutations in CNGB3, CNGA3, GNAT2, PDE6C, and PDE6HI have been associated with the disorder.

Incomplete Achromatopsia.

Incomplete achromatopsia is similar to Achromatopsia but with less penetrance. In incomplete achromatopsia, the symptoms are similar to those of complete achromatopsia except in a diminished form. Individuals with incomplete achromatopsia have reduced visual acuity with or without nystagmus or photophobia. Furthermore, these individuals show only partial impairment of cone cell function but again have retained rod cell function.

Blue Cone Monochromacy.

Blue cone (S cone) monochromatism (BCM) is a rare X-linked congenital stationary cone dysfunction syndrome, affecting approximately 1 in 100,000 individuals. Affected males with BCM have no functional long wavelength sensitive (L) or medium wavelength sensitive (M) cones in the retina, due to mutations at the genetic locus for the L and M-opsin genes. Color discrimination is severely impaired from birth, and vision is derived from the remaining preserved S cones and rod photoreceptors. BCM typically presents with reduced visual acuity (6/24 to 6/60), pendular nystagmus, photophobia, and patients often have myopia. The rod-specific and maximal electroretinogram (ERG) usually show no definite abnormality, whereas the 30 Hz cone ERG cannot be detected. Single flash photopic ERG is often recordable, albeit small and late, and the S cone ERG is well preserved.

Color Vision Deficiency.

Color vision deficiency (CVD), or color blindness, is the inability or decreased ability to see color, or perceive color differences, under normal lighting conditions. Individuals suffering from color blindness may be identified as such using any of a number of color vision tests, e.g., color ERG (cERG), pseudoisochromatic plates (Ishihara plates, Hardy-Rand-Ritter polychromatic plates), the Farnsworth-Munsell 100 hue test, the Farnsworth's panel D-15, the City University test, Kollner's rule, etc. Examples of color vision deficiencies include protan defects, deutan defects, and tritan defects. Protan defects include protanopia (an insensitivity to red light) and protanomaly (a reduced sensitivity to red light), and are associated with mutations in the L-Opsin gene (OPN1LW). Deutan defects include deuteranopia (an insensitivity to green light) and deutanomaly (a reduced sensitivity to green light), and are associated with mutations in the M-Opsin gene (OPN1MW). Tritan defects include tritanopia (an insensitivity to blue light) and tritanomaly (a reduced sensitivity to blue light), and are associated with mutations in the S-Opsin gene (OPN1SW).

Age-Related Macular Degeneration.

Age-related macular degeneration (AMD) is one of the leading causes of vision loss in people over the age of 50 years. AMD mainly affects central vision, which is needed for detailed tasks such as reading, driving, and recognizing faces. The vision loss in this condition results from a gradual deterioration of photoreceptors in the macula. Side (peripheral) vision and night vision are generally not affected.

Researchers have described two major types of age-related macular degeneration, known as the dry, or "non-exudative" form, and the wet, or "exudative" or "neovascular", form, both of which may be treated by delivering transgenes packaged in the subject rAAV.

Dry AMD is characterized by a buildup of yellow deposits called drusen between the retinal pigment epithelium and the underlying choroid of the macula, which may be observed by Fundus photography. This results in a slowly progressive loss of vision. The condition typically affects vision in both eyes, although vision loss often occurs in one eye before the other. Other changes may include pigment changes and RPE atrophy. For example, in certain cases called central geographic atrophy, or "GA", atrophy of the retinal pigment epithelial and subsequent loss of photoreceptors in the central part of the eye is observed. Dry AMD has been associated with mutations in CD59 and genes in the complement cascade.

Wet AMD is a progressed state of dry AMD, and occurs in abut 10% of dry AMD patients. Pathological changes include retinal pigment epithelial cells (RPE) dysfunction, fluid collecting under the RPE, and choroidal neovascularization (CNV) in the macular area. Fluid leakage, RPE or neural retinal detachment and bleeding from ruptured blood vessels can occur in severe cases. Symptoms of wet AMD may include visual distortions, such as straight lines appearing wavy or crooked, a doorway or street sign looking lopsided, or objects appearing smaller or farther away than they really are; decreased central vision; decreased intensity or brightness of colors; and well-defined blurry spot or blind spot in the field of vision. Onset may be abrupt and worsen rapidly. Diagnosis may include the use of an Amsler grid to test for defects in the subject's central vision (macular degeneration may cause the straight lines in the grid to appear faded, broken or distorted), fluorescein angiogram to observe blood vessel or retinal abnormalities, and optical coherence tomography to detect retina swelling or leaking blood vessels. A number of cellular factors have been implicated in the generation of CNV, among which are vascular endothelial growth factor (VEGF), platelet-derived growth factor (PDGF), pigment epithelium-derived factor (PEDF), hypoxia inducible factor (HIF), angiopoietin (Ang), and other cytokines, mitogen-activated protein kinases (MAPK) and others.

Macular Telangiectasia.

Macular telangiectasia (MacTel) is a form of pathologically dilated blood vessels (telangiectasia) in the parafoveal region of the macula. The tissue deteriorates and the retinal structure becomes scarred due to the development of liquid-filled cysts, which impairs nutrition of the photoreceptor cells and destroys vision permanently. There are two types of MacTel, type 1 and type 2. Macular telangiectasia type 2 is a bilateral disease, whose prevalence has recently been shown to be as high as 0.1% in persons 40 years and older. Biomicroscopy may show reduced retinal transparency, crystalline deposits, mildly ectatic capillaries, blunted venules, retinal pigment plaques, foveal atrophy, and neovascular complexes. Fluorescein angiography shows telangiectatic capillaries predominantly temporal to the foveola in the early phase and a diffuse hyperfluorescence in the late phase. High-resolution optical coherence tomography (OCT) may reveal disruption of the photoreceptor inner segment-outer segment border, hyporeflective cavities at the level of the inner or outer retina, and atrophy of the retina in later stages. In Type 1 macular telangiectasia, the disease almost always occurs in one eye, which differentiates it from Type 2. While MacTel does not usually cause total blindness, it commonly causes loss of the central vision, which is required for reading and driving vision, over a period of 10-20 years.

Retinitis Pigmentosa.

Retinitis Pigmentosa (RP) is a group of inherited disorders characterized by progressive peripheral vision loss and night vision difficulties (nyctalopia) that can lead to central vision loss. Presenting signs and symptoms of RP vary, but the classic ones include nyctalopia (night blindness, most commonly the earliest symptom in RP); visual loss (usually peripheral, but in advanced cases, central visual loss); and photopsia (seeing flashes of light). Because RP is a collection of many inherited diseases, significant variability exists in the physical findings. Ocular examination involves assessment of visual acuity and pupillary reaction, as well as anterior segment, retinal, and funduscopic evaluation. In some instances, the RP is one aspect of a syndrome, e.g. syndromes that are also associated with hearing loss (Usher syndrome, Waardenburg syndrome, Alport syndrome, Refsum disease); Kearns-Sayre syndrome (external ophthalmoplegia, lid ptosis, heart block, and pigmentary retinopathy); Abetalipoproteinemia (Fat malabsorption, fat-soluble vitamin deficiencies, spinocerebellar degeneration, and pigmentary retinal degeneration); mucopolysaccharidoses (eg, Hurler syndrome, Scheie syndrome, Sanfilippo syndrome); Bardet-Biedl syndrome (Polydactyly, truncal obesity, kidney dysfunction, short stature, and pigmentary retinopathy); and neuronal ceroid lipofuscinosis (Dementia, seizures, and pigmentary retinopathy; infantile form is known as Jansky-Bielschowsky disease, juvenile form is Vogt-Spielmeyer-Batten disease, and adult form is Kufs syndrome). Retinitis pigmentosa is most commonly associated with mutations in the RHO, RP2, RPGR, RPGRIP1, PDE6A, PDE6B, MERTK, PRPH2, CNGB1, USH2A, ABCA4, BBS genes.

Diabetic Retinopathy.

Diabetic retinopathy (DR) is damage to the retina caused by complications of diabetes, which can eventually lead to blindness. Without wishing to be bound by theory, it is believed that hyperglycemia-induced intramural pericyte death and thickening of the basement membrane lead to incompetence of the vascular walls. These damages change the formation of the blood-retinal barrier and also make the retinal blood vessels become more permeable.

There are two stages of diabetic retinopathy: non-proliferative diabetic retinopathy (NPDR), and proliferative diabetic retinopathy (PDR). Nonproliferative diabetic retinopathy is the first stage of diabetic retinopathy, and is diagnosed by fundoscopic exam and coexistent diabetes. In cases of reduced vision, fluorescein angiography may be done to visualize the vessles in the back of the eye to and any retinal ischemia that may be present. All people with diabetes are at risk for developing NPDR, and as such, would be candidates for prophylactic treatment with the subject vectors. Proliferative diabetic retinopathy is the second stage of diabetic retinopathy, characterized by neovascularization of the retina, vitreous hemorrhage, and blurred vision. In some instances, fibrovascular proliferation causes tractional retinal detachment. In some instances, the vessels can also grow into the angle of the anterior chamber of the eye and cause neovascular glaucoma. Individuals with NPDR are at increased risk for developing PDR, and as such, would be candidates for prophylactic treatment with the subject vectors.

Diabetic Macular Edema.

Diabetic macular edema (DME) is an advanced, vision-limiting complication of diabetic retinopathy that affects nearly 30% of patients who have had diabetes for at least 20 years, and is responsible for much of the vision loss due to DR. It results from retinal microvascular changes that compromise the blood-retinal barrier, causing leakage of plasma constituents into the surrounding retina and, consequently, retinal edema. Without wishing to be bound by theory, it is believed that hyperglycemia, sustained alterations in cell signaling pathways, and chronic microvascular inflammation with leukocyte-mediated injury leads to chronic retinal microvascular damage, which triggers an increase in intraocular levels of VEGF, which in turn increases the permeability of the vasculature.

Patients at risk for developing DME include those who have had diabetes for an extended amount of time and who experience one or more of severe hypertension (high blood pressure), fluid retention, hypoalbuminemia, or hyperlipidemia. Common symptoms of DME are blurry vision, floaters, double vision, and eventually blindness if the condition is allowed to progress untreated. DME is diagnosed by funduscopic examination as retinal thickening within 2 disc diameters of the center of the macula. Other methods that may be employed include Optical coherence tomography (OCT) to detect retinal swelling, cystoid edema, and serous retinal detachment; fluorescein angiography, which distinguishes and localizes areas of focal versus diffuse leakage, thereby guiding the placement of laser photocoagulation if laser photocoagulation is to be used to treat the edema; and color stereo fundus photographs, which can be used to evaluate long-term changes in the retina. Visual acuity may also be measured, especially to follow the progression of macular edema and observe its treatment following administration of the subject pharmaceutical compositions.

Retinal Vein Occlusions.

A retinal vein occlusion (RVO) is a blockage of the portion of the circulation that drains the retina of blood. The blockage can cause back-up pressure in the capillaries, which can lead to hemorrhages and also to leakage of fluid and other constituents of blood.

Glaucoma.

Glaucoma is a term describing a group of ocular (eye) disorders that result in optic nerve damage, often associated with increased fluid pressure in the eye (intraocular pressure) (IOP). The disorders can be roughly divided into two main categories, "open-angle" and "closed-angle" (or "angle closure") glaucoma. Open-angle glaucoma accounts for 90% of glaucoma cases in the United States. It is painless and does not have acute attacks. The only signs are gradually progressive visual field loss, and optic nerve changes (increased cup-to-disc ratio on fundoscopic examination). Closed-angle glaucoma accounts for less than 10% of glaucoma cases in the United States, but as many as half of glaucoma cases in other nations (particularly Asian countries). About 10% of patients with closed angles present with acute angle closure crises characterized by sudden ocular pain, seeing halos around lights, red eye, very high intraocular pressure (>30 mmHg), nausea and vomiting, suddenly decreased vision, and a fixed, mid-dilated pupil. It is also associated with an oval pupil in some cases. Modulating the activity of proteins encoded by DLK, NMDA, INOS, CASP-3, Bcl-2, or Bcl-xl may treat the condition.

Sorsby's Fundus Dystrophy.

Sorsby's fundus dystrophy is an autosomal dominant, retinal disease associated with mutations in the TIMP3 gene. Clinically, early, mid-peripheral, drusen and colour vision deficits are found. Some patients complain of night blindness. Most commonly, the presenting symptom is sudden acuity loss, manifest in the third to fourth decades of life, due to untreatable submacular neovascularisation. Histologically, there is accumulation of a confluent lipid containing material 30 μm thick at the level of Bruch's membrane.

Vitelliform Macular Dystrophy.

Vitelliform macular dystrophy is a genetic eye disorder that can cause progressive vision loss. Vitelliform macular dystrophy is associated with the buildup of fatty yellow pigment (lipofuscin) in cells underlying the macula. Over time, the abnormal accumulation of this substance can damage cells that are critical for clear central vision. As a result, people with this disorder often lose their central vision, and their eyesight may become blurry or distorted. Vitelliform macular dystrophy typically does not affect side (peripheral) vision or the ability to see at night.

Researchers have described two forms of vitelliform macular dystrophy with similar features. The early-onset form (known as Best disease) usually appears in childhood; the onset of symptoms and the severity of vision loss vary widely. It is associated with mutations in the VMD2/BEST1 gene. The adult-onset form (Adult vitelliform macular dystrophy) begins later, usually in mid-adulthood, and tends to cause vision loss that worsens slowly over time. It has been associated with mutations in the PRPH2 gene. The two forms of vitelliform macular dystrophy each have characteristic changes in the macula that can be detected during an eye examination.

Rod-Cone Dystrophy.

Rod-cone dystrophies are a family of progressive diseases in which rod dysfunction, which leads to night blindness and loss of peripheral visual field expanses, is either the prevailing problem or occurring at least as severely as cone dysfunction. A scallop-bordered lacunar atrophy may be seen in the midperiphery of the retina. The macula is only mildly involved by clinical examination although central retinal thinning is seen in all cases. Dyschromatopsia is mild early and usually becomes more severe. The visual fields are moderately to severely constricted although in younger individuals a typical ring scotoma is present. The peripheral retina contains 'white dots' and often resembles the retinal changes seen in retinitis punctate albescens. Retinitis pigmentosa is the main group of diseases included under this definition and, as a whole, is estimated to affect approximately one in every 3,500 people. Depending on the classification criteria used, about 60-80% of all retinitis pigmentosa patients have a clear-cut rod-cone dystrophy pattern of retinal disease and once other syndromic forms are taken into account, about 50-60% of all retinitis pigmentosas fall in the rod-cone dystrophy nonsyndromic category.

Leber's Congenital Amaurosis.

Leber's congenital amaurosis (LCA) is a severe dystrophy of the retina that typically becomes evident in the first year of life. Visual function is usually poor and often accompanied by nystagmus, sluggish or near-absent pupillary responses, photophobia, high hyperopia, and keratoconus. Visual acuity is rarely better than 20/400. A characteristic finding is Franceschetti's oculo-digital sign, comprising eye poking, pressing, and rubbing. The appearance of the fundus is extremely variable. While the retina may initially appear normal, a pigmentary retinopathy reminiscent of retinitis pigmentosa is frequently observed later in childhood. The electroretinogram (ERG) is characteristically "nondetectable" or severely subnormal. Mutations in 17 genes are known to cause LCA: GUCY2D (locus name: LCA1), RPE65 (LCA2), SPATA7 (LCA3), AIPL1 (LCA4), LCA5 (LCA5), RPGRIP1 (LCA6), CRX (LCA7), CRB1 (LCA5), NMNAT1 (LCA9), CEP290 (LCA10), IMPDH1 (LCA11), RD3 (LCA12), RDH12 (LCA13), LRAT (LCA14), TULP1 (LCA15), KCNJ13 (LCA16), and IQCB1. Together, mutations in these genes are estimated to account for over half of all LCA diagnoses. At least one other disease locus for LCA has been reported, but the gene is not known.

X-Linked Retinoschisis.

X-linked retinoschisis (XLRS) is characterized by symmetric bilateral macular involvement with onset in the first decade of life, in some cases as early as age three months. Fundus examination shows areas of schisis (splitting of the nerve fiber layer of the retina) in the macula, sometimes giving the impression of a spoke wheel pattern. Schisis of the peripheral retina, predominantly inferotemporally, occurs in approximately 50% of individuals. Affected males typically have vision of 20/60 to 20/120. Visual acuity often deteriorates during the first and second decades of life but then remains relatively stable until the fifth or sixth decade. The diagnosis of X-linked juvenile retinoschisis is based on fundus findings, results of electrophysiologic testing, and molecular genetic testing. RS1 is the only gene known to be associated with X-linked juvenile retinoschisis.

An individual affected by a cone cell disorder or at risk for developing a cone cell disorder can be readily identified using techniques to detect the symptoms of the disorder as known in the art, including, without limitation, fundus photography; Optical coherence tomography (OCT); adaptive optics (AO); electroretinography, e.g. ERG, color ERG (cERG); color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like; as will be known by the ordinarily skilled artisan. Additionally or alternatively, the individual affected by a cone cell disorder or at risk for developing a cone cell disorder can be readily identified using techniques to detect gene mutations that are associated with the cone cell disorder as known in the art, including, without limitation, PCR, DNA sequence analysis, restriction digestion, Southern blot hybridization, mass spectrometry, etc. In some embodiments, the method comprises the step of identifying the individual in need of a cone cell therapy. In such instances, any convenient method for determining if the individual has the symptom(s) of a cone cell disorder or is at risk for developing a cone cell disorder, for example by detecting the symptoms described herein or known in the art, by detecting a mutation in a gene as herein or as known in the art, etc. may be utilized to identify the individual in need of a cone cell therapy.

In practicing the subject methods, the subject composition is typically delivered to the retina of the subject in an amount that is effective to result in the expression of the transgene in the cone cells. In some embodiments, the method comprises the step of detecting the expression of the transgene in the cone cells.

There are a number of ways to detect the expression of a transgene, any of which may be used in the subject embodiments. For example, expression may be detected directly, i.e. by measuring the amount of gene product, for example, at the RNA level, e.g. by RT-PCR, Northern blot, RNAse protection; or at the protein level, e.g. by Western blot, ELISA, immunohistochemistry, and the like. As another example, expression may be detected indirectly, i.e. by detecting the impact of the gene product on the viability or function of the cone photoreceptor in the subject. For example, if the gene product encoded by the transgene improves the viability of the cone cell, the expression of the transgene may be detected by detecting an improvement in viability of the cone cell, e.g. by fundus photography, Optical coherence tomography (OCT), Adaptive Optics (AO), and the like. If the gene product encoded by the transgene alters the activity of the cone cell, the expression of the transgene may be detected by detecting a change in the activity of the cone cell, e.g. by electroretinogram (ERG) and color ERG (cERG); functional adaptive optics; color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like, as a way of detecting the presence of the delivered polynucleotide. In some instances, both an improvement in viability and a modification in cone cell function may be detected.

In some embodiments, the subject method results in a therapeutic benefit, e.g. preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy. For example, therapeutic efficacy in treating macular degeneration may be observed as a reduction in the rate of macular degeneration or a cessation of the progression of macular degeneration, effects which may be observed by, e.g., fundus photography, OCT, or AO, by comparing test results after administration of the subject composition to test results before administration of the subject composition. As another example, therapeutic efficacy in treating a progressive cone dysfunction may be observed as a reduction in the rate of progression of cone dysfunction, as a cessation in the progression of cone dysfunction, or as an improvement in cone function, effects which may be observed by, e.g., ERG and/or cERG; color vision tests; functional adaptive optics; and/or visual acuity tests, for example, by comparing test results after administration of the subject composition to test results before administration of the subject composition and detecting a change in cone viability and/or function. As a third example, therapeutic efficacy in treating a color vision deficiency may be observed as an alteration in the individual's perception of color, e.g. in the perception of red wavelengths, in the perception of green wavelengths, in the perception of blue wavelengths, effects which may be observed by, e.g., cERG and color vision tests, for example, by comparing test results after administration of the subject composition to test results before administration of the subject composition and detecting a change in cone viability and/or function.

Expression of a transgene delivered by the subject rAAV is expected to be robust. Accordingly, in some instances, the expression of the transgene, e.g. as detected by measuring levels of gene product, by measuring therapeutic efficacy, etc, may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g. as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In certain embodiments, the method comprises the step of detecting expression of the polynucleotide delivered by the subject rAAV in the cone cells, wherein expression is enhanced relative to expression from an AAV not comprising a 7-10 amino acid insert in the GH loop. i.e. a reference control, e.g. a parental rAAV into which the peptide has been inserted. Typically, expression will be enhanced 2-fold or more relative to the expression from a reference, e.g. a parental rAAV, for example 3-fold, 4-fold, or 5-fold or more, in some instances 10-fold, 20-fold or 50-fold or more, e.g. 100-fold, as evidenced by, e.g. earlier detection, higher levels of gene product, a stronger functional impact on the cells, etc.

Typically, an effective amount to achieve a change in will be about $1 \times 10^8$ vector genomes or more, in some cases $1 \times 10^9$, $1 \times 10^{10}$, $1 \times 10^{11}$, $1 \times 10^{12}$, or $1 \times 10^{13}$ vector genomes or more, in certain instances, $1 \times 10^{14}$ vector genomes or more, and usually no more than $1 \times 10^{15}$ vector genomes. In some cases, the amount of vector genomes that is delivered is at most about $1 \times 1015$ vector genomes, e.g. $1 \times 10^{14}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes, and typically no less than $1 \times 10^8$ vector genomes. In some cases, the amount of vector genomes that is delivered is $1 \times 10^{10}$ to $1 \times 10^{11}$ vector genomes. In some cases, the amount of vector genomes that is delivered is $1 \times 10^{10}$ to $3 \times 10^{12}$ vector genomes. In some cases, the amount of vector genomes that is delivered is $1 \times 10^9$ to $3 \times 10^{13}$ vector genomes. In some cases, the amount of vector genomes that is delivered is $1 \times 10^8$ to $3 \times 10^{14}$ vector genomes.

In some cases, the amount of pharmaceutical composition to be administered may be measured using multiplicity of infection (MOI). In some cases, MOI may refer to the ratio, or multiple of vector or viral genomes to the cells to which the nucleic may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI.

In some aspects, the amount of pharmaceutical composition comprises about $1 \times 10^8$ to about $1 \times 10^{15}$ particles of recombinant viruses, about $1 \times 10^9$ to about $1 \times 10^{14}$ particles of recombinant viruses, about $1 \times 10^{10}$ to about $1 \times 10^{13}$ particles of recombinant viruses, or about $1 \times 10^{11}$ to about $3 \times 10^{12}$ particles of recombinant viruses.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for subretinal (applied directly to where action is desired for mainly a local effect), intravitreal (applied to the vitreous for a pan-retinal effect), or parenteral (applied by systemic routes, e.g. intravenous, intramuscular, etc.) applications. Effective amounts of dose and/or dose regimen can readily be determined empirically from preclinical assays, from safety and escalation and dose range trials, individual clinician-patient relationships, as well as in vitro and in vivo assays such as those described herein and illustrated in the Experimental section, below.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

BACKGROUND

New therapies are needed for the treatment of many cone photoreceptor associated disorders, including macular dystrophies such as cone-rod dystrophy, cone dystrophy, Stargardt macular dystrophy, and achromatopsia; color vision disorders such as protan, deutan, and tritan defects; and vision disorders of the central macula such as age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis. As these vision disorders are associated with a loss of function and/or viability of the cone photoreceptors, it is hypothesized that these disorders may be treatable by delivering a therapeutic gene to cone photoreceptors to rescue cone viability and function.

Figure 6A:
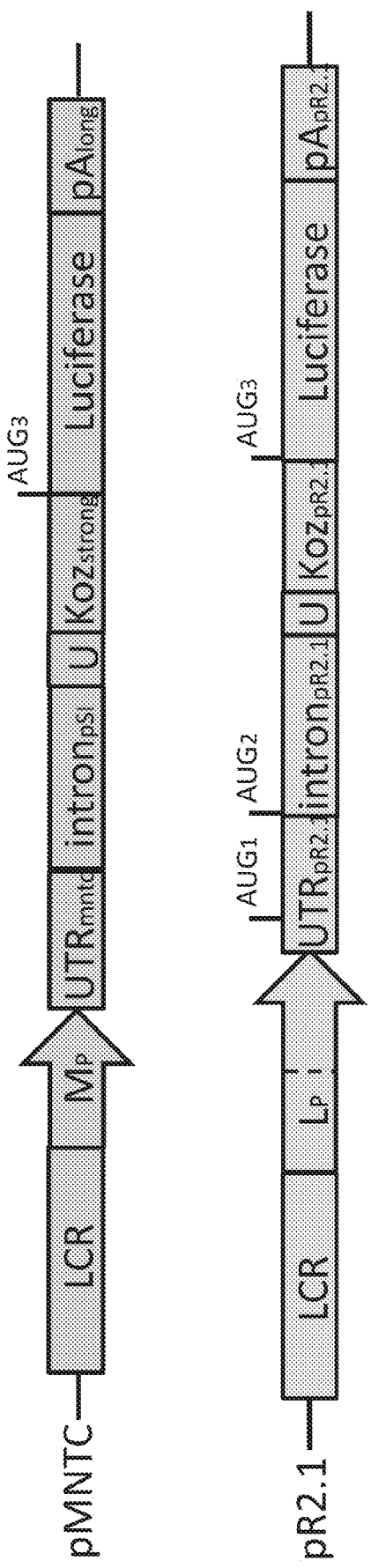
FIG. 6A-6D demonstrate the contribution of each of the optimized pMNTC elements to the more robust expression observed. (a) The pMNTC and pR2.1 expression cassettes. (b) The experimental expression cassettes, in which each element in pMNTC is replaced one-by-one by the corresponding element in pR2.1. (c,d) Expression of the luciferase transgene in the retinas of gerbils intravitreally injected with each of the test articles (n=6-8 eyes per construct) as detected (c) 4 weeks and (d) 8 weeks after injection by IVIS imaging. "7m8.CMV" served as the positive control.
Figure 6B:
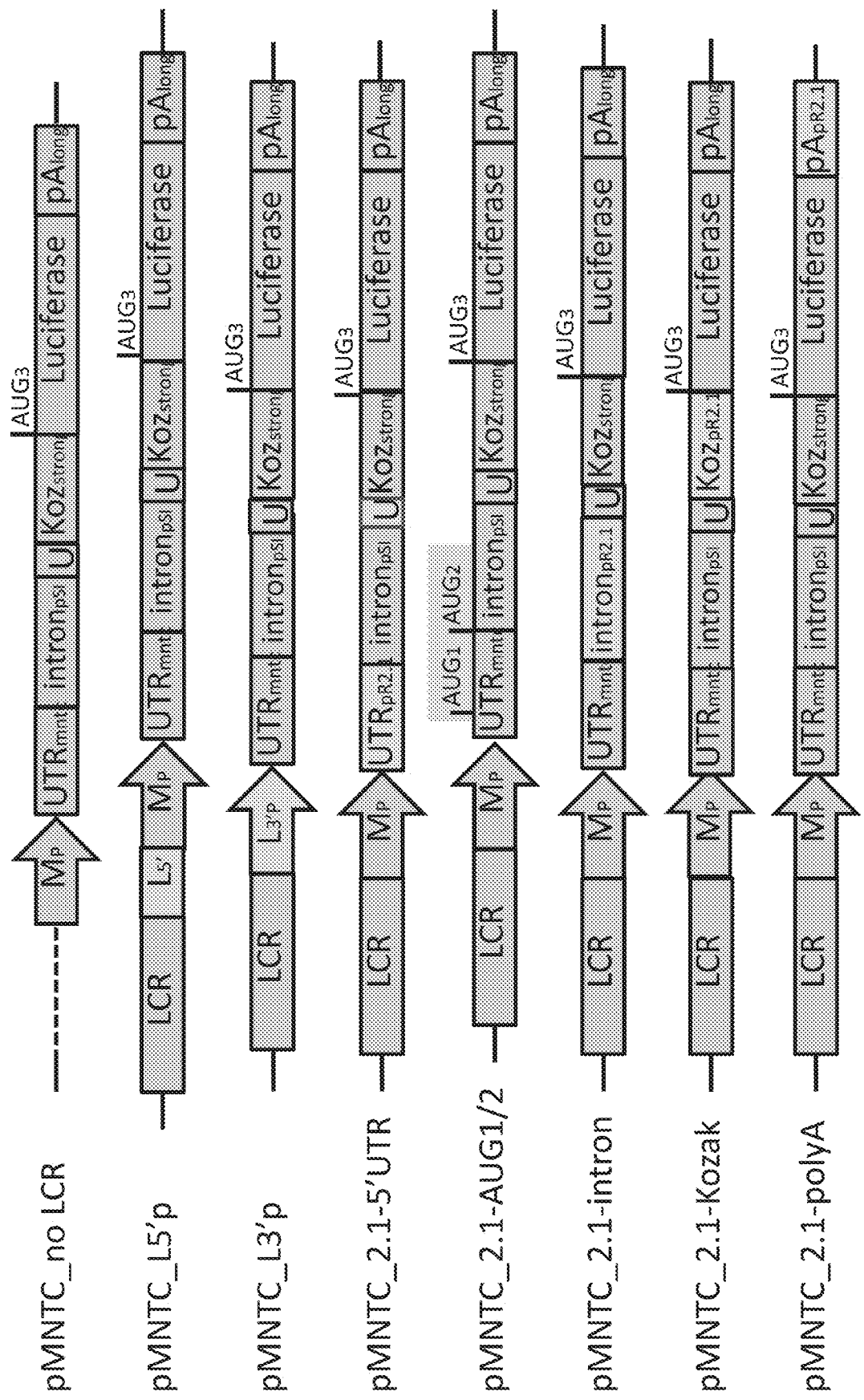
Figure 6C:
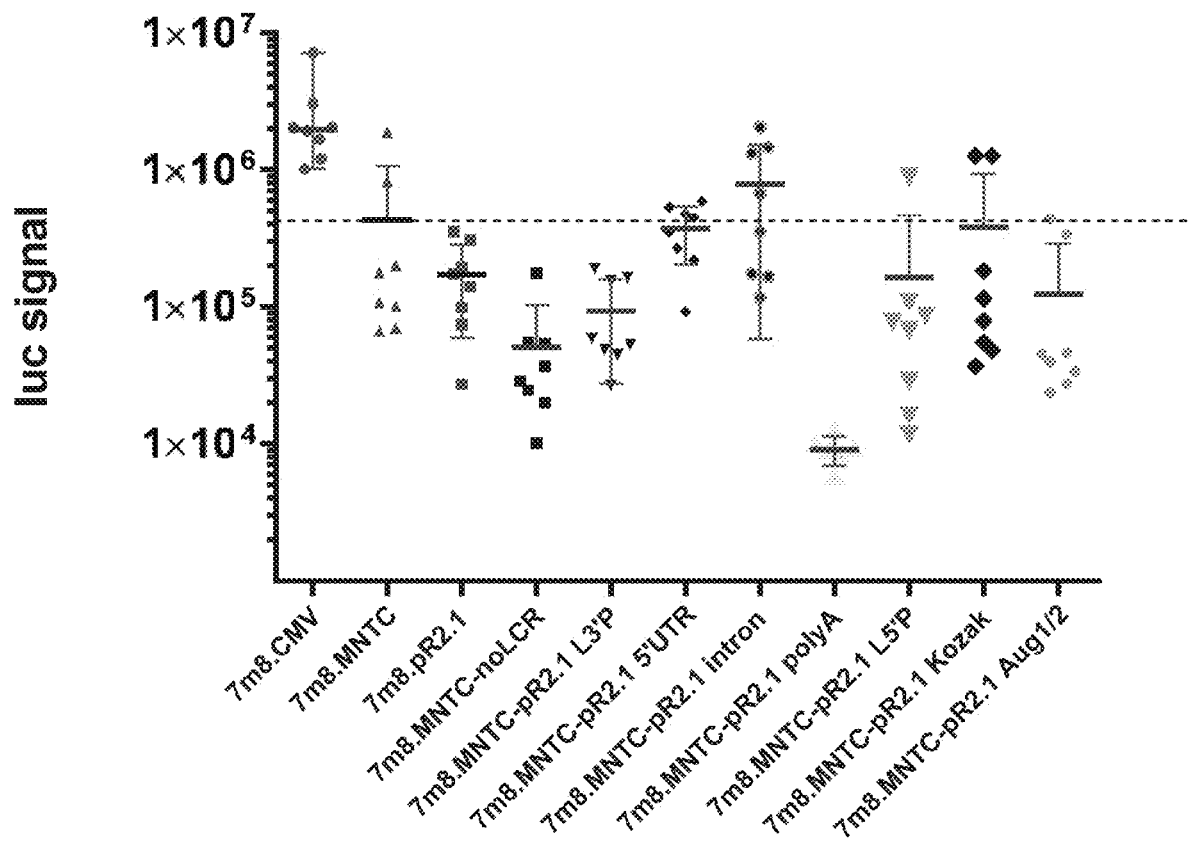
Figure 6D:
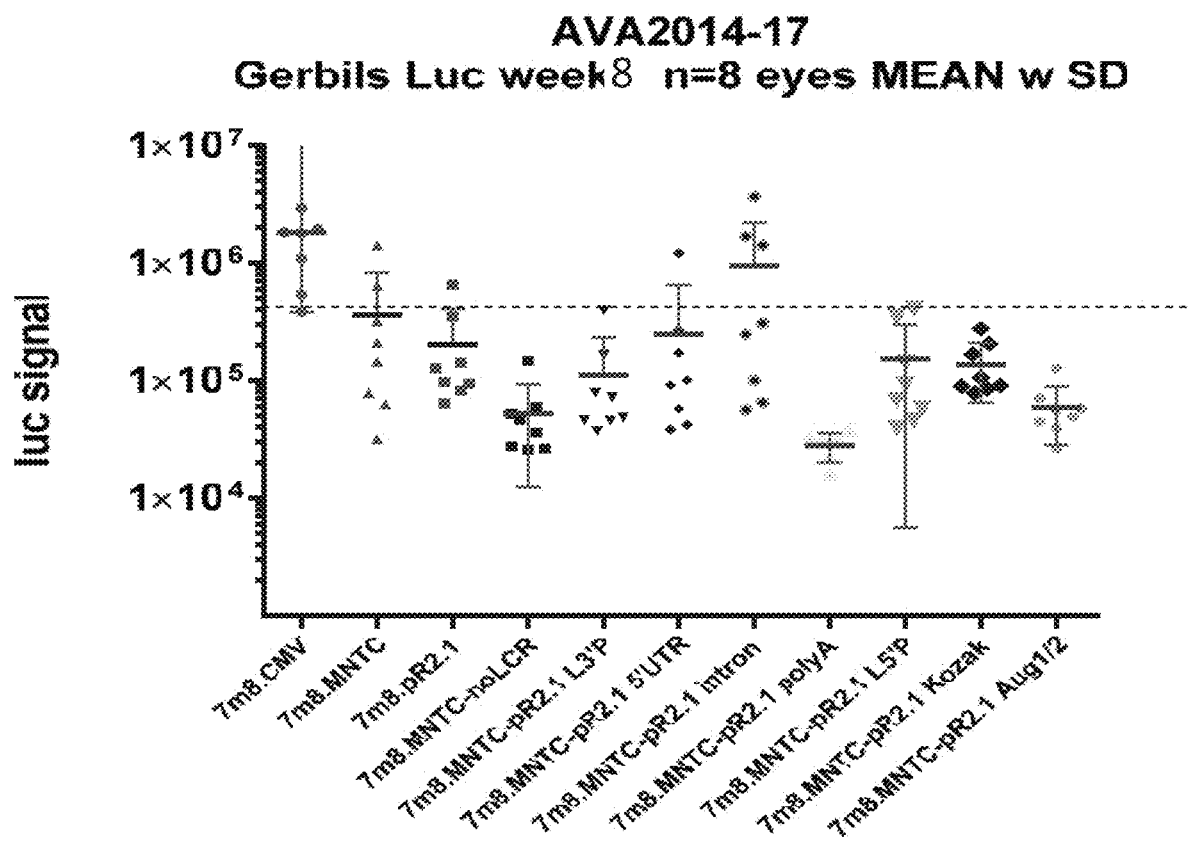

To that end, the polynucleotide cassette "pMNTC" was designed in which enhancer, promoter, 5'UTR, intron, Kozak, and polyadenylation sequences were designed for cone-specific expression (FIG. 6a). The cassette included an LCR enhancer sequence from the L- and M-opsin genomic locus and a truncated promoter sequence from the M-Opsin gene, comprising about 140 nucleotides upstream of the transcriptional start site. In addition, the cassette included a 5' untranslated region (5' UTR) based on the M-opsin 5'UTR but modified to have minimal secondary structure and to include additional sequence at its 3' end into which an intron was inserted. The intronic sequence used was a pSI chimeric intron having the 5'-donor site from the first intron of the human β-globin gene and the branch and 3'-acceptor site from the intron that lies between the leader and the body of an immunoglobulin gene heavy chain variable region (Bothwell, A. L. et al. (1981) Heavy chain variable region contribution to the NPb family of antibodies: Somatic mutation evident in a gamma 2a variable region. Cell 24, 625-37). The sequences of the donor and acceptor sites, along with the branchpoint site, were changed to match the consensus sequences for splicing (Senapathy, P., Shapiro, M. B. and Harris, N. L. (1990) Meth. Enzymol. 183, 252-78). Also included in the pMNTC polynucleotide cassette was a strong Kozak sequence and an SV40 polyadenylation sequence. The polynucleotide cassette "pM NTC" was designed in which enhancer, promoter, 5'UTR, intron, Kozak, and polyadenylation sequences were optimized for cone-specific expression. These included the inclusion of the LCR enhancer sequence from the L- and M-opsin genomic locus (SEQ ID NO:25); a truncated promoter sequence from the M-Opsin gene (SEQ ID NO:26); and the 5' untranslated region (5' UTR) of the M-Opsin gene that we modified to include additional sequence at its 3' end into which we inserted an intron (SEQ ID NO:28), since transfection studies have demonstrated that the presence of an intron flanking the cDNA to be transcribed may increase the level of gene expression (Gross, M. K., et al. (1987) Mol. Cell. Biol. 7, 4576-81; Buchman, A. R. and Berg, P. (1988) Mol. Cell. Biol. 8, 4395-405; Evans, M. J. and Scarpulla, R. C. (1989) Gene 84, 135-42; Huang, M. T. and Gorman, C. M. (1990) Nucl. Acids Res. 18, 937-47). The intronic sequence used in pMNTC (SEQ ID NO:29) is a chimeric intron having the 5'-donor site from the first intron of the human p-globin gene and the branch and 3'-acceptor site from the intron that lies between the leader and the body of an immunoglobulin gene heavy chain variable region (Bothwell, A. L. et al. (1981) Heavy chain variable region contribution to the NPb family of antibodies: Somatic mutation evident in a gamma 2a variable region. Cell 24, 625-37). The sequences of the donor and acceptor sites, along with the branchpoint site, were changed to match the consensus sequences for splicing (Senapathy, P., Shapiro, M. B. and Harris, N. L. (1990) Meth. Enzymol. 183, 252-78). Also included in the pMNTC polynucleotide cassette was a strong Kozak sequence (SEQ ID NO:30) and a polyadenylation sequence (SEQ ID NO:31).

Experiments were also performed to identify the best AAV with which to deliver transgenes to cone cells. Successful delivery of polynucleotides to cells of the retina for the purposes of gene therapy has been achieved using viral vectors such as AAV and lentivirus. However, these viruses must be injected subretinally to reach the cells of the non-human primate (NHP) retina, a procedure that carries with it the risk of retinal damage. A less disruptive approach is administration by intravitreal injection. However, efficient transduction of cone photoreceptors following intravitreal delivery of AAV or lentivirus has never been demonstrated: while reports exist of AAVs with the ability to transduce retinal cone cells with high efficiency (Merigan et al. IOVS 2008, 49 E-abstract 4514), later reports have questioned the efficacy of these vectors (Yin et al. IOVS 2011, 52(5):2775-2783).

Results

Directed evolution of AAV2 has led to the identification of the viral variant "7m8" that is able to transduce photoreceptors better than wild type AAV2 (Dalkara et al. Sci Transl Med 2013). However, the retina contains two types of photoreceptors—rods and cones—and no reports exist demonstrated whether AAV2-7m8 can transduce cone photoreceptors, per se, and more particularly, cone photoreceptors in the highly cone-enriched area of the fovea. To test this possibility, we delivered AAV2-7m8 carrying an expression cassette of the ubiquitous promoter CMV operably linked to GFP to the retina of African Green monkey by intravitreal injection. Intravitreally delivered AAV2-7m8.CMV.GFP appeared to transduce retinal cells in the fovea centralis (the 0.35 mm diameter rod-free region of retina at the center of the foveal pit) and parafovea (the lip of the depression) of primates more efficiently than intravitreally-delivered AAV2 or other AAV variants previously shown in the art to transduce retinal cells. Neither AAV2-7m8 nor the other AAVs tested tested appeared to be able to transduce the cones of the primate fovea, the 1.5 mm-diameter cone-enriched region of retina that surrounds the foveola and forms the slopes of the pit (FIG. 1).

Figure 2:
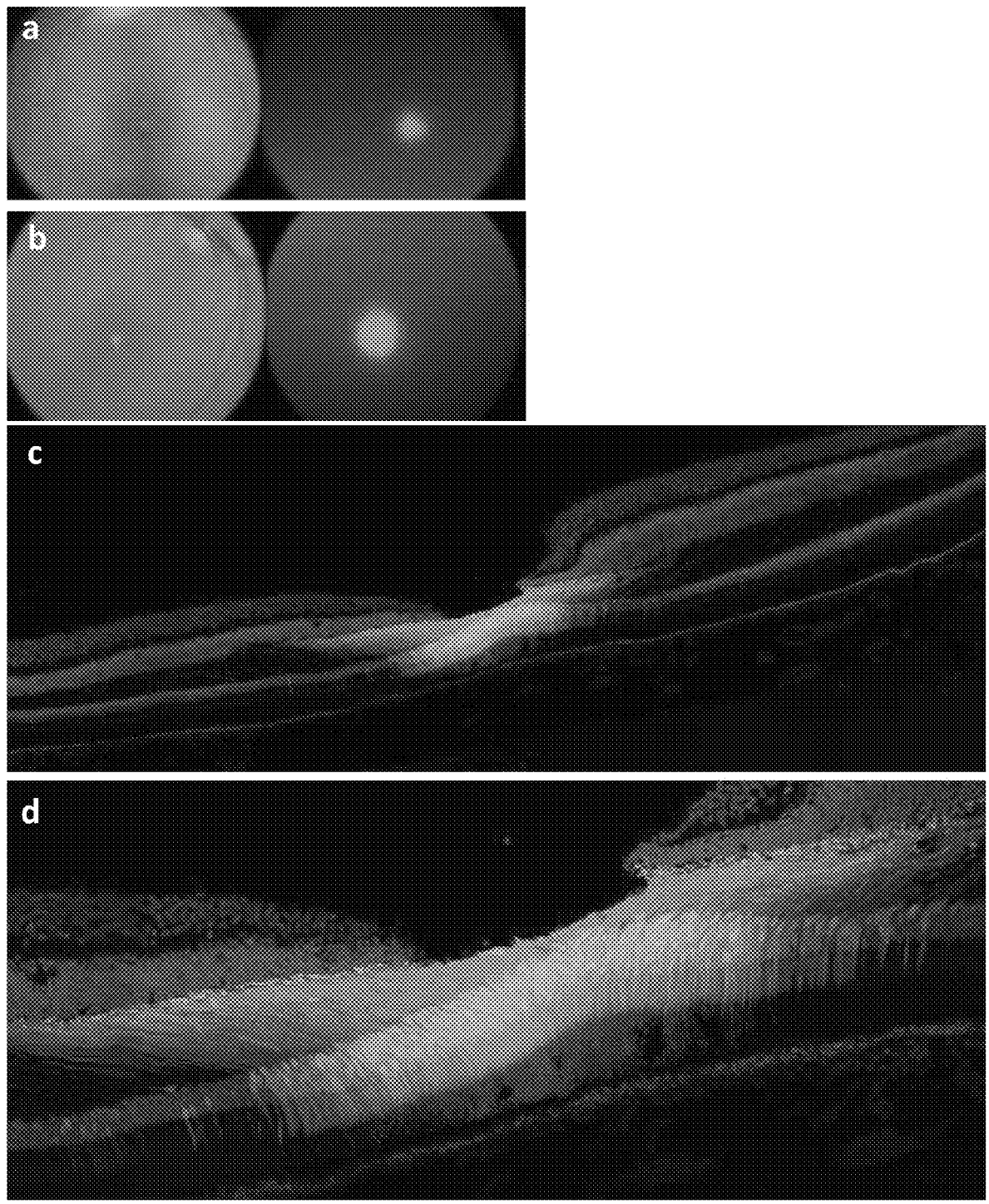
FIG. 2 illustrates how the robustly the AAV2-7m8 capsid transduces foveal cones of primates. (a-b) AAV2-7m8.MNTC.GFP was injected into the central vitreous of a baboon and expression was observed (a) 5 weeks and (b) 8 weeks later by fundus fluorescence. (c and d) Natural GFP fluorescence within a 15 micron section of the fovea at approximately 6 months after injection with AAV2-7m8.MNTC.GFP at low magnification (c) and high magnification (d).
Figure 4A:
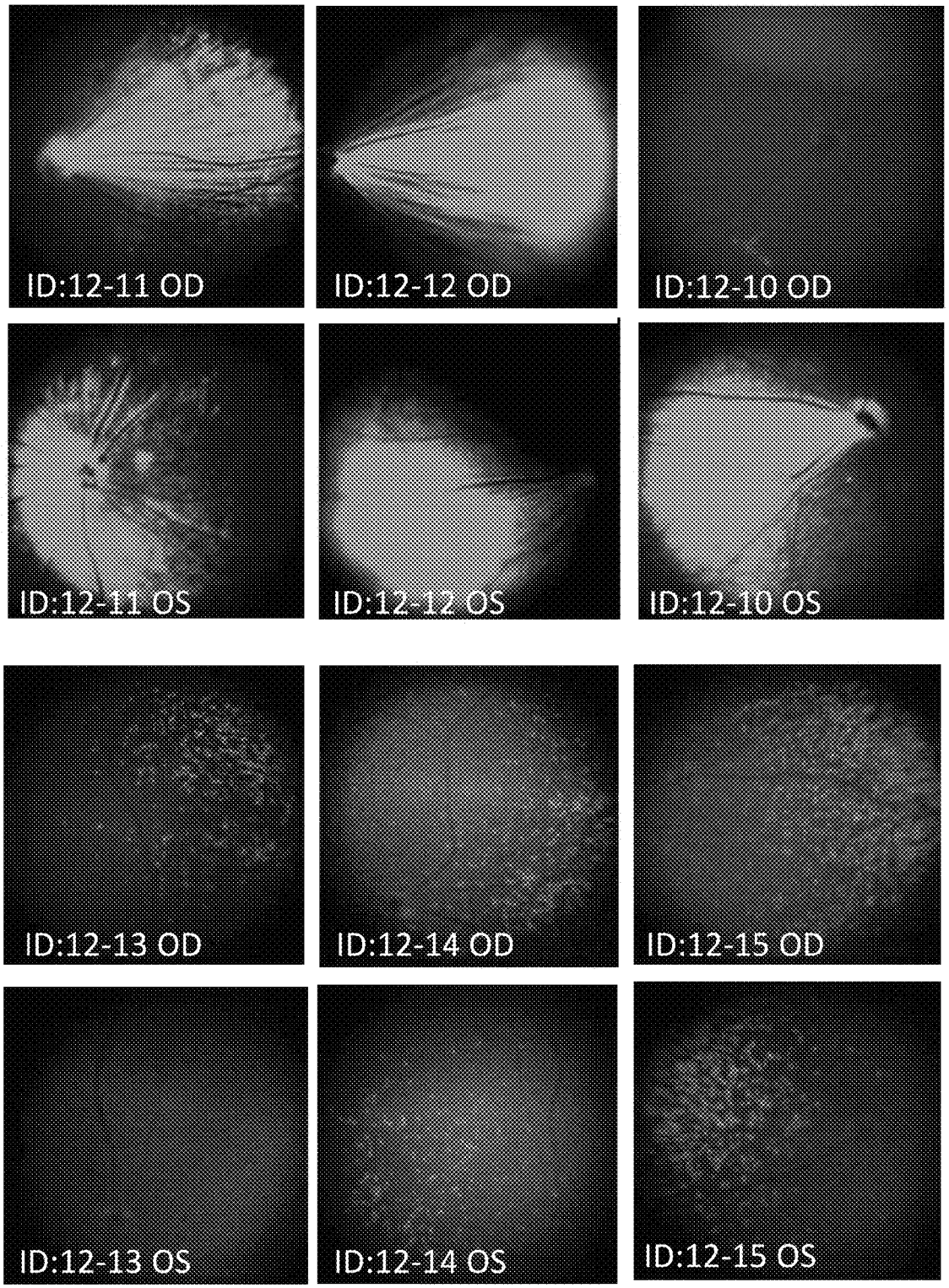
FIG. 4A-4B illustrates gene expression directed by the pMNTC regulatory cassette in the cones of the Mongolian gerbil retina. $1 \times 10^{10} - 2 \times 10^{10}$ vector genomes of virus carrying GFP under the control of the CMV, pR2.1, or MNTC promoter were injected in a volume of 5 uL into the vitreous of a Mongolian gerbil, and GFP expression visualized at the designated time points by fundus fluorescence imaging. (a) Expression of GFP directed by AAV2-7m8.CMV.GFP and AAV2-7m8.MNTC.GFP, visualized 4 weeks after intravitreal administration. Gerbils 12-10, 12-11, and 12-12 were injected with AAV2-7m8.CMV.GFP, while gerbils 12-13, 12-14, and 12-15 were injected with AAV2-7m8.MNTC.GFP. OD, oculus dexter (right eye). OS, oculus sinister (left eye). (b) Expression of GFP directed by AAV2-7m8.pR2.1.GFP and AAV2-7m8.MNTC.GFP, 4 and 8 weeks later as detected by fundus fluorescence imaging.

We next packaged a genome comprising pMNTC operably linked to GFP within the AAV2-7m8 capsid, and assessed the ability of this vector composition to express the GFP transgene in cone cells in vivo when injected intravitreally. Expression was evaluated in a number of species with varying numbers of retinal cones cells among total photoreceptors, including mouse (3% cones), rat (1% cones), gerbil (13% cones), and nonhuman primate (5% cones). Contrary to our results in FIG. 1, strong gene expression could be detected throughout the nonhuman primate fovea (FIG. 2). These data indicate that intravitreally delivered AAV2-7m8 can, in fact, transduce retinal cones, and that pMNTC acts as a robust expression cassette in cone cells. Robust reporter gene expression was also seen in the intravireally injected retina of the rat (data not shown) and gerbil (FIG. 4A), with expression levels and anatomic location correlating with cone abundance and location in all species.

Figure 3:
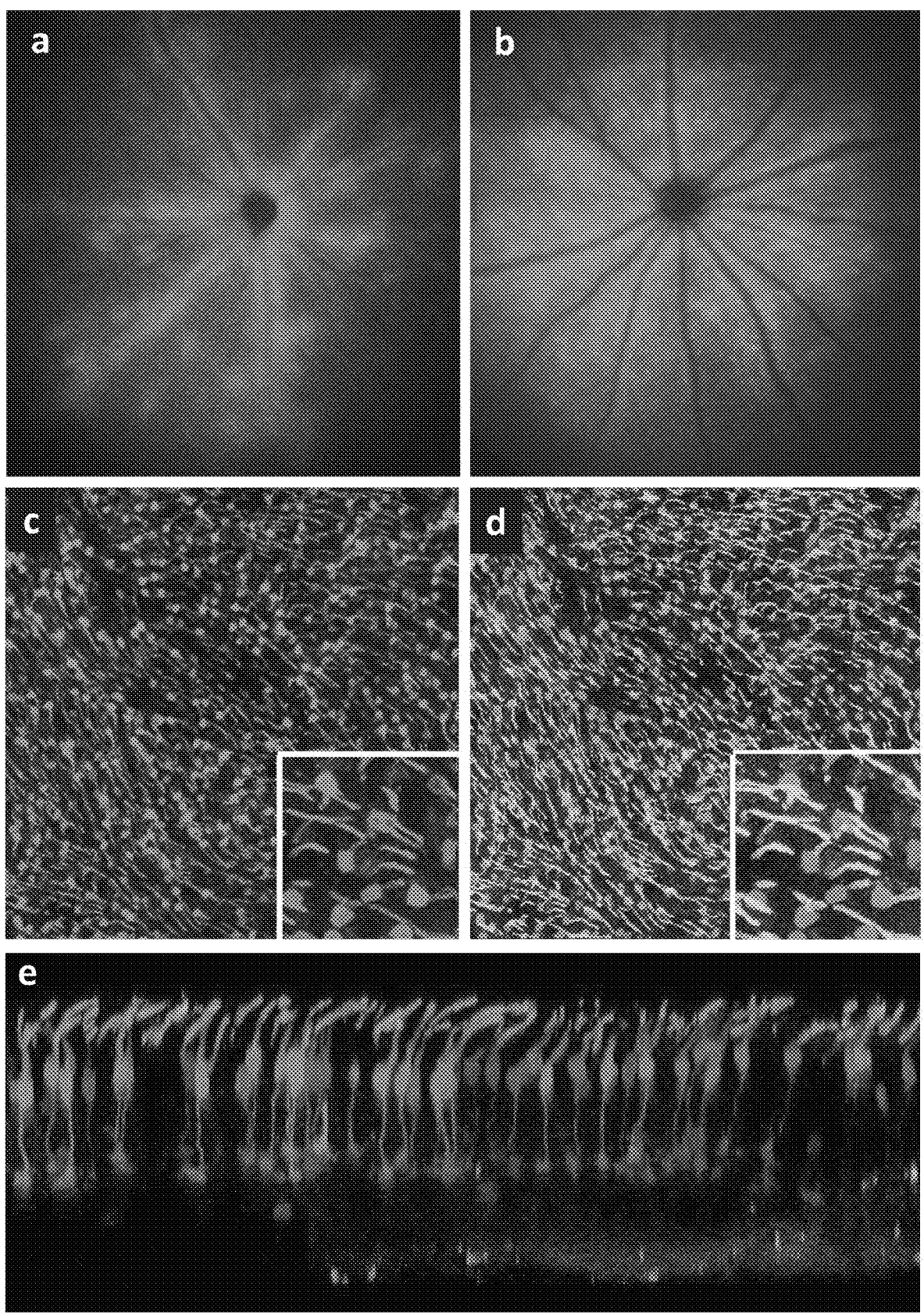
FIG. 3 illustrates robust and cone-specific gene expression in the cones of a mouse retina following intravitreal injection of AAV-7m8 delivered MNTC.GFP. (a-b) Examples of GFP fluorescence 11 weeks after mice received intravitreal injections of $5.04 \times 10^{10}$ vector genomes via intravitreal injection. (c-e) retinas were harvested for histology 14 weeks after injection and cone outer segments were labeled with an antibody to L/M opsin (red). In (c) the red channel is turned off so only the native GFP is visible, (d) is the same image with the red channel on to allow visualization of cone outer segments. Comparison of (c) and (d) shows that most if not all cones were transduced by the virus. (e) Image from the same retina as in c and d from different angle showing profiles of cone photoreceptors.

To determine the cell-specificity of pMNTC-directed expression, whole mounts of transduced mouse retina were analyzed by immunohistochemistry using an antibody that is specific for cone L and M opsins. The expression of L/M opsin, which labels the outer segments of cone photoreceptors only, was observed in virtually all of the cones of the mouse retina that expressed GFP from the AAV2-7m8.MNTC.GFP vector (FIG. 3), indicating that MNTC-directed expression of transgenes is highly cone-specific. Moreover 80% or more of the cone outer segments that were labelled by the L/M opsin-specific antibody also expressed the GFP transgene, indicating that AAV2-7m8 transduces cones highly efficiently (FIG. 3).

Figure 7:
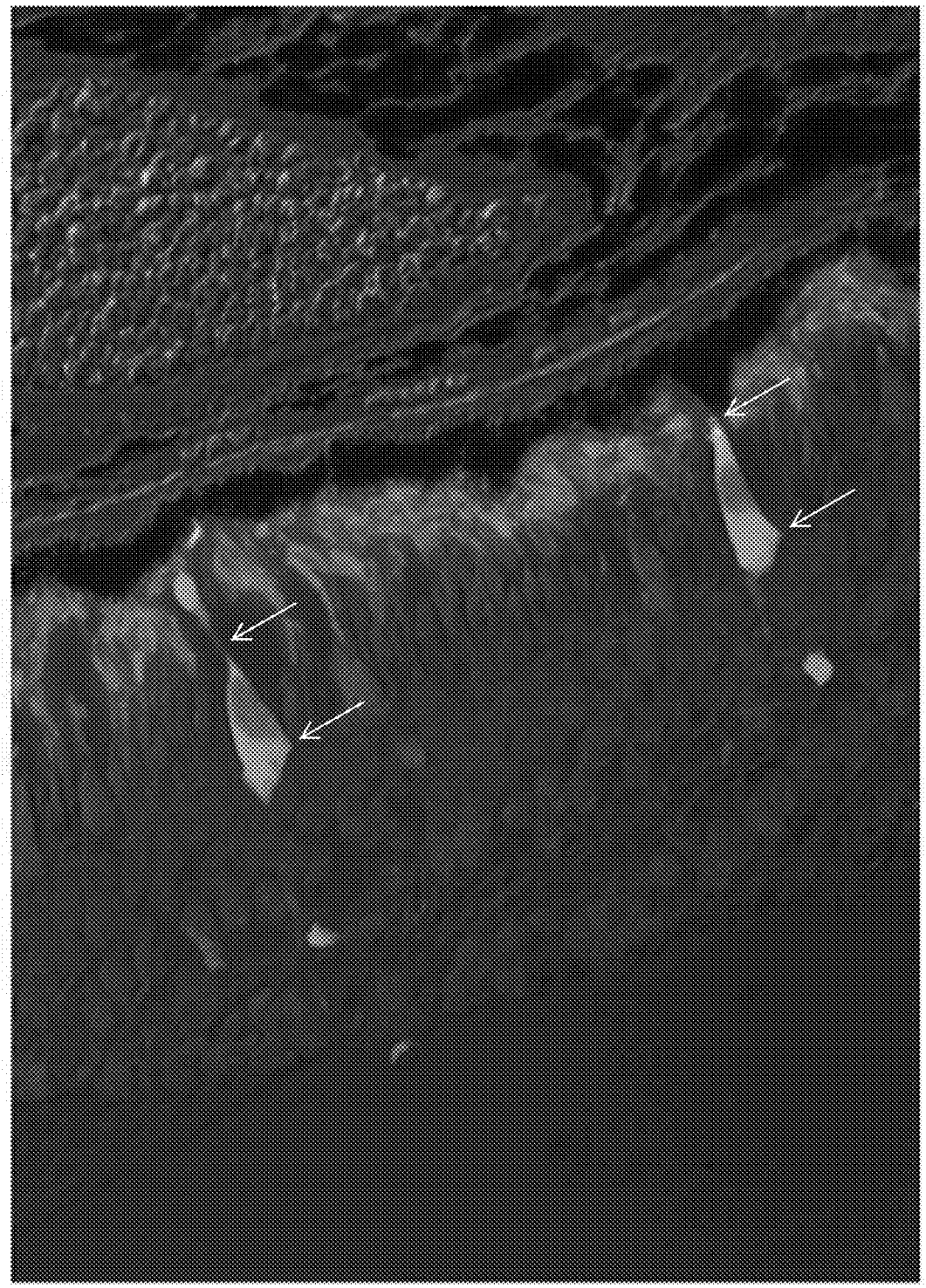
FIG. 7 illustrates cone-specific gene expression directed by the pR2.1 regulatory cassette in a non-human primate (NHP). $5 \times 10^{11}$ vector genomes of AAV2-7m8.pR2.1.GFP were injected in a volume of 50 uL into the vitreous of an African Green Monkey. GFP transgene expression was observed by stereo fluorescence microscopy of an 8 μm cross-section of the retina. GFP was stained with an anti-GFP antibody (green; chicken polyclonal; Abcam Cat #13970); opsin cone cells were stained with an anti-L/M Opsin antibody specific for opsin cones (red; rabbit polyclonal; Abcam Cat #5405); rod cells were stained with an anti-rhodopsin antibody (1D4 pink; mouse monoclonal; Abcam Cat #5417); and nuclei were stained with Dapi (blue/all nuclei; Invitrogen REF # D21490. GFP staining co-localized with L/M opsin staining but not rhodopsin staining. GFP transgene expression was present in L/M-opsin cones across the photoreceptor layer, but GFP transgene expression was not observed in rods. Arrows indicate illustrative cone cells double-stained for both GFP and opsin.

We also determined the cell-specificity of pR2.1-directed expression by packaging a genome comprising pR2.1 operably linked to GFP within the AAV2-7m8 capsid (AAV2-7m8pR2.1.GFP vector). pR2.1 comprises the human L/M opsin enhancer ("LCR") and the promoter region from the human L-Opsin gene. In addition, pR2.1 comprises the L-Opsin 5'UTR fused to additional 5'UTR sequence at its 3' end, into which modified SV40 late 16s intronic sequence has been inserted. This is followed by the L-Opsin Kozak sequence, which is then typically linked in-frame to a transgene. At the end of the cassette is an SV40 polyA tail. The ability of this vector composition to express the GFP transgene in cone cells in vivo was assessed 12 weeks after intravitreal injection in an African green monkey (non-human primate; NHP). Briefly, the NHP received bilateral intravitreal administrations of 50 uL of $1.0 \times 10^{13}$ vg/mL AAV2-7m8pR2.1.GFP to yield a final dose of $5 \times 10^{11}$ vg per eye. Retinal examination, including fundus color and fluorescence photography, was performed by using a Topcon TRC-50EX retinal camera with Canon 6D digital imaging hardware and a Spectralis OCT Plus at baseline and at weeks 4, 8, and 12 post-intravitreal vector injection. The animal was terminated at 12 weeks and eyes processed. A cross-section of a treated retina from the NHP was stained with a chicken polyclonal anti-GFP antibody (Abcam Cat #13970; Cambridge, UK); a rabbit polyclonal anti-L/M Opsin antibody specific for opsin cones (Abcam Cat #5405); a 1D4 mouse monoclonal anti-rhodopsin antibody (Abcam Cat #5417); and Dapi to stain all nuclei (Invitrogen Ref # D21490). GFP-tagged transgene containing cells were imaged by multispectral analysis along with the antibody probes and DIC (differential interference contract for topology). As flattened stacks of optical planes through the entire section. Cell analysis for transgene was optimized using morphology and colocalization with probes. GFP (transgene) staining co-localized with L/M opsin staining and not with rhodopsin staining, indicating that pR2.1 promotes expression in cone cells specifically (FIG. 7). GFP transgene signal was observed at fovea, mid and far periphery; GFP transgene signal colocalized with L/M-opsin, calbindin and PNA probe; clear exclusion of 1D4-containing cells in fovea was observed; and there was no GFP transgene positive cell association with rods or other probe-containing cells. (FIG. 7). In summary, cells double-stained for GFP (transgene expression) and L/M opsin were observed, but there was a lack of cells double-staining for both GFP and rhodopsin, indicating that the AAV2-7m8pR2.1.GFP vector specifically directed expression in cone cells and not rod cells.

Figure 4B:
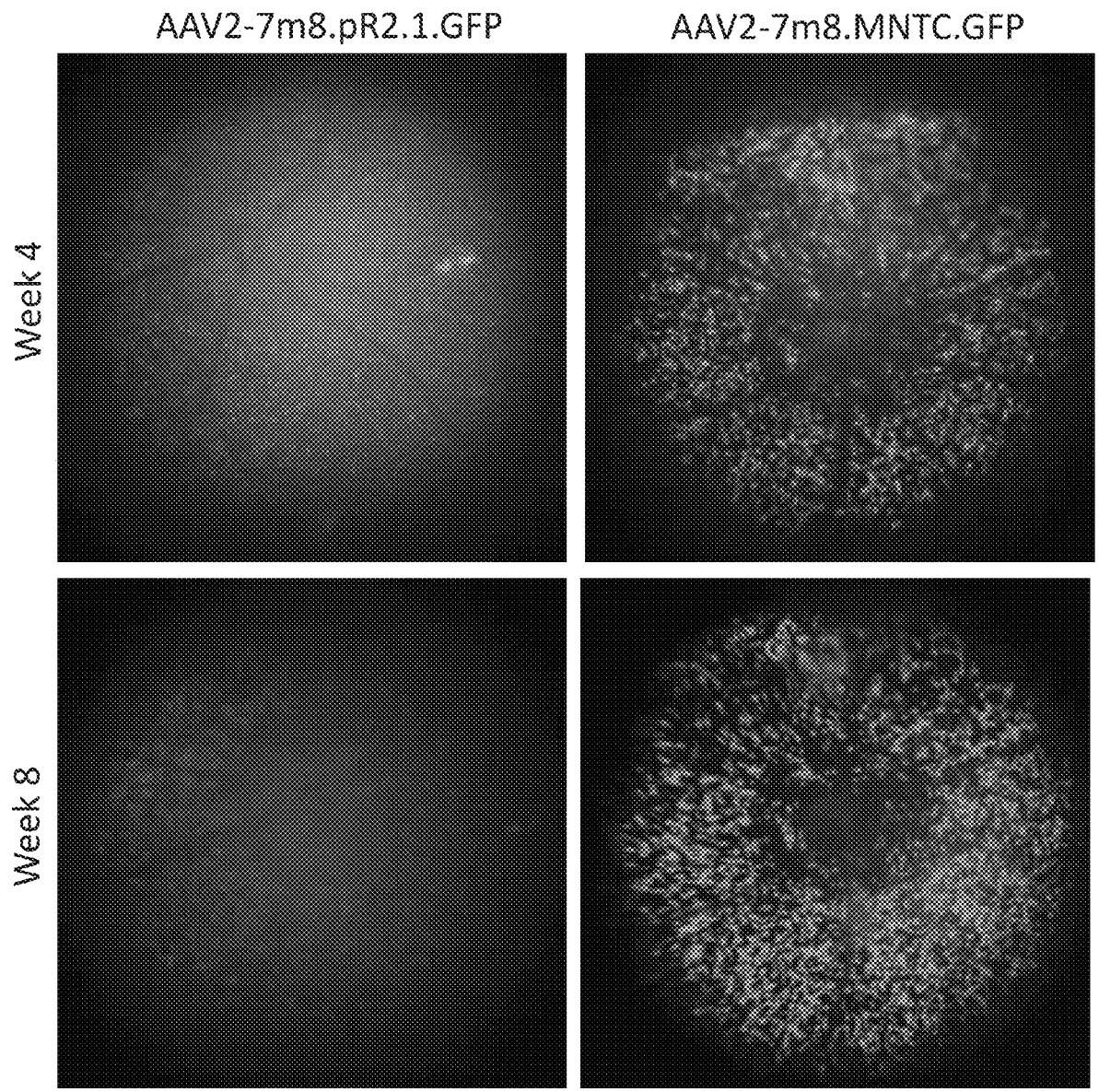
Figure 5A:
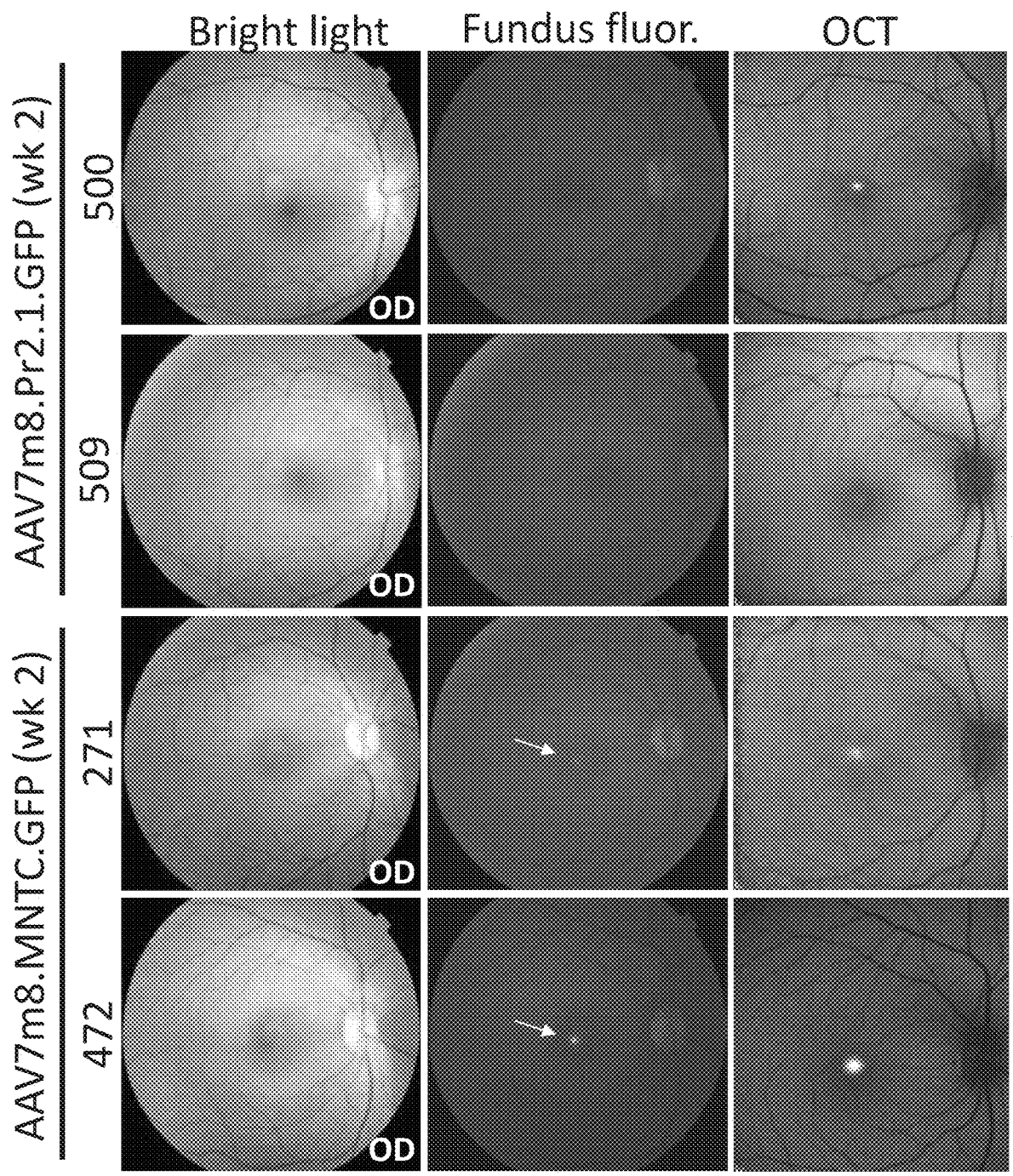
FIG. 5A-5D demonstrate that the pMNTC regulatory cassette provides for more robust gene expression in foveal cones of primates than the cone promoter pR2.1. $5 \times 10^{11}$ vector genomes of AAV2-7m8.MNTC.GFP or AAV2-7m8.pR2.1.GFP were injected in a volume of 50 uL into the vitreous of African Green Monkeys as indicated (AAV2-7m8.MNTC.GFP into animals 271 and 472; AAV2-7m8.pR2.1.GFP into animals 500 and 509). Retinas were visualized in vivo at (a) 2 weeks, (b) 4 weeks, (c) 8 weeks, and (d) 12 weeks for GFP using a fundus fluorescence camera (a, b, c, d) or autofluorescence on Heidelberg Spectralis OCT (a, b; data not shown for weeks 8 and 12). OD, oculus dexter (right eye). OS, oculus sinister (left eye).
Figure 5B:
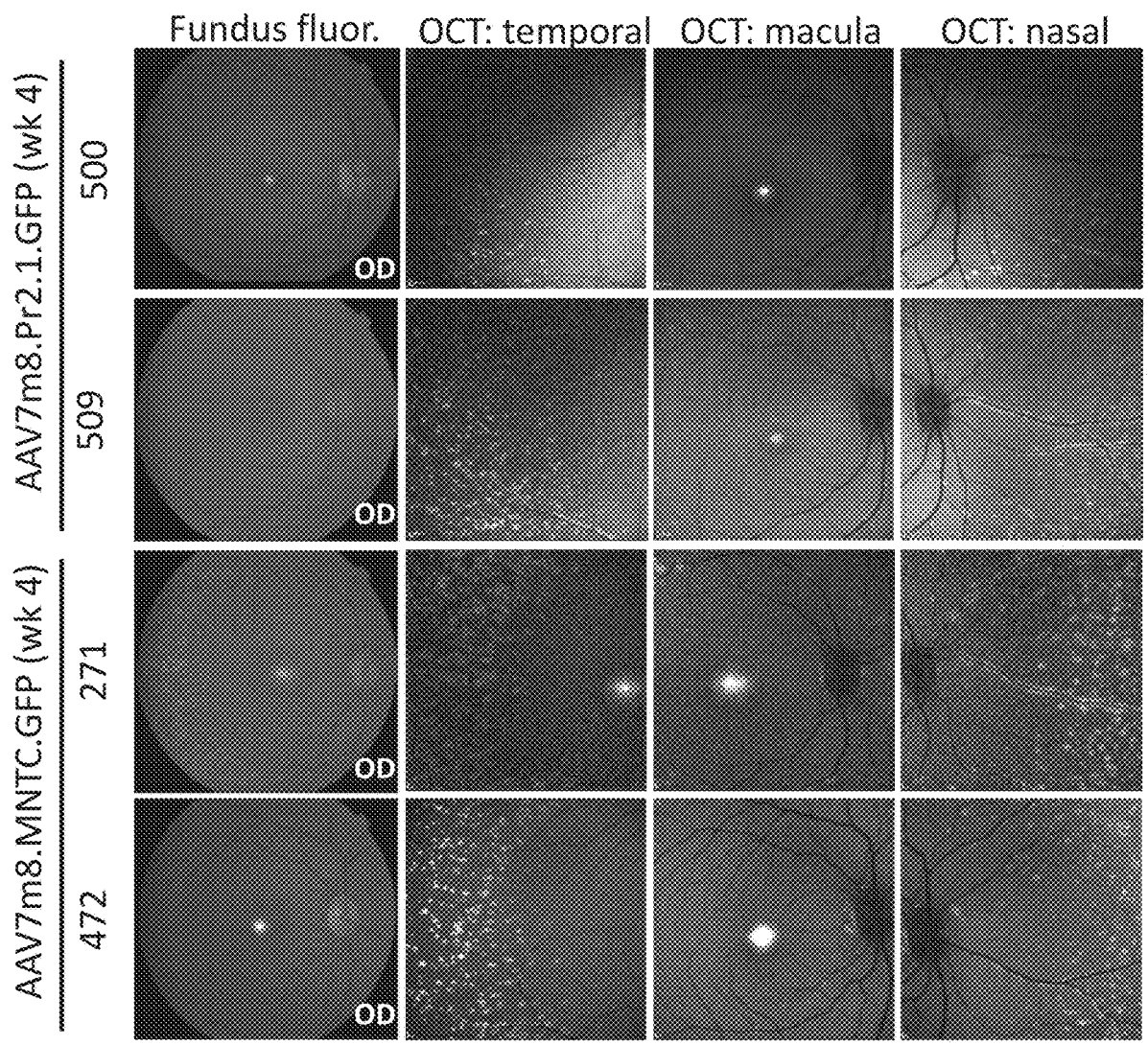
Figure 5C:
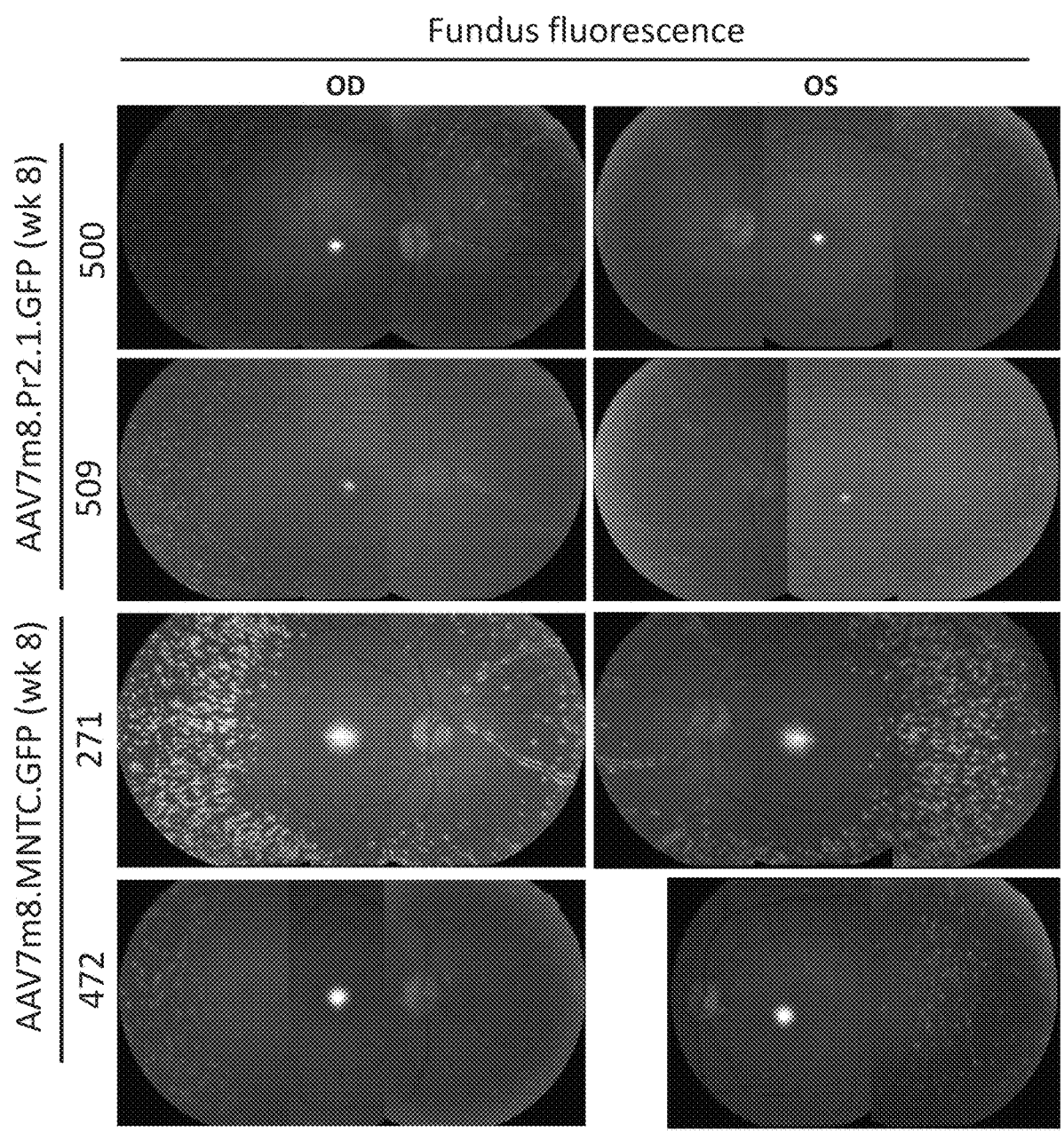
Figure 5D:
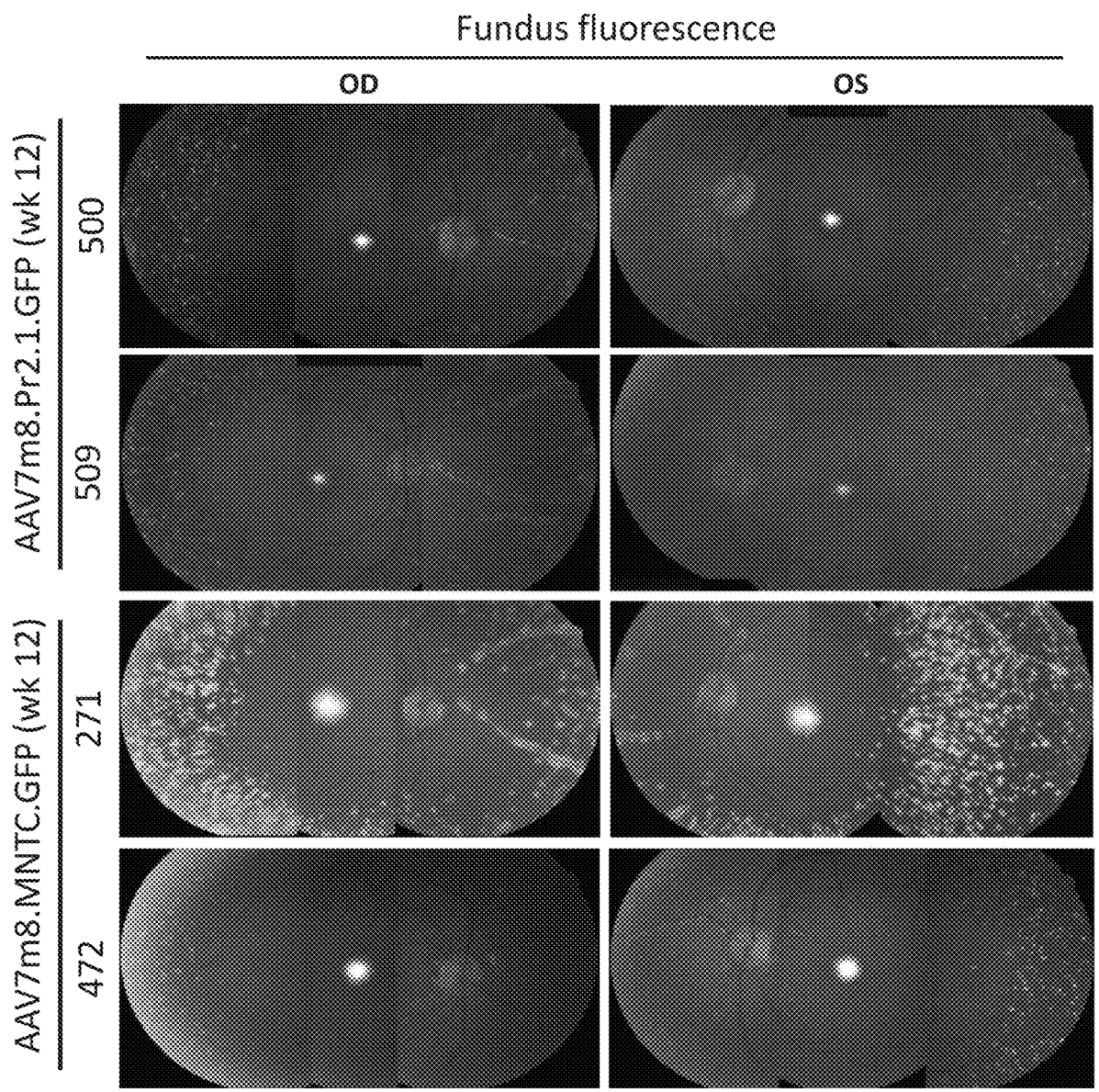

We next compared the ability of pMNTC to promote expression in cone cells to that of pR2.1. Viral preparations of AAV2-7m8.MNTC.GFP and AAV2-7m8.pR2.1.GFP were delivered intravitreally to the retinas of gerbils and nonhuman primates in vivo, and the retinas imaged in vivo 2 weeks, 4 weeks, 8 weeks, and 12 weeks later by fundus autofluorescence and OCT. GFP reporter expression was detected sooner, more strongly, and in more cones in gerbil retina transduced with rAAV carrying the pMNTC.GFP expression cassette than in gerbil retinas carrying the pR2.1.GFP expression cassette (FIG. 4B). Likewise, GFP reporter expression was detected sooner and in more cones in nonhuman primate retinas transduced with rAAV carrying the pMNTC.GFP expression cassette as compared to NHP retinas transduced with the pR2.1 expression cassette (FIG. 5, n=4 eyes). In both gerbils and NHP, GFP was consistently observed to be stronger from pMNTC than from pR2.1 throughout the duration of the study.

To determine the contribution of each of the elements in the pMNTC expression cassette to the overall improvement in expression, a series of expression constructs were cloned in which each of the elements in pMNTC was substituted one-by-one with the corresponding element from the pR2.1 expression cassette. These constructs were then packaged into AAV2-7m8 and delivered by intravitreal injection to the gerbil retina. Gerbil retinas were assessed 4 and 8 weeks later in vivo by in vivo bioluminescence (IVIS imaging system, PerkinElmer), which provides a quantitative readout of reporter expression across the entire eye.

As expected, expression of the luciferase reporter under the control of pMNTC was higher than expression of the luciferase reporter under the control of pR2.1 (FIG. 6). Replacement of the pMNTC promoter sequence with the pR2.1 promoter sequence having the most sequence homology to it reduced expression (construct pMNTC_pR2.1 L3'P), as did the inclusion of pR2.1 promoter sequence that lies more distal to the 5'UTR of pR2.1 (construct pMNTC_pR2.1-L5'P). Expression was also reduced by the introduction into the pMNTC 5'UTR of two false start sequences ("AUG1" and "AUG2") that were observed in the pR2.1 5'UTR (construct pMNTC_2.1-AUG1/2). Interestingly, expression was not reduced when the pMNTC 5'UTR was replaced with a modified pR2.1 5'UTR sequence in which these false starts had been removed (nucleotide 17 changed to C, nt 61 and 62 changed to CA) (pMNTC_pR2.1-5'UTR), suggesting that the pR2.1 5'UTR would promote strong expression in cone cells but for the false AUGs in the pR2.1 5'UTR element. Also interestingly, the pR2.1 intron appeared to provide more robust expression than the pSI chimeric intron of pMNTC, suggesting that inclusion of the pR2.1 intron in the polynucleotide cassettes of the present disclosure may be used to further improve expression in cone cells. Lastly, removal of the L/M enhancer (found in both pR2.1 and pMNTC) reduced expression as well. While the polyA tailed seemed at first to also have a significant impact on expression, re-sequencing of the pMNTC construct comprising this pR2.1 element revealed that the polyA tail was not operably linked to the transgene, thereby explaining why only background levels of expression were observed from this construct. Thus, the L/M opsin LCR, the inclusion of the M opsin core promoter rather than the L opsin promoter, and the exclusion of false starts in the 5'UTR all contribute to the enhancement in gene expression achieved using the pMNTC promoter.

In conclusion, we have identified an AAV variant, the AAV variant comprising a 7m8 peptide in the GH loop, which may be used for the intravitreal delivery of polynucleotides to retinal cones. Likewise, we have identified a number of polynucleotide cassette elements that may be used to promote strong expression in cone photoreceptors. Together, these discoveries represent improvements that may facilitate the development of therapeutic agents for cone-associated disorders.

Materials and Methods

Transgene expression in vitro in WERI-RB-1 cells. WERI-Rb-1 retinoblastoma cells expressing cone photoreceptor pigments cells are transfected with a polynucleotide cassette of the present disclosure according to the method described by Shaaban and Deeb, 1998; IOVS 39(6)885-896. The polynucleotide cassettes are transfected as plasmid DNA using well established techniques of molecular biology, such as cloning (Maniatis et al.) or via de novo DNA synthesis. All regulatory elements are placed in the cassette and used to drive the enhanced GFP protein. Plasmid DNA is then introduced into cells using established techniques for non-viral transfection, for example using a lipid-based transfection reagent (Altogen Biosystems, NV) or Lipofectamine LTX (Life Technologies). Cells are then cultured for 72 hours and eGFP expression is measured using flow cytometry and fluorescence microscopy. Transgene expression in cells transfected with the polynucleotide cassette of the present invention (i.e., constructs designed for cone photoreceptor expression) is compared to the un-optimized counterparts (i.e., those based on pR2.1) and is found to be stronger from cassettes carrying improved elements In vitro expression is also evaluated using other mammalian cell lines that express cone opsins, such as 661W cells (Tan et al., IOVS 2004; 45(3) 764-768).

Similarly, in vitro expression is evaluated using non-photoreceptor cell lines that have been engineered to express cone photoreceptor-specific proteins. Such a system has been described with HEK293 cells that have been genetically engineered to express CRX/Sp1 (Khani et al., IOVS 2007; 48: 3954). Marker genes are also used (eGFP, dsRed, mCherry, luciferase) as well as physiologic genes (opsin, ACHR genes). Physiologic genes are tested by examining mRNA levels (e.g., by RT-PCR) or protein levels (e.g., by ELISA or Western blot).

Animal Care.

All experiments conformed to the principles regarding the care and use of animals adopted by the American Physiological Society and the Society for Neuroscience, and were approved by the Institutional Animal Care and Use Committee (IACUC).

Small Animal Studies.

The expression of the gene products encoded by the coding sequence of the expression cassettes was evaluated in vivo in mice, rats, and gerbils. This was accomplished by intravitreal injection in vivo of an rAAV preparation comprising the expression cassette (Li et al., 2008; Mol Vis 48: 332-338). Note that electroporation of plasmid DNA may be performed instead (Matsuda/Cepko).

Mouse studies. Mice used in this study were C57BL/6. Animals were anesthetized with ketamine/xylazine (110 mg/kg intraperitoneal). A beveled 34 gauge disposable needle loaded with test article was inserted into the vitreous of the eye, and 5.04×1010 vector genomes of rAAV in a volume of 1.5 µl was injected into the vitreous.

Gerbil and rat studies. Mongolian gerbils (Meriones unguiculatus) and brown Norway rats were used in this study. Pupils were dilated with 10% phenylephrine and 0.5% tropicamide. Animals were anesthetized with an intraperitoneal or intramuscular injection of 0.1-0.2 mL of a ketamine/xylazine solution (70 mg/mL ketamine and 10 mg/mL xylazine for rats; 25 mg/mL ketamine and 0.3 mg/mL xylazine for gerbils). A beveled 34 gauge disposable needle loaded with test article in a 100 µL Hamilton syringe was inserted into the vitreous of the eye through the sclera at an optimized superior-temporal point about 1 mm from Limbus. 1×1010-2×1010 vector genomes of test article (2×1010 vg of rAAV.GFP, or 1.15×1010 vg of rAAV.luciferase) in a 5 uL volume was injected slowly with a microinjection pump into the vitreous, after which the needle tip was held in the injected eye at the injected position for 10 seconds so as to ensure adequate test article dispensing. The needle was then withdrawn.

Non-Human Primate (NHP) Studies.

The polynucleotide cassettes and expression vectors were also tested in large animals. This was done by using AAV, for example using the techniques of Mancuso et al. Briefly, an AAV cassette was made, the AAV encapsidating the expression cassette was manufactured, and the viral prep was injected intravitreally (up to 170 uL in the vitreous) or subretinally (up to 3, 100 uL injections at different locations; vitrectomy may be performed prior to injection) in nonhuman primates. Expression was evaluated by reporter (GFP), color ERG, and/or behavioral testing using the Cambridge Color Test or on animals trained to make a saccade (eye movement) when a target enters the field of view. The saccades are monitored using an eye tracker. Prior to treatment animals are trained to perform a color vision test or to make a saccade when it sees a colored target. An ERG is performed to estimate the spectral sensitivity of the cones present. Data from the color vision test performance and the ERG provide evidence that the animal is dichromatic (colorblind). For animals that receive a vector carrying the GFP gene, expression is monitored using fundus imaging with RetCam II or similar device under light that produces excitation of the GFP. For animals receiving a photopigment gene that differs in spectral sensitivity compared to the animal's endogenous pigments, expression is monitored using the multifocal color ERG to measure spectral sensitivity at up to 106 different retinal locations, and by behavioral testing.

Baboons were sedated with 10-15 mg/kg ketamine following by sevofluorane. African Green monkeys were sedated with an intramuscular injection of 5:1 ketamine: xylazine mix (0.2 ml/kg of 100 mg/ml ketamine and 20 mg/ml xylazine). Mydriasis was achieved with topical 10% phenylephrine. An eye speculum was placed in the eye to facilitate injections. A drop of proparacaine hydrochloride 0.5% and then 5% betadine solution was applied, followed by a rinse with sterile saline. Baboons (FIG. 2) received 60 µl of a $3.4 \times 10^{13}$ vg preparation of rAAV by intravitreal (ITV) injection to yield a final dose of $2.02 \times 10^{12}$ vg per eye. African Green monkeys received 50 uL of a $1 \times 10^{13}$ preparation of rAAV vector by ITV injection to yield a final dose of $5 \times 10^{11}$ vg per eye. ITV injections to the central vitreous were administered using a 31-gauge 0.375 inch needle (Terumo) inserted inferotemporally at the level of the ora serrata ~2.5 mm poster to the limbus under a surgical magnification to allow full visualization of extraocular and intraocular needle placement. Central vitreous placement was confirmed by direct observation of the needle tip at the time of the injection. Following ITV injections a topical triple antibiotic ointment was administered.

Slit-Lamp Biomicroscopy.

The anterior segment of each monkey eye was examined by slit-lamp biomicroscopy during baseline screening and at week 4 (day 28), week 8 (day 56) and week 12 (day 84) post-injection to monitor inflammation. No abnormalities were observed.

NHP Necropsy and Eye Processing.

Animals were euthanized with pentobarbital 12 weeks post intravitreal injection. Eyes were tagged with a suture at the 12 o'clock position before enucleating and trimming of extraocular tissues. Posterior cups were isolated by removing tissues anterior to the limbus and fixed by immersion in 4% paraformaldehyde and stored in 70% ethanol.

Immunolabeling.

Eyes were rehydrated into water then PBS buffer before flattening and delaminating retina as whole mounts. Preparations were imaged by stereo fluorescence microscopy (Discovery Fl V20, Carl Zeiss Microscopy, LLC, Thornwood, N.Y.) for GFP. Quadrant with fovea was detached from flat-mount, mounted under coverslip and imaged as full montage (5× tiling and stitching, Axio Observer Z1, Zeiss). Strip of retina was isolated central at fovea out to periphery, cryoprotected in sucrose and frozen in OCT. 8 µm sections were immunostained with antibodies to proteins enriched in specific retinal cell populations, including, L/M- and S-opsins, glutamine synthetase (GS), calbindin, rhodopsin (1D4), β-III Tubulin, Laminin, peanut agglutinin (PNA) and/or others. GFP-tagged transgene containing cells were imaged by multispectral analysis along with antibody probes and DIC (differential interference contract for topology) as flattened stacks of optical plains through entire section (Axio Observer Z1, with Apotome, Zeiss). Cell analysis for transgene was optimized using morphology and colocalization with probes.

Fundus Examination and Photography.

Eye examination and fundus photography of rat and gerbil retinas was performed using a Phoenix Micron IV fundus microscope. All animals received a baseline screening/photographing to confirm ocular health, and then photographed at the designated timepoints to monitor the expression of the GFP transgene. Any change to the optic nerves and retina or appearance of gross lesions were recorded by a color fundus photography and expression of GFP was visualized using fluorescence fundus imaging with a fluorescein filter.

Retinal examination, fundus color and fluorescence photography, and autofluorescence OCT of NHP were performed by using a Topcon TRC-50EX retinal camera with Canon 6D digital imaging hardware and New Vision Fundus Image Analysis System software and Spectralis OCT Plus. All animals received a baseline imaging. GFP expression was also documented at week 2, 4, 8, and 12 post-intravitreal vector injection.

IVIS Imaging System.

Expression of luciferase in the retina following delivery of rAAV.luciferase was quantified in vivo 2, 4 and 8 weeks post-intravitreal injection using an IVIS Imaging System. Gerbils were injected subcutaneously with 150 mg/kg luciferin (PerkinElmer) (15 mg/ml luciferin at a dose of 15 ml/kg). Approximately 22 minutes later, animals were sedated by inhalation of 4% isoflurane for 3-5 minutes. Immediately thereafter, animals were placed on the imaging platform in pairs, and the luminescence of the one eye of each animal quantified followed immediately by imaging of the contralateral eye. A naïve gerbil was used as a negative standard, with background levels of luminescence typically registering a luminescence of $1 \times 10^4$ photons/second. Bioluminescence verification using a phantom mouse (XPM-2 Perkin Elmer phantom mouse for bioluminescence imaging) was performed prior to imaging to ensure calibration of the imaging system.

Immunohistochemistry.

Mice were euthanized with a lethal dose of sodium pentobarbital and tissues fixed via cardiac perfusion first with 0.13M phosphate buffered saline (PBS) pH 7.2-7.4 containing 2 units of heparin per mL, followed by 4% paraformaldehyde (PFA) in PBS, followed by 4% paraformaldehyde plus 1% glutaraldehyde in PBS. Glutaraldehyde served to keep the neural retina attached to the RPE so that the cone outer segments would remain intact. Each solution was warmed to ~37° C. just prior to administration and ~35-40 mL of perfusate was delivered at each stage. Once the perfusion was stopped, the mouse was wrapped in a moist paper towel and left to further fix for 2-3 hours before enucleation and dissection.

Permanent ink was used to mark the orientation of the eye, the anterior segment was removed, and the eye-cup was fixed in 4% PFA overnight at 4° C. and then stored in PBS at 4° C. Retinal whole-mounts were made by flattening the dissected retina between tissues soaked in 4% PFA for two hours and then transferring them to a culture plate for 6 more hours of fixation. Afterward, the PFA was replaced with PBS containing 0.03% sodium azide (Sigma).

Antibody labeling was carried out on a rotating table shaker. To block non-specific labeling, whole mounts were incubated overnight at 4° C. with a solution containing 5% donkey serum (Jackson ImmunoResearch, Cat #004-000-120), 1 mg/ml BSA (Jackson ImmunoResearch, Cat #001-000-161), and 0.03% Triton X-100 in PBS (pH 7.4). The primary antibody used in this study was rabbit anti red-green (L/M) opsin diluted 1:200 (Millipore, Cat # AB5405. Specimens were washed in PBS 3 times for 30 minutes each, then incubated at 4° C. overnight with DAPI (4',6-diamidino-2-phenylindole, dihydrochloride 1:10,000; Invitrogen, Cat # D-21490) plus secondary antibodies. The secondary antibody for the L/M-opsin antibody was Alexa Fluor 488 labeled donkey anti-rabbit IgG(H+L) diluted 1:200 in antibody dilution buffer (Invitrogen, Cat # A21206). The incubation with secondary antibody was followed by three 30 minute PBS washes, 30 minutes of post-fixation with 4% paraformaldehyde, and three more 30 minute PBS washes. Finally, the retinal slices were placed on slides with 2% DABCO in glycerol and covered with cover slips.

Microscopy.

Wdefield images of mouse retina whole mounts were acquired using a Nikon Eclipse E1000 with a 20× (open-air) objective and camera set with a 1.5× optical zoom. For each specimen, 50 optical sections were taken 0.5 μm apart and the M-opsin Z-stack was reconstructed in ImageJ. The Z-stack was oriented so that the lengths of the outer segments were in plane, and the distance between where antibody staining began and ended was measured as an estimate of the length of the outer segments. Further, a 3D projection of the Z-stack was generated and the number of cones with visible M-opsin in the outer segment could be quantified.

Confocal image slices were acquired using an Olympus FluoView™ FV1000. Sections were imaged using a 20× oil immersion lens (40 images taken 0.5 μm apart) and the Z-stacks were reconstructed in ImageJ. Channel exposure levels were balanced within and across images using Adobe Photoshop. For the retinal whole mounts, images were taken using a 10× open-air lens and mosaics were constructed with Adobe Photoshop's native mosaic construction software.

Experiments testing the tissue specificity of the polynucleotide cassettes. In this instance, a construct encoding GFP is injected via one or more routes of administration, such as intravitreal, subretinal, or intravenously. The animal is then sacrificed and tissues are analyzed by qPCR—to detect DNA sequences indicating presence of the construct—and GFP expression—to detect areas where the construct is actively expressed. Whereas absence of DNA sequence indicates lack of biodistribution to a given tissue, the presence of DNA sequence together with the lack of transgene expression (mRNA or protein level) indicates presence of vector but lack of expression in that tissue. In this way, the level of specificity for cone photoreceptors can be established, and used to determine the utility of this invention in terms of restricting expression to target cone photoreceptor cells without expression in non-targeted tissues such as optic nerve, liver, spleen, or brain tissue. Intravitreal AAV is known to biodistribute to the brain (Provost et al) so highly expressed, improved constructs for targeting cone photoreceptors would be useful to limit expression to target cells of the retina and limit potential adverse events associated with off-target transgene expression.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

All publications and patent applications described herein are hereby incorporated by reference in their entireties.

SEQUENCE LISTING

```
<160> NUMBER OF SEQ ID NOS: 31

<210> SEQ ID NO 1
<211> LENGTH: 736
<212> TYPE: PRT
<213> ORGANISM: Adeno-associated virus - 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
```

```
            305                 310                 315                 320
        Val Lys Glu Val Thr Thr Asn Asp Gly Val Thr Thr Ile Ala Asn Asn
                        325                 330                 335

Leu Thr Ser Thr Val Gln Val Phe Ser Asp Ser Glu Tyr Gln Leu Pro
                        340                 345                 350

Tyr Val Leu Gly Ser Ala His Gln Gly Cys Leu Pro Pro Phe Pro Ala
                        355                 360                 365

Asp Val Phe Met Ile Pro Gln Tyr Gly Tyr Leu Thr Leu Asn Asn Gly
                        370                 375                 380

Ser Gln Ala Val Gly Arg Ser Ser Phe Tyr Cys Leu Glu Tyr Phe Pro
        385                 390                 395                 400

Ser Gln Met Leu Arg Thr Gly Asn Asn Phe Thr Phe Ser Tyr Thr Phe
                        405                 410                 415

Glu Glu Val Pro Phe His Ser Ser Tyr Ala His Ser Gln Ser Leu Asp
                        420                 425                 430

Arg Leu Met Asn Pro Leu Ile Asp Gln Tyr Leu Tyr Tyr Leu Asn Arg
                        435                 440                 445

Thr Gln Asn Gln Ser Gly Ser Ala Gln Asn Lys Asp Leu Leu Phe Ser
                        450                 455                 460

Arg Gly Ser Pro Ala Gly Met Ser Val Gln Pro Lys Asn Trp Leu Pro
        465                 470                 475                 480

Gly Pro Cys Tyr Arg Gln Gln Arg Val Ser Lys Thr Lys Thr Asp Asn
                        485                 490                 495

Asn Asn Ser Asn Phe Thr Trp Thr Gly Ala Ser Lys Tyr Asn Leu Asn
                        500                 505                 510

Gly Arg Glu Ser Ile Ile Asn Pro Gly Thr Ala Met Ala Ser His Lys
                        515                 520                 525

Asp Asp Glu Asp Lys Phe Phe Pro Met Ser Gly Val Met Ile Phe Gly
                        530                 535                 540

Lys Glu Ser Ala Gly Ala Ser Asn Thr Ala Leu Asp Asn Val Met Ile
        545                 550                 555                 560

Thr Asp Glu Glu Glu Ile Lys Ala Thr Asn Pro Val Ala Thr Glu Arg
                        565                 570                 575

Phe Gly Thr Val Ala Val Asn Phe Gln Ser Ser Ser Thr Asp Pro Ala
                        580                 585                 590

Thr Gly Asp Val His Ala Met Gly Ala Leu Pro Gly Met Val Trp Gln
                        595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
        625                 630                 635                 640

Lys Asn Pro Pro Pro Gln Ile Leu Ile Lys Asn Thr Pro Val Pro Ala
                        645                 650                 655

Asn Pro Pro Ala Glu Phe Ser Ala Thr Lys Phe Ala Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Val Gln Tyr Thr Ser Asn
                        690                 695                 700

Tyr Ala Lys Ser Ala Asn Val Asp Phe Thr Val Asp Asn Asn Gly Leu
        705                 710                 715                 720

Tyr Thr Glu Pro Arg Pro Ile Gly Thr Arg Tyr Leu Thr Arg Pro Leu
                        725                 730                 735
```

<210> SEQ ID NO 2
<211> LENGTH: 735
<212> TYPE: PRT
<213> ORGANISM: Adeno-associated virus - 2

<400> SEQUENCE: 2

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Arg
65                  70                  75                  80

Gln Leu Asp Ser Gly Asp Asn Pro Tyr Leu Lys Tyr Asn His Ala Asp
            85                  90                  95

Ala Glu Phe Gln Glu Arg Leu Lys Glu Asp Thr Ser Phe Gly Gly Asn
        100                 105                 110

Leu Gly Arg Ala Val Phe Gln Ala Lys Lys Arg Val Leu Glu Pro Leu
    115                 120                 125

Gly Leu Val Glu Glu Pro Val Lys Thr Ala Pro Gly Lys Lys Arg Pro
130                 135                 140

Val Glu His Ser Pro Val Glu Pro Asp Ser Ser Ser Gly Thr Gly Lys
145                 150                 155                 160

Ala Gly Gln Gln Pro Ala Arg Lys Arg Leu Asn Phe Gly Gln Thr Gly
            165                 170                 175

Asp Ala Asp Ser Val Pro Asp Pro Gln Pro Leu Gly Gln Pro Pro Ala
        180                 185                 190

Ala Pro Ser Gly Leu Gly Thr Asn Thr Met Ala Thr Gly Ser Gly Ala
    195                 200                 205

Pro Met Ala Asp Asn Asn Glu Gly Ala Asp Gly Val Gly Asn Ser Ser
210                 215                 220

Gly Asn Trp His Cys Asp Ser Thr Trp Met Gly Asp Arg Val Ile Thr
225                 230                 235                 240

Thr Ser Thr Arg Thr Trp Ala Leu Pro Thr Tyr Asn Asn His Leu Tyr
            245                 250                 255

Lys Gln Ile Ser Ser Gln Ser Gly Ala Ser Asn Asp Asn His Tyr Phe
        260                 265                 270

Gly Tyr Ser Thr Pro Trp Gly Tyr Phe Asp Phe Asn Arg Phe His Cys
    275                 280                 285

His Phe Ser Pro Arg Asp Trp Gln Arg Leu Ile Asn Asn Asn Trp Gly
290                 295                 300

Phe Arg Pro Lys Arg Leu Asn Phe Lys Leu Phe Asn Ile Gln Val Lys
305                 310                 315                 320

Glu Val Thr Gln Asn Asp Gly Thr Thr Thr Ile Ala Asn Asn Leu Thr
            325                 330                 335

Ser Thr Val Gln Val Phe Thr Asp Ser Glu Tyr Gln Leu Pro Tyr Val
        340                 345                 350

Leu Gly Ser Ala His Gln Gly Cys Leu Pro Pro Phe Pro Ala Asp Val
    355                 360                 365

Phe Met Val Pro Gln Tyr Gly Tyr Leu Thr Leu Asn Asn Gly Ser
```

```
                370                 375                 380
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Adeno-associated virus - 3

<400> SEQUENCE: 3

Met Ala Ala Asp Gly Tyr Leu Pro Asp Trp Leu Glu Asp Asn Leu Ser
1               5                   10                  15
```

-continued

Glu Gly Ile Arg Glu Trp Trp Ala Leu Lys Pro Gly Val Gln Pro
             20                  25                  30

Lys Ala Asn Gln Gln His Gln Asp Asn Arg Arg Gly Leu Val Leu Pro
         35                  40                  45

Gly Tyr Lys Tyr Leu Gly Pro Gly Asn Gly Leu Asp Lys Gly Glu Pro
     50                  55                  60

Val Asn Glu Ala Asp Ala Ala Leu Glu His Asp Lys Ala Tyr Asp
65              70                  75                  80

Gln Gln Leu Lys Ala Gly Asp Asn Pro Tyr Leu Lys Tyr Asn His Ala
             85                  90                  95

Asp Ala Glu Phe Gln Glu Arg Leu Gln Glu Asp Thr Ser Phe Gly Gly
         100                 105                 110

Asn Leu Gly Arg Ala Val Phe Gln Ala Lys Lys Arg Ile Leu Glu Pro
     115                 120                 125

Leu Gly Leu Val Glu Glu Ala Ala Lys Thr Ala Pro Gly Lys Lys Gly
     130                 135                 140

Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
             165                 170                 175

Gly Asp Ser Glu Ser Val Pro Asp Pro Gln Pro Leu Gly Glu Pro Pro
         180                 185                 190

Ala Ala Pro Thr Ser Leu Gly Ser Asn Thr Met Ala Ser Gly Gly Gly
     195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
             245                 250                 255

Tyr Lys Gln Ile Ser Ser Gln Ser Gly Ala Ser Asn Asp Asn His Tyr
         260                 265                 270

Phe Gly Tyr Ser Thr Pro Trp Gly Tyr Phe Asp Phe Asn Arg Phe His
     275                 280                 285

Cys His Phe Ser Pro Arg Asp Trp Gln Arg Leu Ile Asn Asn Asn Trp
     290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
             325                 330                 335

Thr Ser Thr Val Gln Val Phe Thr Asp Ser Glu Tyr Gln Leu Pro Tyr
         340                 345                 350

Val Leu Gly Ser Ala His Gln Gly Cys Leu Pro Pro Phe Pro Ala Asp
     355                 360                 365

Val Phe Met Val Pro Gln Tyr Gly Tyr Leu Thr Leu Asn Asn Gly Ser
     370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
             405                 410                 415

Asp Val Pro Phe His Ser Ser Tyr Ala His Ser Gln Ser Leu Asp Arg
         420                 425                 430

Leu Met Asn Pro Leu Ile Asp Gln Tyr Leu Tyr Tyr Leu Asn Arg Thr

```
            435                 440                 445
Gln Gly Thr Thr Ser Gly Thr Thr Asn Gln Ser Arg Leu Leu Phe Ser
    450                 455                 460
Gln Ala Gly Pro Gln Ser Met Ser Leu Gln Ala Arg Asn Trp Leu Pro
465                 470                 475                 480
Gly Pro Cys Tyr Arg Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Gly Thr Val Asn His Gln Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 4
<211> LENGTH: 734
<212> TYPE: PRT
<213> ORGANISM: Adeno-associated virus - 4

<400> SEQUENCE: 4

Met Thr Asp Gly Tyr Leu Pro Asp Trp Leu Glu Asp Asn Leu Ser Glu
1               5                   10                  15
Gly Val Arg Glu Trp Trp Ala Leu Gln Pro Gly Ala Pro Lys Pro Lys
                20                  25                  30
Ala Asn Gln Gln His Gln Asp Asn Ala Arg Gly Leu Val Leu Pro Gly
            35                  40                  45
Tyr Lys Tyr Leu Gly Pro Gly Asn Gly Leu Asp Lys Gly Glu Pro Val
        50                  55                  60
Asn Ala Ala Asp Ala Ala Ala Leu Glu His Asp Lys Ala Tyr Asp Gln
65                  70                  75                  80
```

```
Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
            115                 120                 125

Gly Leu Val Glu Gln Ala Gly Glu Thr Ala Pro Gly Lys Lys Arg Pro
130                 135                 140

Leu Ile Glu Ser Pro Gln Pro Asp Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
            195                 200                 205

Gly Gln Gly Ala Asp Gly Val Gly Asn Ala Ser Gly Asp Trp His Cys
210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
            290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Gln Thr Asp Arg Asn
            370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
```

```
                    500                 505                 510
Arg Trp Ser Ala Leu Thr Pro Gly Pro Pro Met Ala Thr Ala Gly Pro
                515                 520                 525

Ala Asp Ser Lys Phe Ser Asn Ser Gln Leu Ile Phe Ala Gly Pro Lys
            530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
                595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
                675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 5
<211> LENGTH: 724
<212> TYPE: PRT
<213> ORGANISM: Adeno-associated virus - 5

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140
```

```
Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
```

```
                        565                 570                 575
Thr Thr Ala Pro Ala Thr Gly Thr Tyr Asn Leu Gln Glu Ile Val Pro
                    580                 585                 590

Gly Ser Val Trp Met Glu Arg Asp Val Tyr Leu Gln Gly Pro Ile Trp
                595                 600                 605

Ala Lys Ile Pro Glu Thr Gly Ala His Phe His Pro Ser Pro Ala Met
            610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 736
<212> TYPE: PRT
<213> ORGANISM: Adeno-associated virus - 6

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
```

```
                210                 215                 220
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
                450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
                515                 520                 525

Asp Asp Lys Asp Lys Phe Phe Pro Met Ser Gly Val Met Ile Phe Gly
                530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
                580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640
```

```
Lys His Pro Pro Gln Ile Leu Ile Lys Asn Thr Pro Val Pro Ala
                645             650             655

Asn Pro Pro Ala Glu Phe Ser Ala Thr Lys Phe Ala Ser Phe Ile Thr
            660             665             670

Gln Tyr Ser Thr Gly Gln Val Ser Val Glu Ile Glu Trp Glu Leu Gln
            675             680             685

Lys Glu Asn Ser Lys Arg Trp Asn Pro Glu Val Gln Tyr Thr Ser Asn
            690             695             700

Tyr Ala Lys Ser Ala Asn Val Asp Phe Thr Val Asp Asn Asn Gly Leu
705             710             715                 720

Tyr Thr Glu Pro Arg Pro Ile Gly Thr Arg Tyr Leu Thr Arg Pro Leu
                725             730             735
```

<210> SEQ ID NO 7
<211> LENGTH: 737
<212> TYPE: PRT
<213> ORGANISM: Adeno-associated virus - 7

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
```

```
                275                 280                 285
Phe His Cys His Phe Ser Pro Arg Asp Trp Gln Arg Leu Ile Asn Asn
290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Ile Gln Val Phe Ser Asp Ser Glu Tyr Gln Leu
            340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ala
            435                 440                 445
Arg Thr Gln Ser Asn Pro Gly Gly Thr Ala Gly Asn Arg Glu Leu Gln
450                 455                 460
Phe Tyr Gln Gly Gly Pro Ser Thr Met Ala Glu Gln Ala Lys Asn Trp
465                 470                 475                 480
Leu Pro Gly Pro Cys Phe Arg Gln Gln Arg Val Ser Lys Thr Leu Asp
                485                 490                 495
Gln Asn Asn Asn Ser Asn Phe Ala Trp Thr Gly Ala Thr Lys Tyr His
            500                 505                 510
Leu Asn Gly Arg Asn Ser Leu Val Asn Pro Gly Val Ala Met Ala Thr
            515                 520                 525
His Lys Asp Asp Glu Asp Arg Phe Phe Pro Ser Ser Gly Val Leu Ile
530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
                565                 570                 575
Glu Tyr Gly Ile Val Ser Ser Asn Leu Gln Ala Ala Asn Thr Ala Ala
            580                 585                 590
Gln Thr Gln Val Val Asn Asn Gln Gly Ala Leu Pro Gly Met Val Trp
            595                 600                 605
Gln Asn Arg Asp Val Tyr Leu Gln Gly Pro Ile Trp Ala Lys Ile Pro
610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Glu Val Phe Thr Pro Ala Lys Phe Ala Ser Phe Ile
            660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Ile Gln Tyr Thr Ser
            690                 695                 700
```

```
Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 8
<211> LENGTH: 738
<212> TYPE: PRT
<213> ORGANISM: Adeno-associated virus - 8

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335
```

```
Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
                530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

```
<210> SEQ ID NO 9
<211> LENGTH: 736
<212> TYPE: PRT
<213> ORGANISM: Adeno-associated virus 9

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380
```

```
Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 10
<211> LENGTH: 738
<212> TYPE: PRT
<213> ORGANISM: Adeno-associated virus 10

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
             115                 120                 125

Leu Gly Leu Val Glu Glu Ala Ala Lys Thr Ala Pro Gly Lys Lys Arg
 130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                 165                 170                 175

Thr Gly Glu Ser Glu Ser Val Pro Asp Pro Gln Pro Ile Gly Glu Pro
             180                 185                 190

Pro Ala Gly Pro Ser Gly Leu Gly Ser Gly Thr Met Ala Ala Gly Gly
             195                 200                 205

Gly Ala Pro Met Ala Asp Asn Asn Glu Gly Ala Asp Gly Val Gly Ser
 210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                 245                 250                 255

Leu Tyr Lys Gln Ile Ser Asn Gly Thr Ser Gly Gly Ser Thr Asn Asp
             260                 265                 270

Asn Thr Tyr Phe Gly Tyr Ser Thr Pro Trp Gly Tyr Phe Asp Phe Asn
             275                 280                 285

Arg Phe His Cys His Phe Ser Pro Arg Asp Trp Gln Arg Leu Ile Asn
             290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                 325                 330                 335

Asn Asn Leu Thr Ser Thr Ile Gln Val Phe Thr Asp Ser Glu Tyr Gln
             340                 345                 350

Leu Pro Tyr Val Leu Gly Ser Ala His Gln Gly Cys Leu Pro Pro Phe
             355                 360                 365

Pro Ala Asp Val Phe Met Ile Pro Gln Tyr Gly Tyr Leu Thr Leu Asn
 370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
             405                 410                 415

Thr Phe Glu Asp Val Pro Phe His Ser Ser Tyr Ala His Ser Gln Ser
             420                 425                 430

Leu Asp Arg Leu Met Asn Pro Leu Ile Asp Gln Tyr Leu Tyr Tyr Leu
             435                 440                 445
```

-continued

```
Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
                580                 585                 590

Pro Ile Val Gly Asn Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 11
<211> LENGTH: 7
<212> TYPE: PRT
<213> ORGANISM: Artificial Sequence
<220> FEATURE:
<223> OTHER INFORMATION: rAAV peptide insert

<400> SEQUENCE: 11

```
Leu Gly Glu Thr Thr Arg Pro
1               5
```

<210> SEQ ID NO 12
<211> LENGTH: 7
<212> TYPE: PRT
<213> ORGANISM: Artificial Sequence
<220> FEATURE:
<223> OTHER INFORMATION: rAAV peptide insert

<400> SEQUENCE: 12

Asn Glu Thr Ile Thr Arg Pro
1               5

<210> SEQ ID NO 13
<211> LENGTH: 10
<212> TYPE: PRT
<213> ORGANISM: Artificial Sequence
<220> FEATURE:
<223> OTHER INFORMATION: rAAV peptide insert

<400> SEQUENCE: 13

Leu Ala Leu Gly Glu Thr Thr Arg Pro Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: LANETITRPA

<400> SEQUENCE: 14

Leu Ala Asn Glu Thr Ile Thr Arg Pro Ala
1               5                   10

<210> SEQ ID NO 15
<211> LENGTH: 10
<212> TYPE: PRT
<213> ORGANISM: Artificial Sequence
<220> FEATURE:
<223> OTHER INFORMATION: rAAV peptide insert

<400> SEQUENCE: 15

Ala Ala Leu Gly Glu Thr Thr Arg Pro Ala
1               5                   10

<210> SEQ ID NO 16
<211> LENGTH: 10
<212> TYPE: PRT
<213> ORGANISM: Artificial Sequence
<220> FEATURE:
<223> OTHER INFORMATION: rAAV peptide insert

<400> SEQUENCE: 16

Ala Ala Asn Glu Thr Ile Thr Arg Pro Ala
1               5                   10

<210> SEQ ID NO 17
<211> LENGTH: 9
<212> TYPE: PRT
<213> ORGANISM: Artificial Sequence
<220> FEATURE:
<223> OTHER INFORMATION: rAAV peptide insert

<400> SEQUENCE: 17

Gly Leu Gly Glu Thr Thr Arg Pro Ala
1               5

<210> SEQ ID NO 18
<211> LENGTH: 9
<212> TYPE: PRT
<213> ORGANISM: Artificial Sequence
<220> FEATURE:
<223> OTHER INFORMATION: rAAV peptide insert

<400> SEQUENCE: 18

Gly Asn Glu Thr Ile Thr Arg Pro Ala

<210> SEQ ID NO 19
<211> LENGTH: 745
<212> TYPE: PRT
<213> ORGANISM: Artificial Sequence
<220> FEATURE:
<223> OTHER INFORMATION: Variant VP1 capsid protein with peptide
      insertion

<400> SEQUENCE: 19

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro

```
Val Leu Gly Ser Ala His Gln Gly Cys Leu Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Leu Gly Glu
            580                 585                 590

Thr Thr Arg Pro Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
610                 615                 620

Gly Pro Ile Trp Ala Lys Ile Pro His Thr Asp Gly His Phe His Pro
625                 630                 635                 640

Ser Pro Leu Met Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 20
<211> LENGTH: 11
<212> TYPE: PRT
```

```
<213> ORGANISM: Artificial Sequence
<220> FEATURE:
<223> OTHER INFORMATION: Peptide Insertion Formula I
<220> FEATURE:
<221> NAME/KEY: MISC_FEATURE
<222> LOCATION: (1)..(2)
<223> OTHER INFORMATION: Xaa = Ala, Leu, Gly, Ser, Thr or is absent
<220> FEATURE:
<221> NAME/KEY: MISC_FEATURE
<222> LOCATION: (3)..(3)
<223> OTHER INFORMATION: Xaa = Leu, Asn and Lys
<220> FEATURE:
<221> NAME/KEY: MISC_FEATURE
<222> LOCATION: (4)..(4)
<223> OTHER INFORMATION: Xaa = Gly, Glu, Ala and Asp
<220> FEATURE:
<221> NAME/KEY: MISC_FEATURE
<222> LOCATION: (5)..(5)
<223> OTHER INFORMATION: Xaa = Glu, Thr, Gly and Pro
<220> FEATURE:
<221> NAME/KEY: MISC_FEATURE
<222> LOCATION: (6)..(6)
<223> OTHER INFORMATION: Xaa = Thr, Ile, Gln, and Lys
<220> FEATURE:
<221> NAME/KEY: MISC_FEATURE
<222> LOCATION: (7)..(7)
<223> OTHER INFORMATION: Xaa = Thr and Ala
<220> FEATURE:
<221> NAME/KEY: MISC_FEATURE
<222> LOCATION: (8)..(8)
<223> OTHER INFORMATION: Xaa = Arg, Asn and Thr
<220> FEATURE:
<221> NAME/KEY: MISC_FEATURE
<222> LOCATION: (9)..(9)
<223> OTHER INFORMATION: Xaa = Pro and Asn
<220> FEATURE:
<221> NAME/KEY: MISC_FEATURE
<222> LOCATION: (10)..(11)
<223> OTHER INFORMATION: Xaa = Ala, Leu, Gly, Ser, Thr or is absent

<400> SEQUENCE: 20

Xaa Xaa Xaa Xaa Xaa Xaa Xaa Xaa Xaa Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Peptide Insertion Formula II
<220> FEATURE:
<221> NAME/KEY: MISC_FEATURE
<222> LOCATION: (1)..(2)
<223> OTHER INFORMATION: Xaa = Ala, Leu, Gly, Ser, Thr or is absent
<220> FEATURE:
<221> NAME/KEY: MISC_FEATURE
<222> LOCATION: (3)..(6)
<223> OTHER INFORMATION: Xaa = any amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 21

Xaa Xaa Xaa Xaa Xaa Xaa Thr Arg Pro Xaa Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Peptide Insertion Formula III
<220> FEATURE:
<221> NAME/KEY: MISC_FEATURE
```

```
<222> LOCATION: (1)..(2)
<223> OTHER INFORMATION: Xaa = Ala, Leu, Gly, Ser, Thr or is absent
<220> FEATURE:
<221> NAME/KEY: MISC_FEATURE
<222> LOCATION: (3)..(3)
<223> OTHER INFORMATION: Xaa = Leu and Asn
<220> FEATURE:
<221> NAME/KEY: MISC_FEATURE
<222> LOCATION: (4)..(4)
<223> OTHER INFORMATION: Xaa = Gly and Glu
<220> FEATURE:
<221> NAME/KEY: MISC_FEATURE
<222> LOCATION: (5)..(5)
<223> OTHER INFORMATION: Xaa = Glu and Thr
<220> FEATURE:
<221> NAME/KEY: MISC_FEATURE
<222> LOCATION: (6)..(6)
<223> OTHER INFORMATION: Xaa = Thr and Ile
<220> FEATURE:
<221> NAME/KEY: MISC_FEATURE
<222> LOCATION: (10)..(11)
<223> OTHER INFORMATION: Xaa = Ala, Leu, Gly, Ser, Thr or is absent

<400> SEQUENCE: 22

Xaa Xaa Xaa Xaa Xaa Xaa Thr Arg Pro Xaa Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Peptide Insertion Formula IV
<220> FEATURE:
<221> NAME/KEY: MISC_FEATURE
<222> LOCATION: (1)..(2)
<223> OTHER INFORMATION: Xaa = Ala, Leu, Gly, Ser, Thr or is absent
<220> FEATURE:
<221> NAME/KEY: MISC_FEATURE
<222> LOCATION: (3)..(3)
<223> OTHER INFORMATION: Xaa = Leu, Asn, Arg, Ala, Ser and Lys
<220> FEATURE:
<221> NAME/KEY: MISC_FEATURE
<222> LOCATION: (4)..(4)
<223> OTHER INFORMATION: Xaa =Gly, Glu, Ala, Val, Thr and Asp
<220> FEATURE:
<221> NAME/KEY: MISC_FEATURE
<222> LOCATION: (5)..(5)
<223> OTHER INFORMATION: Xaa = Glu, Thr, Gly, Asp and Pro
<220> FEATURE:
<221> NAME/KEY: MISC_FEATURE
<222> LOCATION: (6)..(6)
<223> OTHER INFORMATION: Xaa = Thr, Ile, Gly, Lys, Asp and Gln
<220> FEATURE:
<221> NAME/KEY: MISC_FEATURE
<222> LOCATION: (7)..(7)
<223> OTHER INFORMATION: Xaa = Thr, Ser, Val and Ala
<220> FEATURE:
<221> NAME/KEY: MISC_FEATURE
<222> LOCATION: (8)..(8)
<223> OTHER INFORMATION: Xaa = Arg, Val, Lys, Pro, Thr and Asn
<220> FEATURE:
<221> NAME/KEY: MISC_FEATURE
<222> LOCATION: (9)..(9)
<223> OTHER INFORMATION: Xaa = Pro, Gly, Phe, Asn and Arg
<220> FEATURE:
<221> NAME/KEY: MISC_FEATURE
<222> LOCATION: (10)..(11)
<223> OTHER INFORMATION: Xaa = Ala, Leu, Gly, Ser, Thr or is absent

<400> SEQUENCE: 23

Xaa Xaa Xaa Xaa Xaa Xaa Xaa Xaa Xaa Xaa Xaa
1               5                   10

<210> SEQ ID NO 24
```

```
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 24
gacttgatct tctgttagcc ctaatcatca attagc                                  36

<210> SEQ ID NO 25
<211> LENGTH: 1565
<212> TYPE: DNA
<213> ORGANISM: Homo sapiens

<400> SEQUENCE: 25
cctacagcag ccagggtgag attatgaggc tgagctgaga atatcaagac tgtaccgagt         60
agggggcctt ggcaagtgtg gagagcccgg cagctggggc agagggcgga gtacggtgtg        120
cgtttacgga cctcttcaaa cgaggtagga aggtcagaag tcaaaaaggg aacaaatgat        180
gtttaaccac acaaaaatga aaatccaatg gttggatatc cattccaaat acacaaaggc        240
aacggataag tgatccgggc caggcacaga aggccatgca cccgtaggat tgcactcaga        300
gctcccaaat gcataggaat agaagggtgg gtgcaggagg ctgaggggtg gggaaagggc        360
atgggtgttt catgaggaca gagcttccgt ttcatgcaat gaaaagagtt tggagacgga        420
tggtggtgac tggactatac acttacacac ggtagcgatg gtacactttg tattatgtat        480
attttaccac gatctttta aagtgtcaaa ggcaaatggc caaatggttc cttgtcctat         540
agctgtagca gccatcggct gttagtgaca aagcccctga gtcaagatga cagcagcccc        600
cataactcct aatcggctct cccgcgtgga gtcatttagg agtagtcgca ttagagacaa        660
gtccaacatc taatcttcca ccctggccag ggccccagct ggcagcgagg gtgggagact        720
ccgggcagag cagagggcgc tgacattggg gcccggcctg gcttgggtcc ctctggcctt        780
tccccagggg ccctctttcc ttggggcttt cttgggccgc cactgctccc gctcctctcc        840
ccccatccca ccccctcacc ccctcgttct tcatatcctt ctctagtgct ccctccactt        900
tcatccaccc ttctgcaaga gtgtgggacc acaaatgagt tttcacctgg cctggggaca        960
cacgtgcccc cacaggtgct gagtgacttt ctaggacagt aatctgcttt aggctaaaat       1020
gggacttgat cttctgttag ccctaatcat caattagcag agccggtgaa ggtgcagaac       1080
ctaccgcctt tccaggcctc ctcccacctc tgccacctcc actctccttc ctgggatgtg       1140
ggggctggca cacgtgtggc ccagggcatt ggtgggattg cactgagctg ggtcattagc       1200
gtaatcctgg acaagggcag acagggcgag cggagggcca gctccggggc tcaggcaagg       1260
ctggggcctt cccccagaca ccccactcct cctctgctgg accccactt cataggcac         1320 ttcgtgttct caagggctt ccaaatagca tggtggcctt ggatgcccag ggaagcctca       1380
gagttgctta tctccctcta gacagaaggg gaatctcggt caagagggag aggtcgccct       1440
gttcaaggcc acccagccag ctcatggcgg taatgggaca aggctggcca gccatcccac       1500
cctcagaagg gacccggtgg ggcaggtgat ctcagaggag gctcacttct gggtctcaca       1560
ttctt                                                                   1565

<210> SEQ ID NO 26
<211> LENGTH: 149
<212> TYPE: DNA
<213> ORGANISM: Homo sapiens

<400> SEQUENCE: 26
```

```
ccagcaaatc cctctgagcc gcccccgggg gctcgcctca ggagcaagga agcaagggt      60 gggaggagga ggtctaagtc ccaggcccaa ttaagagatc agatggtgta ggatttggga    120
gcttttaagg tgaagaggcc cgggctgat                                      149
```

<210> SEQ ID NO 27
<211> LENGTH: 1958
<212> TYPE: DNA
<213> ORGANISM: Artificial Sequence
<220> FEATURE:
<223> OTHER INFORMATION: Cassette comprising optimized enhance,
      optimized promoter, optimized 5'UTR, optimized intron, optimized
      kozak and optimized polyA region

<400> SEQUENCE: 27

```
cctacagcag ccagggtgag attatgaggc tgagctgaga atatcaagac tgtaccgagt      60
agggggcctt ggcaagtgtg gagagcccgg cagctggggc agagggcgga gtacggtgtg    120
cgtttacgga cctcttcaaa cgaggtagga aggtcagaag tcaaaaaggg aacaaatgat    180
gtttaaccac acaaaaatga aaatccaatg gttggatatc cattccaaat acacaaaggc    240
aacggataag tgatccgggc caggcacaga aggccatgca cccgtaggat tgcactcaga    300
gctcccaaat gcataggaat agaagggtgg gtgcaggagg ctgaggggtg gggaaagggc    360
atgggtgttt catgaggaca gagcttccgt ttcatgcaat gaaagagtt tggagacgga    420 tggtggtgac tggactatac acttacacac ggtagcgatg gtacactttg tattatgtat    480
attttaccac gatctttta aagtgtcaaa ggcaaatggc caaatggttc cttgtcctat    540
agctgtagca gccatcggct gttagtgaca agcccctga gtcaagatga cagcagcccc    600
cataactcct aatcggctct cccgcgtgga gtcatttagg agtagtcgca ttagagacaa    660
gtccaacatc taatcttcca ccctggccag ggccccagct ggcagcgagg gtgggagact    720
ccgggcagag cagagggcgc tgacattggg gcccggcctg gcttgggtcc ctctggcctt    780
tcccaggggg ccctctttcc ttggggcttt cttgggccgc cactgctccc gctcctctcc    840
ccccatccca cccctcacc cctcgttcct tcatatcctt ctctagtgct ccctccactt    900
tcatccaccc ttctgcaaga gtgtgggacc acaaatgagt tttcacctgg cctggggaca    960
cacgtgcccc cacaggtgct gagtgacttt ctaggacagt aatctgcttt aggctaaaat   1020
gggacttgat cttctgttag ccctaatcat caattagcag agccggtgaa ggtgcagaac   1080
ctaccgcctt tccaggcctc ctcccacctc tgccacctcc actctccttc ctgggatgtg   1140
ggggctggca cacgtgtggc ccagggcatt ggtgggattg cactgagctg ggtcattagc   1200
gtaatcctgg acaagggcag acagggcgag cggagggcca gctccggggc tcaggcaagg   1260
ctgggggctt cccccagaca ccccactcct cctctgctgg accccacttc atagggcac   1320 ttcgtgttct caaagggctt ccaaatagca tggtggcctt ggatgcccag ggaagcctca   1380
gagttgctta tctccctcta gacagaaggg gaatctcggt caagaggag aggtcgccct   1440 gttcaaggcc acccagccag ctcatggcgg taatgggaca aggctggcca gccatcccac   1500
cctcagaagg gacccggtgg ggcaggtgat ctcagaggag gctcacttct gggtctcaca   1560
ttcttccagc aaatccctct gagccgcccc cggggctcg cctcaggagc aaggaagcaa   1620
ggggtgggag gaggaggtct aagtcccagg cccaattaag agatcagatg gtgtaggatt   1680
tgggagcttt taaggtgaag aggcccgggc tgatcccact ggccggtata agcaccgtg   1740 accctcaggt gacgcaccag ggccggctgc cgtcggggac agggctttcc atagcccagg   1800
```

```
taagtatcaa ggttacaaga caggtttaag gagaccaata gaaactgggc ttgtcgagac    1860
agagaagact cttgcgtttc tgataggcac ctattggtct tactgacatc cactttgcct    1920
ttctctccac aggcccagag aggagacagg ccgccacc                            1958

<210> SEQ ID NO 28
<211> LENGTH: 102
<212> TYPE: DNA
<213> ORGANISM: Artificial Sequence
<220> FEATURE:
<223> OTHER INFORMATION: Synthesized 5'UTR

<400> SEQUENCE: 28
cccactggcc ggtataaagc accgtgaccc tcaggtgacg caccagggcc ggctgccgtc      60
ggggacaggg ctttccatag cccaggccca gagaggagac ag                       102

<210> SEQ ID NO 29
<211> LENGTH: 133
<212> TYPE: DNA
<213> ORGANISM: Artificial Sequence
<220> FEATURE:
<223> OTHER INFORMATION: MNTC intron sequence

<400> SEQUENCE: 29
gtaagtatca aggttacaag acaggtttaa ggagaccaat agaaactggg cttgtcgaga      60
cagagaagac tcttgcgttt ctgataggca cctattggtc ttactgacat ccactttgcc     120
tttctctcca cag                                                       133

<210> SEQ ID NO 30
<211> LENGTH: 13
<212> TYPE: DNA
<213> ORGANISM: Artificial Sequence
<220> FEATURE:
<223> OTHER INFORMATION: Translation initiation sequence
<220> FEATURE:
<221> NAME/KEY: misc_feature
<222> LOCATION: (7)..(7)
<223> OTHER INFORMATION: n is A or G

<400> SEQUENCE: 30
gccgccncca tgg                                                        13

<210> SEQ ID NO 31
<211> LENGTH: 235
<212> TYPE: DNA
<213> ORGANISM: Artificial Sequence
<220> FEATURE:
<223> OTHER INFORMATION: Synthetic construct  poly A region

<400> SEQUENCE: 31
ggccgcgggg atccagacat gataagatac attgatgagt ttggacaaac cacaactaga      60
atgcagtgaa aaaatgctt tatttgtgaa atttgtgatg ctattgcttt atttgtaacc     120
attataagct gcaataaaca agttaacaac aacaattgca ttcattttat gtttcaggtt     180 caggggggaga tgtgggaggt ttttaaagc aagtaaaacc tctacaaatg tggta          235
```

That which is claimed is:

1. A method for delivering a polynucleotide of interest to a cone photoreceptor in a subject, the method comprising:

delivering into the vitreous of the eye an effective amount of recombinant adeno-associated virus (rAAV) variant comprising the polynucleotide of interest, wherein:

a) the rAAV variant comprises a variant AAV capsid protein comprising the amino acid sequence LGETTRP (SEQ ID NO:11) inserted into the GH loop of the VP1 capsid protein; and b) the polynucleotide of interest comprises a regulatory cassette operably linked to a polynucleotide sequence encoding a therapeutic protein, wherein the regulatory cassette comprises the sequence:

(SEQ ID NO: 27)
CCTACAGCAGCCAGGGTGAGATTATGAGGCTGAGCTGAGAATATCAAGACT

GTACCGAGTAGGGGGCCTTGGCAAGTGTGGAGAGCCCGGCAGCTGGGGCAG

AGGGCGGAGTACGGTGTGCGTTTACGGACCTCTTCAAACGAGGTAGGAAGG

TCAGAAGTCAAAAAGGGAACAAATGATGTTTAACCACACAAAAATGAAAAT

CCAATGGTTGGATATCCATTCCAAATACACAAAGGCAACGGATAAGTGATC

CGGGCCAGGCACAGAAGGCCATGCACCCGTAGGATTGCACTCAGAGCTCCC

AAATGCATAGGAATAGAAGGGTGGGTGCAGGAGGCTGAGGGGTGGGGAAAG

GGCATGGGTGTTTCATGAGGACAGAGCTTCCGTTTCATGCAATGAAAAGAG

TTTGGAGACGGATGGTGGTGACTGGACTATACACTTACACACGGTAGCGAT

GGTACACTTTGTATTATGTATATTTTACCACGATCTTTTTAAAGTGTCAAA

GGCAAATGGCCAAATGGTTCCTTGTCCTATAGCTGTAGCAGCCATCGGCTG

TTAGTGACAAAGCCCCTGAGTCAAGATGACAGCAGCCCCCATAACTCCTAA

TCGGCTCTCCCGCGTGGAGTCATTTAGGAGTAGTCGCATTAGAGACAAGTC

CAACATCTAATCTTCCACCCTGGCCAGGGCCCCAGCTGGCAGCGAGGGTGG

GAGACTCCGGGCAGAGCAGAGGGCGCTGACATTGGGCCCGGCCTGGCTTG

GGTCCCTCTGGCCTTTCCCCAGGGGCCCTCTTTCCTTGGGGCTTTCTTGGG

CCGCCACTGCTCCCGCTCCTCTCCCCCATCCCACCCCCTCACCCCCTCGT

TCTTCATATCCTTCTCTAGTGCTCCCTCCACTTTCATCCACCCTTCTGCAA

GAGTGTGGGACCACAAATGAGTTTTCACCTGGCCTGGGGACACACGTGCCC

CCACAGGTGCTGAGTGACTTTCTAGGACAGTAATCTGCTTTAGGCTAAAAT

GGGACTTGATCTTCTGTTAGCCCTAATCATCAATTAGCAGAGCCGGTGAAG

GTGCAGAACCTACCGCCTTTCCAGGCCTCCTCCCACCTCTGCCACCTCCAC

TCTCCTTCCTGGGATGTGGGGGCTGGCACACGTGTGGCCCAGGGCATTGGT

GGGATTGCACTGAGCTGGGTCATTAGCGTAATCCTGGACAAGGGCAGACAG

GGCGAGCGGAGGGCCAGCTCCGGGGCTCAGGCAAGGCTGGGGGCTTCCCCC

AGACACCCCACTCCTCCTCTGCTGGACCCCCACTTCATAGGGCACTTCGTG

TTCTCAAAGGGCTTCCAAATAGCATGGTGGCCTTGGATGCCCAGGGAAGCC

TCAGAGTTGCTTATCTCCCTCTAGACAGAAGGGGAATCTCGGTCAAGAGGG

AGAGGTCGCCCTGTTCAAGGCCACCCAGCCAGCTCATGGCGGTAATGGGAC

AAGGCTGGCCAGCCATCCCACCCTCAGAAGGGACCCGGTGGGGCAGGTGAT

CTCAGAGGAGGCTCACTTCTGGGTCTCACATTCTTCCAGCAAATCCCTCTG

AGCCGCCCCGGGGGCTCGCCTCAGGAGCAAGGAAGCAAGGGGTGGGAGGA

GGAGGTCTAAGTCCCAGGCCCAATTAAGAGATCAGATGGTGTAGGATTTGG

GAGCTTTTAAGGTGAAGAGGCCCGGGCTGATCCCACTGGCCGGTATAAAGC

ACCGTGACCCTCAGGTGACGCACCAGGGCCGGCTGCCGTCGGGACAGGGC

TTTCCATAGCCCAGGTAAGTATCAAGGTTACAAGACAGGTTTAAGGAGACC

AATAGAAACTGGGCTTGTCGAGACAGAGAAGACTCTTGCGTTTCTGATAGG

CACCTATTGGTCTTACTGACATCCACTTTGCCTTTCTCTCCACAGGCCCAG

AGAGGAGACAGGCCGCCACC.

2. The method according to claim 1, wherein the rAAV variant comprises a VP1 protein having a sequence identity of at least 80% to the polypeptide of SEQ ID NO:19.

3. The method according to claim 2, wherein the VP1 protein has a sequence identity of at least 95% to the polypeptide of SEQ ID NO:19.

4. The method according to claim 3, wherein the VP1 protein has a sequence identity of at least 99% to the polypeptide of SEQ ID NO:19.

5. The method according to claim 4, wherein the VP1 protein has a sequence identity of 100% to the polypeptide of SEQ ID NO:19.

6. The method according to claim 1, wherein the subject is a primate.

7. A method for expressing a gene product in a cone photoreceptor in a subject, the method comprising:
   delivering into the vitreous of the eye an effective amount of recombinant adeno-associated virus (rAAV) variant comprising a polynucleotide that encodes the gene product, wherein:
   a) the rAAV variant comprises a variant AAV capsid protein comprising the amino acid sequence LGETTRP (SEQ ID NO:11) inserted into the GH loop of the VP1 capsid protein; and
   b) the polynucleotide comprises a regulatory cassette operably linked to a polynucleotide sequence encoding the gene product,
   wherein the regulatory cassette comprises the sequence:

(SEQ ID NO: 27)
CCTACAGCAGCCAGGGTGAGATTATGAGGCTGAGCTGAGAATATCAAGACT

GTACCGAGTAGGGGGCCTTGGCAAGTGTGGAGAGCCCGGCAGCTGGGGCAG

AGGGCGGAGTACGGTGTGCGTTTACGGACCTCTTCAAACGAGGTAGGAAGG

TCAGAAGTCAAAAAGGGAACAAATGATGTTTAACCACACAAAAATGAAAAT

CCAATGGTTGGATATCCATTCCAAATACACAAAGGCAACGGATAAGTGATC

CGGGCCAGGCACAGAAGGCCATGCACCCGTAGGATTGCACTCAGAGCTCCC

AAATGCATAGGAATAGAAGGGTGGGTGCAGGAGGCTGAGGGGTGGGGAAAG

GGCATGGGTGTTTCATGAGGACAGAGCTTCCGTTTCATGCAATGAAAAGAG

TTTGGAGACGGATGGTGGTGACTGGACTATACACTTACACACGGTAGCGAT

GGTACACTTTGTATTATGTATATTTTACCACGATCTTTTTAAAGTGTCAAA

GGCAAATGGCCAAATGGTTCCTTGTCCTATAGCTGTAGCAGCCATCGGCTG

TTAGTGACAAAGCCCCTGAGTCAAGATGACAGCAGCCCCCATAACTCCTAA

TCGGCTCTCCCGCGTGGAGTCATTTAGGAGTAGTCGCATTAGAGACAAGTC

CAACATCTAATCTTCCACCCTGGCCAGGGCCCCAGCTGGCAGCGAGGGTGG

GAGACTCCGGGCAGAGCAGAGGGCGCTGACATTGGGCCCGGCCTGGCTTG

GGTCCCTCTGGCCTTTCCCCAGGGGCCCTCTTTCCTTGGGGCTTTCTTGGG

CCGCCACTGCTCCCGCTCCTCTCCCCCATCCCACCCCCTCACCCCCTCGT

TCTTCATATCCTTCTCTAGTGCTCCCTCCACTTTCATCCACCCTTCTGCAA

GAGTGTGGGACCACAAATGAGTTTTCACCTGGCCTGGGGACACACGTGCCC

CCACAGGTGCTGAGTGACTTTCTAGGACAGTAATCTGCTTTAGGCTAAAAT

GGGACTTGATCTTCTGTTAGCCCTAATCATCAATTAGCAGAGCCGGTGAAG

GTGCAGAACCTACCGCCTTTCCAGGCCTCCTCCCACCTCTGCCACCTCCAC

-continued
TCTCCTTCCTGGGATGTGGGGCTGGCACACGTGTGGCCCAGGGCATTGGT

GGGATTGCACTGAGCTGGGTCATTAGCGTAATCCTGGACAAGGGCAGACAG

GGCGAGCGGAGGGCCAGCTCCGGGGCTCAGGCAAGGCTGGGGGCTTCCCCC

AGACACCCCACTCCTCCTCTGCTGGACCCCCACTTCATAGGGCACTTCGTG

TTCTCAAAGGGCTTCCAAATAGCATGGTGGCCTTGGATGCCCAGGGAAGCC

TCAGAGTTGCTTATCTCCCTCTAGACAGAAGGGGAATCTCGGTCAAGAGGG

AGAGGTCGCCCTGTTCAAGGCCACCCAGCCAGCTCATGGCGGTAATGGGAC

AAGGCTGGCCAGCCATCCCACCCTCAGAAGGGACCCGGTGGGGCAGGTGAT

CTCAGAGGAGGCTCACTTCTGGGTCTCACATTCTTCCAGCAAATCCCTCTG

AGCCGCCCCGGGGGCTCGCCTCAGGAGCAAGGAAGCAAGGGGTGGGAGGA

GGAGGTCTAAGTCCCAGGCCCAATTAAGAGATCAGATGGTGTAGGATTTGG

GAGCTTTTAAGGTGAAGAGGCCCGGGCTGATCCCACTGGCCGGTATAAAGC

ACCGTGACCCTCAGGTGACGCACCAGGGCCGGCTGCCGTCGGGGACAGGGC

TTTCCATAGCCCAGGTAAGTATCAAGGTTACAAGACAGGTTTAAGGAGACC

AATAGAAACTGGGCTTGTCGAGACAGAGAAGACTCTTGCGTTTCTGATAGG

CACCTATTGGTCTTACTGACATCCACTTTGCCTTTCTCTCCACAGGCCCAG

AGAGGAGACAGGCCGCCACC.

8. The method according to claim 7, wherein the rAAV variant comprises a VP1 protein having a sequence identity of at least 80% to the polypeptide of SEQ ID NO:19.

9. The method according to claim 8, wherein the VP1 protein has a sequence identity of at least 95% to the polypeptide of SEQ ID NO:19.

10. The method according to claim 9, wherein the VP1 protein has a sequence identity of at least 99% to the polypeptide of SEQ ID NO:19.

11. The method according to claim 10, wherein VP1 protein has a sequence identity of 100% to the polypeptide of SEQ ID NO:19.

12. The method according to claim 7, wherein the method further comprises detecting the expression of the polynucleotide in the cone photoreceptor.

13. The method according to claim 7, wherein the subject is a primate.

14. A method for treating or preventing a cone-associated retinal disorder in a subject having or at risk for developing a cone-associated retinal disorder, the method comprising:
   administering intravitreally a recombinant adeno-associated virus (rAAV) variant comprising a therapeutic polynucleotide in an amount effective to treat or prevent the cone-associated retinal disorder, wherein:
   a) the rAAV variant comprises a variant AAV capsid protein comprising the amino acid sequence LGETTRP (SEQ ID NO:11) inserted into the GH loop of the VP1 capsid protein; and
   b) the therapeutic polynucleotide comprises a regulatory cassette operably linked to a polynucleotide sequence encoding a therapeutic protein,
   wherein the regulatory cassette comprises the sequence:

(SEQ ID NO: 27)
CCTACAGCAGCCAGGGTGAGATTATGAGGCTGAGCTGAGAATATCAAGACT

GTACCGAGTAGGGGGCCTTGGCAAGTGTGGAGAGCCCGGCAGCTGGGGCAG

-continued
AGGGCGGAGTACGGTGTGCGTTTACGGACCTCTTCAAACGAGGTAGGAAGG

TCAGAAGTCAAAAAGGGAACAAATGATGTTTAACCACACAAAAATGAAAAT

CCAATGGTTGGATATCCATTCCAAATACACAAAGGCAACGGATAAGTGATC

CGGGCCAGGCACAGAAGGCCATGCACCCGTAGGATTGCACTCAGAGCTCCC

AAATGCATAGGAATAGAAGGGTGGGTGCAGGAGGCTGAGGGGTGGGGAAAG

GGCATGGGTGTTTCATGAGGACAGAGCTTCCGTTTCATGCAATGAAAAGAG

TTTGGAGACGGATGGTGGTGACTGGACTATACACTTACACACGGTAGCGAT

GGTACACTTTGTATTATGTATATTTTACCACGATCTTTTTAAAGTGTCAAA

GGCAAATGGCCAAATGGTTCCTTGTCCTATAGCTGTAGCAGCCATCGGCTG

TTAGTGACAAAGCCCCTGAGTCAAGATGACAGCAGCCCCCATAACTCCTAA

TCGGCTCTCCCGCGTGGAGTCATTTAGGAGTAGTCGCATTAGAGACAAGTC

CAACATCTAATCTTCCACCCTGGCCAGGGCCCCAGCTGGCAGCGAGGGTGG

GAGACTCCGGGCAGAGCAGAGGGCGCTGACATTGGGGCCCGGCCTGGCTTG

GGTCCCTCTGGCCTTTCCCCAGGGGCCCTCTTTCCTTGGGGCTTTCTTGGG

CCGCCACTGCTCCCGCTCCTCTCCCCCCATCCCACCCCCTCACCCCCTCGT

TCTTCATATCCTTCTCTAGTGCTCCCTCCACTTTCATCCACCCTTCTGCAA

GAGTGTGGGACCACAAATGAGTTTTCACCTGGCCTGGGGACACACGTGCCC

CCACAGGTGCTGAGTGACTTTCTAGGACAGTAATCTGCTTTAGGCTAAAAT

GGGACTTGATCTTCTGTTAGCCCTAATCATCAATTAGCAGAGCCGGTGAAG

GTGCAGAACCTACCGCCTTTCCAGGCCTCCTCCCACCTCTGCCACCTCCAC

TCTCCTTCCTGGGATGTGGGGCTGGCACACGTGTGGCCCAGGGCATTGGT

GGGATTGCACTGAGCTGGGTCATTAGCGTAATCCTGGACAAGGGCAGACAG

GGCGAGCGGAGGGCCAGCTCCGGGGCTCAGGCAAGGCTGGGGGCTTCCCCC

AGACACCCCACTCCTCCTCTGCTGGACCCCCACTTCATAGGGCACTTCGTG

TTCTCAAAGGGCTTCCAAATAGCATGGTGGCCTTGGATGCCCAGGGAAGCC

TCAGAGTTGCTTATCTCCCTCTAGACAGAAGGGGAATCTCGGTCAAGAGGG

AGAGGTCGCCCTGTTCAAGGCCACCCAGCCAGCTCATGGCGGTAATGGGAC

AAGGCTGGCCAGCCATCCCACCCTCAGAAGGGACCCGGTGGGGCAGGTGAT

CTCAGAGGAGGCTCACTTCTGGGTCTCACATTCTTCCAGCAAATCCCTCTG

AGCCGCCCCGGGGGCTCGCCTCAGGAGCAAGGAAGCAAGGGGTGGGAGGA

GGAGGTCTAAGTCCCAGGCCCAATTAAGAGATCAGATGGTGTAGGATTTGG

GAGCTTTTAAGGTGAAGAGGCCCGGGCTGATCCCACTGGCCGGTATAAAGC

ACCGTGACCCTCAGGTGACGCACCAGGGCCGGCTGCCGTCGGGGACAGGGC

TTTCCATAGCCCAGGTAAGTATCAAGGTTACAAGACAGGTTTAAGGAGACC

AATAGAAACTGGGCTTGTCGAGACAGAGAAGACTCTTGCGTTTCTGATAGG

CACCTATTGGTCTTACTGACATCCACTTTGCCTTTCTCTCCACAGGCCCAG

AGAGGAGACAGGCCGCCACC.

15. The method according to claim 14, wherein the VP1 protein having a sequence identity of at least 80% to the polypeptide of SEQ ID NO:19.

16. The method according to claim 15, wherein the VP1 protein has a sequence identity of at least 95% to the polypeptide of SEQ ID NO:19.

17. The method according to claim 16, wherein the VP1 protein has a sequence identity of at least 99% to the polypeptide of SEQ ID NO:19.

18. The method according to claim 17, wherein the VP1 protein has a sequence identity of 100% to the polypeptide of SEQ ID NO:19.

19. The method according to claim 14, wherein the retinal disorder is a cone-associated disorder.

20. The method according to claim 19, wherein the cone-associated disorder is selected from the group consisting of rod-cone dystrophy; cone-rod dystrophy; progressive cone dystrophy; retinitis pigmentosa (RP); Stargardt Disease; macular telangiectasia, Leber hereditary optic neuropathy, Best's disease; adult vitelliform macular dystrophy; X-linked retinoschisis; a color vision disorder; age-related macular degeneration; wet age-related macular degeneration; geographic atrophy; diabetic retinopathy; a retinal vein occlusion; retinal ischemia; Familial Exudative Vitreoretinopathy (FEVR); COATs disease; and Sorsby's fundus dystrophy.

21. The method according to claim 14, wherein the subject is a primate.

22. The method according to claim 14, wherein the retinal disorder is a color vision disorder.

23. The method according to claim 22, wherein the color vision disorder is blue cone monochromacy.

24. The method according to claim 22, wherein the color vision disorder is color vision deficiency.

* * * * *